US012735395B2

(12) United States Patent
Nishimura et al.

(10) Patent No.: US 12,735,395 B2
(45) Date of Patent: Sep. 15, 2026

(54) COMPOUND, AND COMPOSITION FOR FORMING HOLE TRANSPORTING LAYER FOR PEROVSKITE SOLAR CELLS

(71) Applicant: TOKYO CHEMICAL INDUSTRY CO., LTD., Tokyo (JP)

(72) Inventors: Hidetaka Nishimura, Saitama (JP); Iku Okada, Saitama (JP); Taro Tanabe, Tokyo (JP); Atsushi Wakamiya, Uji (JP)

(73) Assignee: TOKYO CHEMICAL INDUSTRY CO., LTD., Tokyo (JP)

(*) Notice: Subject to any disclaimer, the term of this patent is extended or adjusted under 35 U.S.C. 154(b) by 1249 days.

(21) Appl. No.: 17/258,399

(22) PCT Filed: Aug. 1, 2019

(86) PCT No.: PCT/JP2019/030162
§ 371 (c)(1),
(2) Date: Jan. 6, 2021

(87) PCT Pub. No.: WO2020/036069
PCT Pub. Date: Feb. 20, 2020

(65) Prior Publication Data

US 2021/0319957 A1 Oct. 14, 2021

(30) Foreign Application Priority Data

Aug. 16, 2018 (JP) ................................ 2018-153174

(51) Int. Cl.
*C07D 333/26* (2006.01)
*C07C 25/18* (2006.01)
(Continued)

(52) U.S. Cl.
CPC ............ *C07D 333/26* (2013.01); *C07C 25/18* (2013.01); *C07C 25/28* (2013.01); *C07C 211/54* (2013.01); *C07C 217/92* (2013.01); *C07C 223/06* (2013.01); *C07C 323/36* (2013.01); *C07D 209/86* (2013.01); *C07D 333/22* (2013.01); *C07D 495/04* (2013.01); *C07D 519/00* (2013.01); *C07F 9/4056* (2013.01); *H01G 9/2009* (2013.01); *H01G 9/2018* (2013.01); *H10K 85/30* (2023.02); *H10K 85/50* (2023.02); *H10K 85/631* (2023.02); *H10K 85/636* (2023.02); *C07C 2601/16* (2017.05); *C07C 2603/97* (2017.05); *H10K 30/20* (2023.02);
(Continued)

(58) Field of Classification Search
CPC ... C07C 211/54; C07C 217/92; C07C 223/06; C07C 323/36
See application file for complete search history.

(56) References Cited

FOREIGN PATENT DOCUMENTS

JP 2010123376 A 6/2010

OTHER PUBLICATIONS

Machine translation by WIPO Translate of JP 2010123376 (published as JP 5245748) 14 pages, Jun. 3, 2010.*
(Continued)

*Primary Examiner* — Brenda L Coleman
*Assistant Examiner* — Madeline E Braun
(74) *Attorney, Agent, or Firm* — Davis Wright Tremaine LLP

(57) ABSTRACT

Provided are: a composition for forming a hole transporting layer for perovskite solar cells, which is inexpensive and does not need to be used together with a dopant; and a compound which can be contained in a composition for forming a hole transporting layer. A compound represented by general formula (I) (wherein Ar represents an aryl group; A represents a structure represented by formula (II); Z's independently represent a hydrogen atom, a structure represented by general formula (III), or a structure represented by formula (IV), and may be the same as or different from each other, wherein a case where each of Z's is a hydrogen atom is excluded; Y's independently represent at least one member selected from the group mentioned below; $R^1$ and $R^2$ independently represent a hydrogen atom, an alkyl group, or an alkoxy group, or $R^1$ and $R^2$ may together form a ring having one or two oxygen atoms; X's independently represent an alkyl group, an alkoxy group, an alkylthio group, a monoalkylamino group, or a dialkylamino group, each of which may be substituted by a halogen atom; k represents 0 or 1; 1 represents 2 or 3; m represents an integer of 1 to 6; and r represents 1 or 2; wherein, when k is 0, 1 is 3, and m is 1, all three bonds of A are bonded to Z.

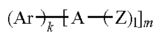

(I)

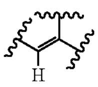

(II)

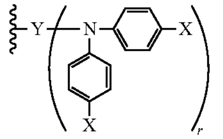

(III)

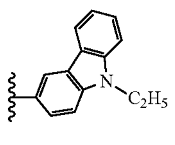

(IV)

Y:

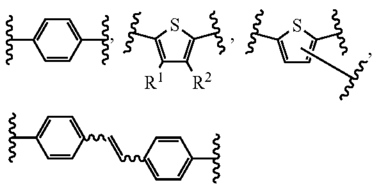

5 Claims, 1 Drawing Sheet

(51) Int. Cl.

| | |
|---|---|
| ***C07C 25/28*** | (2006.01) |
| ***C07C 211/54*** | (2006.01) |
| ***C07C 217/92*** | (2006.01) |
| ***C07C 223/06*** | (2006.01) |
| ***C07C 323/36*** | (2006.01) |
| ***C07D 209/86*** | (2006.01) |
| ***C07D 333/22*** | (2006.01) |
| ***C07D 495/04*** | (2006.01) |
| ***C07D 519/00*** | (2006.01) |
| ***C07F 9/40*** | (2006.01) |
| ***H01G 9/20*** | (2006.01) |
| ***H10K 30/20*** | (2023.01) |
| ***H10K 30/50*** | (2023.01) |
| ***H10K 85/30*** | (2023.01) |
| ***H10K 85/50*** | (2023.01) |
| ***H10K 85/60*** | (2023.01) |

(52) U.S. Cl.

CPC ........... *H10K 30/50* (2023.02); *H10K 85/655* (2023.02); *H10K 85/657* (2023.02)

(56) References Cited

OTHER PUBLICATIONS

Li et al., Highly Efficient p-i-n Perovskite Solar Cells Utilizing Novel Low-Temperature Solution-Processed Hole Transport Materials with Linear π-Conjugated Structure, Small, vol. 12, No. 35, pp. 4902-4908 (2016).*

* cited by examiner

【Figure 1】
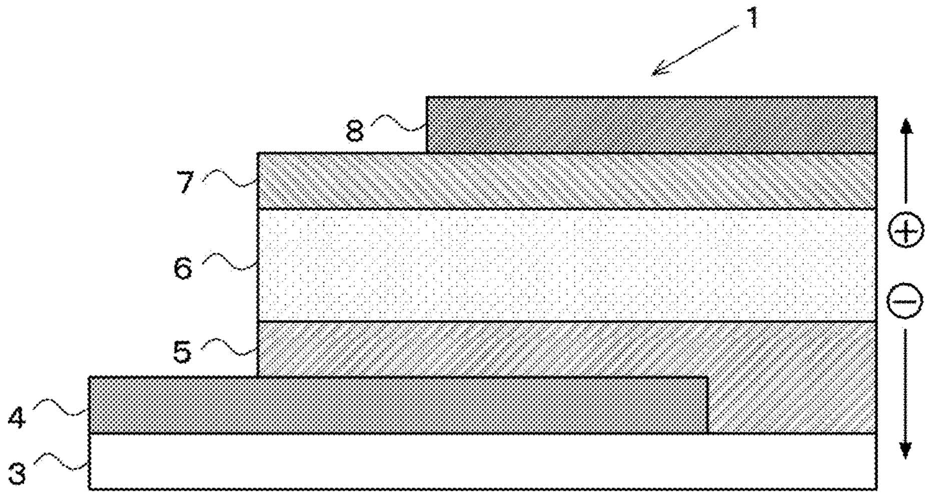
【Figure 2】
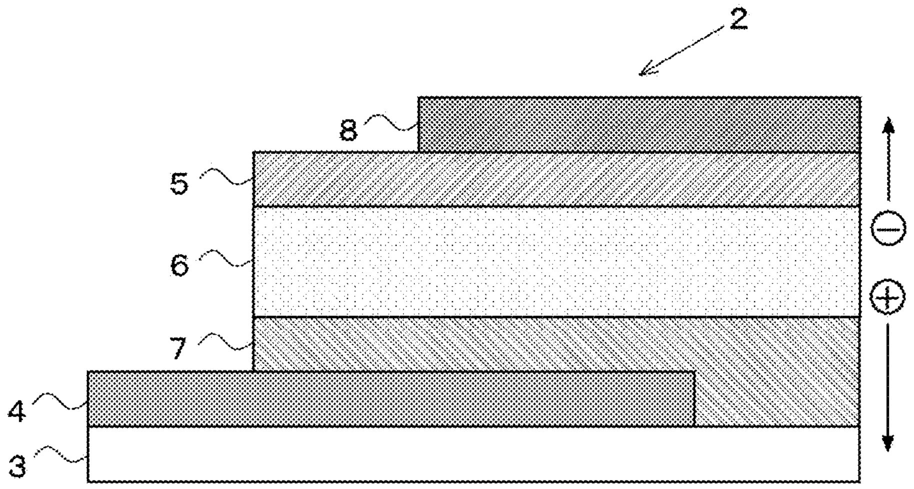

COMPOUND, AND COMPOSITION FOR FORMING HOLE TRANSPORTING LAYER FOR PEROVSKITE SOLAR CELLS

CROSS-REFERENCE TO RELATED APPLICATIONS

The present application is a U.S. National Stage entry under 35 U.S.C. § 371 of International Application No. PCT/JP2019/030162, filed on Aug. 1, 2019, designating the United States of America and published in Japanese on Feb. 20, 2020, which in turn claims priority to J.P. Application No. 2018-153174, filed on Aug. 16, 2018, each of which is hereby incorporated by reference in its entirety.

TECHNICAL FIELD

The present invention relates to a composition for forming a hole transporting layer for perovskite solar cells.

BACKGROUND ART

Silicon solar cells, which are currently in widespread use as solar cells, have high manufacturing costs and limited installation locations.

Dye-sensitized solar cells and perovskite solar cells have been developed as solar cells to replace the silicon solar cells.

Dye-sensitized solar cells are characterized in that they are used as photoelectrodes by adsorbing dyes on the surface of titanium oxide to improve their sensitivity to light. However, in dye-sensitized solar cells, they are necessary to make electrolyte solutions exist between the photoelectrode and the counter electrode to carry out the reduction reaction of the oxidized dyes. The presence of this electrolyte solution hinders reduced durability, leakage and development into a free shape.

The perovskite solar cells are solar cells using a metal halide material having a perovskite structure as a light absorption layer. Since perovskite solar cells can be manufactured by coating with a solution, the manufacturing cost can be suppressed and the perovskite solar cells can be formed on a curved surface.

The structure of the perovskite solar cells is shown in FIG. 1. As shown in FIG. 1, the perovskite solar cell has a structure in which a hole transport layer 7 and an electron transport layer 5 are laminated above and below the perovskite layer 6, and the laminate is sandwiched between electrodes 4 and 8. The driving principle of the perovskite solar cell is that holes and electrons are first generated by light absorption in the perovskite layer 6. The generated holes and electrons move to the hole transport layer 7 and the electron transport layer 5, respectively, and further move to the electrodes 4 and 8 via the respective layers.

The hole-transporting layer of perovskite solar cells contains a hole-transporting compound, and Spiro-OMeTAD is known as this hole-transporting compound (Patent Literature 1).

CITATION LIST

Patent Literature

[Patent Literature 1] JP-A 2017-50246

SUMMARY OF INVENTION

Technical Problem

However, Spiro-OMeTAD is very expensive, and the cost of manufacturing solar cells is high.

Further, Spiro-OMeTAD needs to be used together with some dopants, and there are problems that these dopants lower the durability of solar cell devices.

Given the situation, an object of the present invention is to provide a hole transport layer forming composition and compounds contained in the hole transport layer forming composition of perovskite solar cells which are inexpensive and does not need to be used together with dopants.

Solution to Problem

The present invention has, for example, the following configuration.

[1] A compound represented by the following general formula [1]:

General Formula [1]

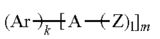

(I)

[In the general formula [1], Ar is an aryl group, and when Ar is composed of a plurality of aromatic rings, A may be bonded to a plurality of aromatic rings, A is a structure represented by the following formula (II), and Z is a structure represented by the following general formula (III) or a structure represented by the following formula (IV), which may be the same or different from each other. However, all of Z is not hydrogen.

General Formula [2]

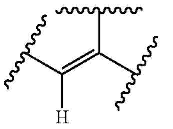

(II)

General Formula [3]

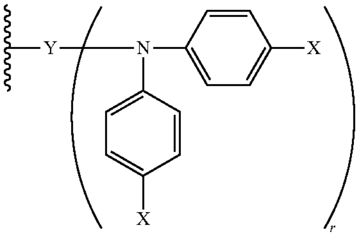

(III)

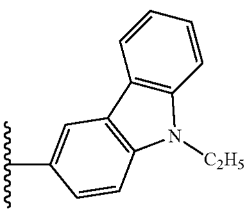

(IV)

In the structure represented by the above general formula (III), Y is at least one species independently selected from the following groups.

[General Formula [4]]

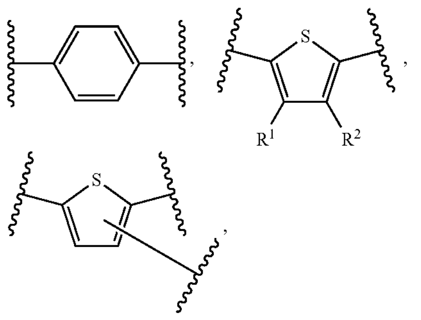

General Formula [5]

-continued

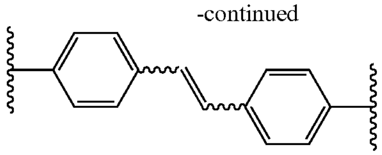

$R^1$ and $R^2$ may be independently hydrogen, alkyl groups, or alkoxy groups, or $R^1$ and $R^2$ may be combined to form a ring having one or two oxygen atoms.

X is an alkyl group, an alkoxy group, an alkylthio group, a monoalkylamino group or a dialkylamino group, which may be independently substituted with halogen, respectively.

k is 0 or 1, l is 2 or 3, m is an integer from 1 to 6, r is 1 or 2, where when k is 0, l is 3 and m is 1.

Yes, all three of A's hands are bound to Z.)

However, compounds excluding the following compounds.

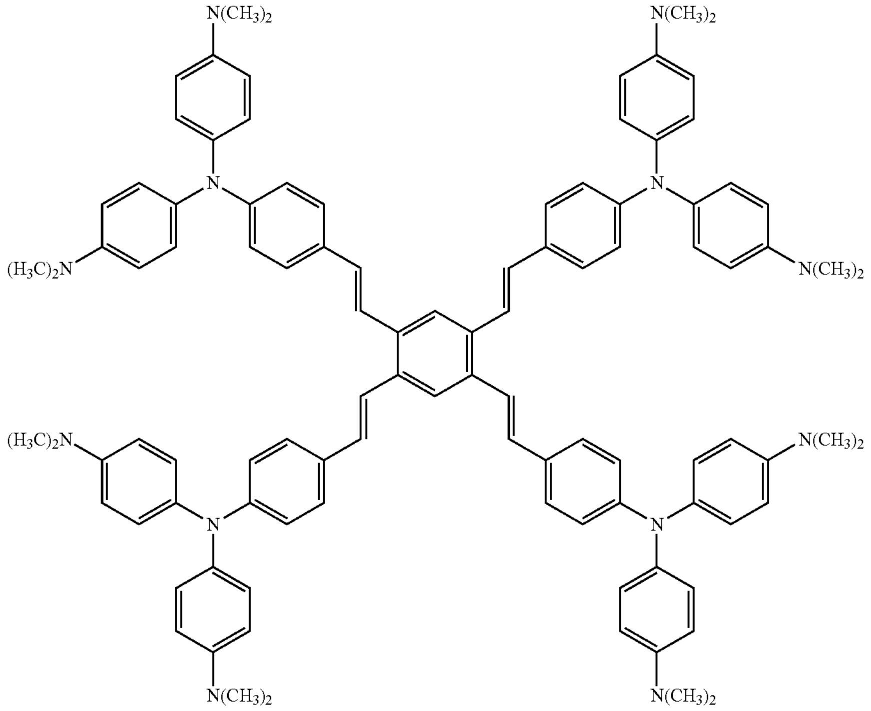

-continued
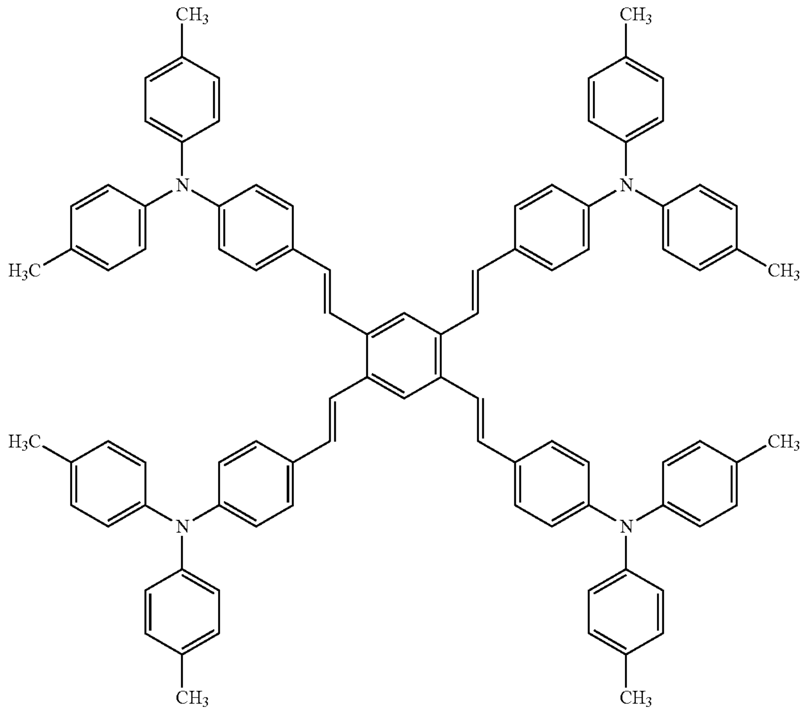
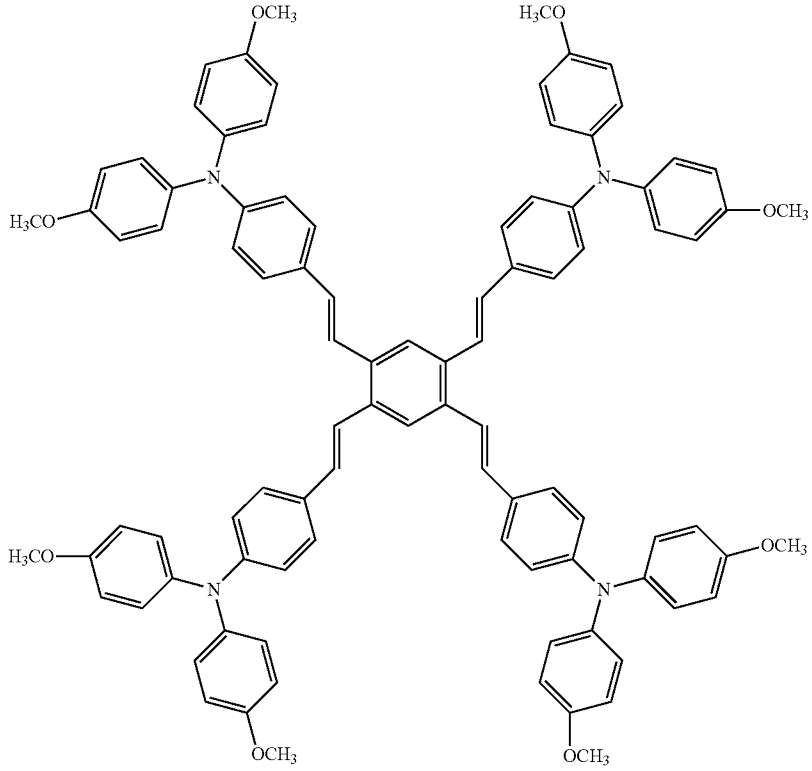 [SMILES: COc1ccc(N(c2ccc(/C=C/c3cc(/C=C/c4ccc(N(c5ccc(OC)cc5)c5ccc(OC)cc5)cc4)c(/C=C/c4ccc(N(c5ccc(OC)cc5)c5ccc(OC)cc5)cc4)cc3/C=C/c3ccc(N(c4ccc(OC)cc4)c4ccc(OC)cc4)cc3)cc2)c2ccc(OC)cc2)cc1]

-continued
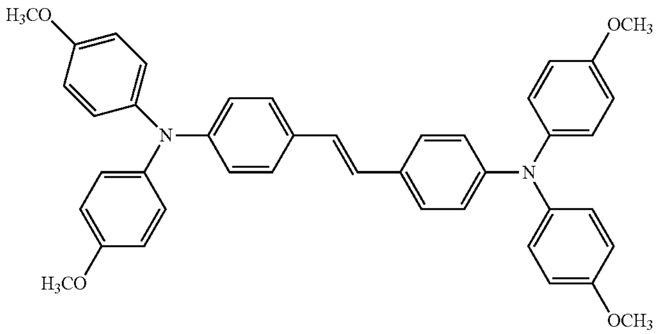
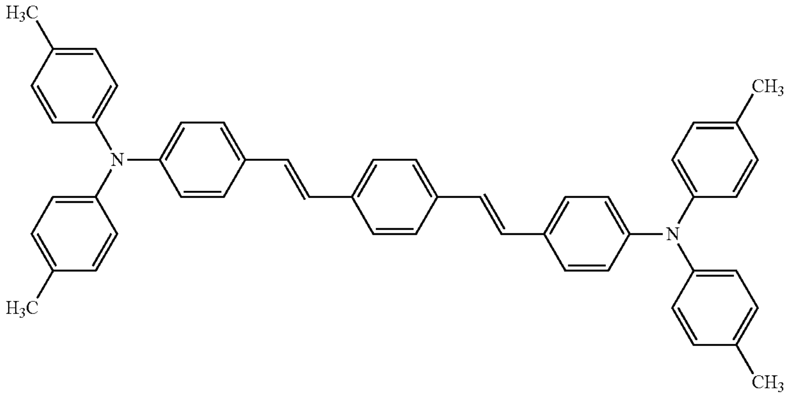
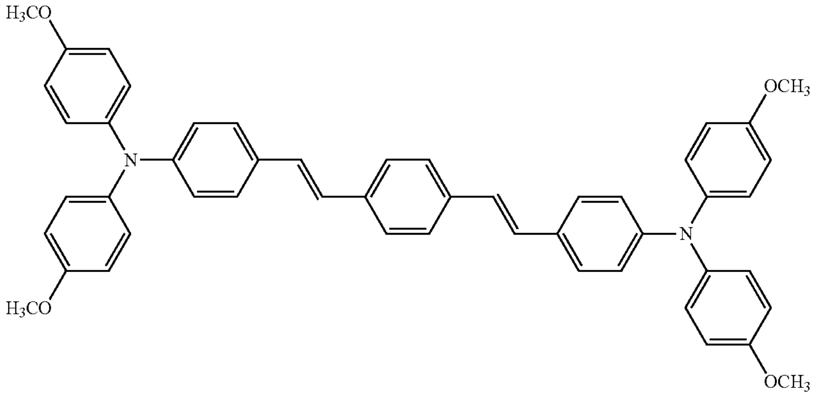
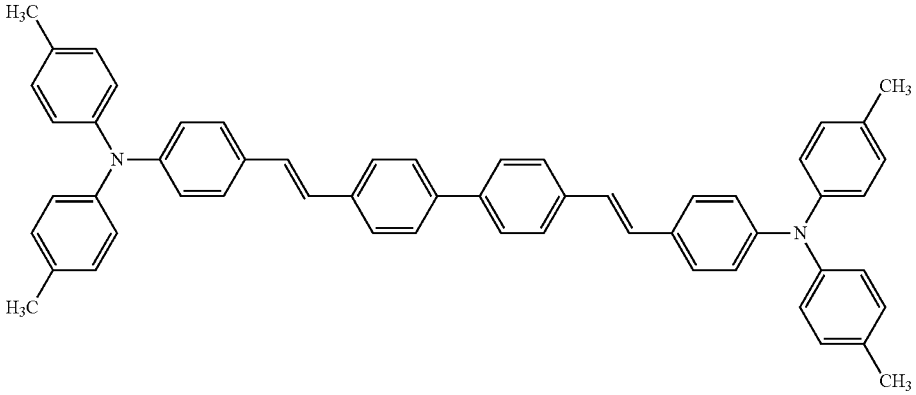
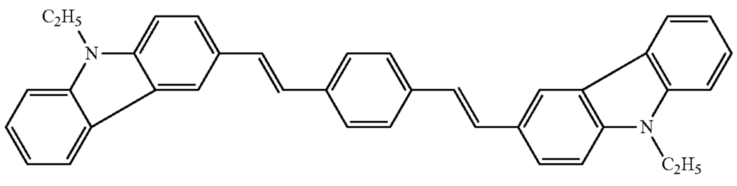

-continued
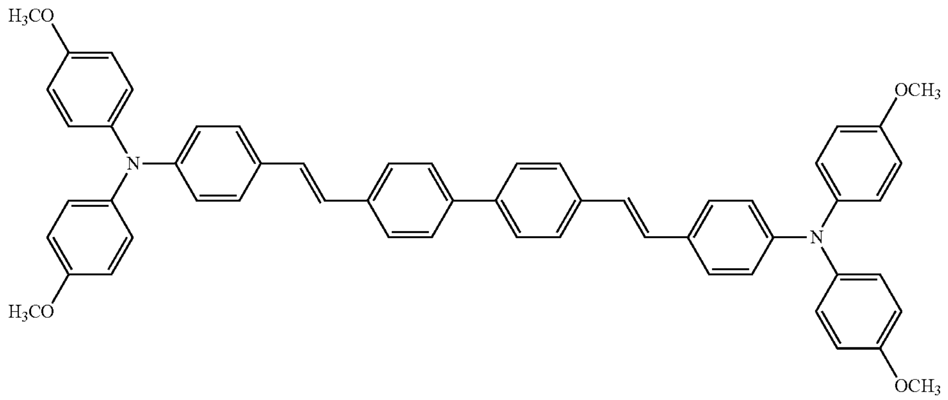
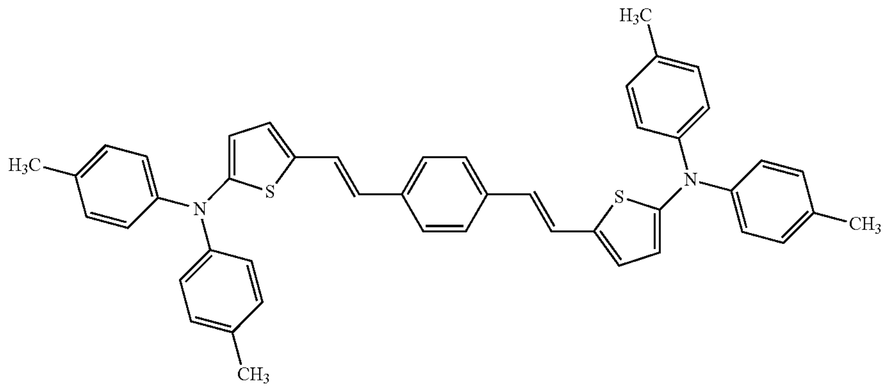
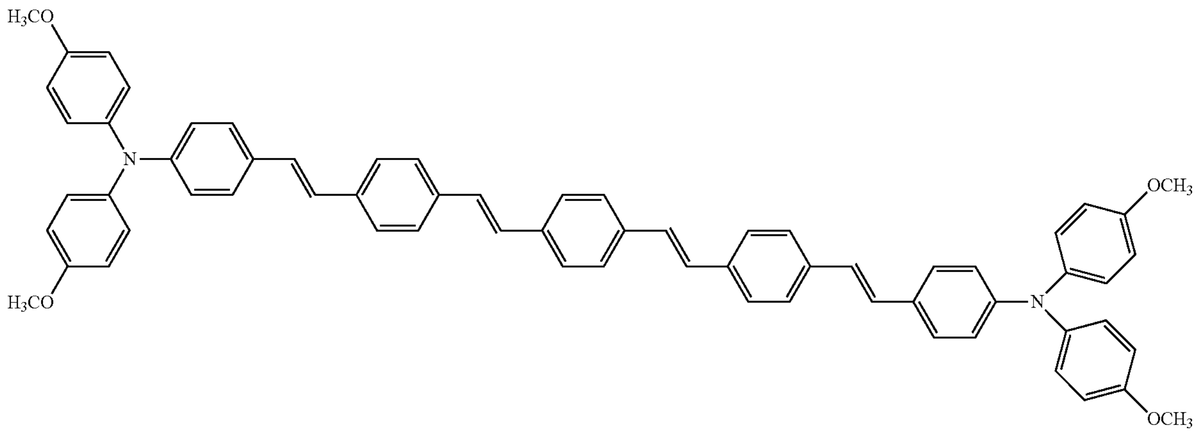

[2] The compound of [1], wherein the compound represented by the general formula (I) is a compound represented by the following general formulas (V), (VI), (VII) or (XXVII).

General Formula [6]

(V)

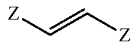

(VI)

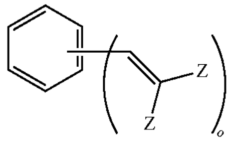

(VII)

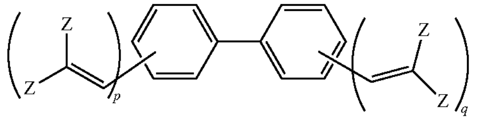

(XXVII)

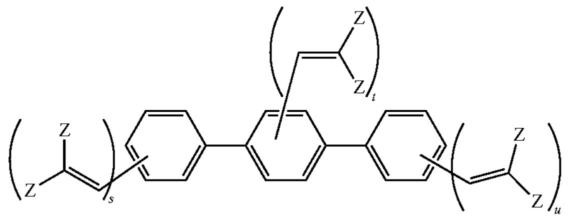

(In the general formula (VI), o is an integer of 1 to 6, in the general formula (VII), p is an integer of 1 to 5, q is an integer of 1 to 5, and in the general formula (XXVII), s is an integer of 1 to 5, t is an integer of 1 to 4, u is an integer of 1 to 5, and the general formula (V) shows that the configuration of the double bond is cis or trans. In any of the general formulas (V), (VI), (VII) and (XXVII), Z is synonymous with the definition in the general formula (I), but is represented by the general formula (V). In each of these compounds, the structure is independently represented by the general formula (III) or the structure represented by the formula (IV).)

[3] A hole transport layer forming composition for a perovskite solar cells containing a compound represented by the following general formula (VIII) and a solvent and containing no dopant.

General Formula [7]

$$(Ar)_k[A(Z)_l]_m \qquad \text{(VIII)}$$

(In the general formula (VIII), Ar is an aryl group, and when Ar is composed of a plurality of aromatic rings, A may be bonded to a plurality of aromatic rings, and A is represented by the following formula (II). Z is hydrogen, a structure represented by the following general formula (III) or a structure represented by the following formula (IV), which may be the same or different from each other. However, all of Z is not hydrogen.

General Formula [8]

(II)

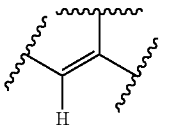

General Formula [9]

(III)

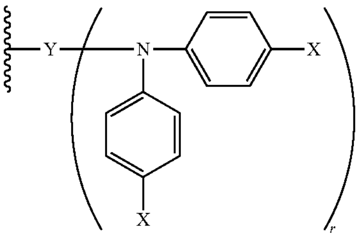

(IV)

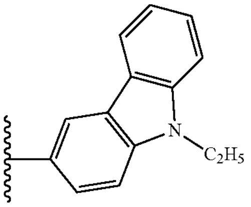

In the structure represented by the above general formula (III), Y is at least one species independently selected from the following groups.

General Formula [10]

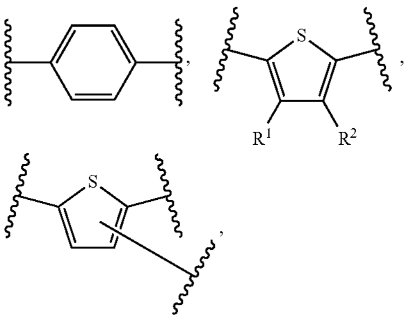

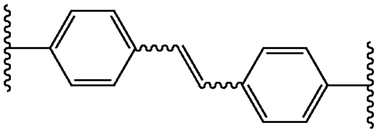

$R^1$ and $R^2$ may be independently hydrogen, alkyl groups, or alkoxy groups, or $R^1$ and $R^2$ may be combined to form a ring having one or two oxygen atoms.

X is an alkyl group, an alkoxy group, an alkylthio group, a monoalkylamino group or a dialkylamino group, which may be independently substituted with halogen, respectively.

k is 0 or 1, l is 2 or 3, m is an integer from 1 to 6, r is 1 or 2, where when k is 0, l is 3 and m is 1.

Yes, all three of A's hands are bound to Z.)

However, the compound represented by the general formula (VIII) is a hole transport layer forming composition for a perovskite solar cells excluding the following compounds.

General Formula [11]
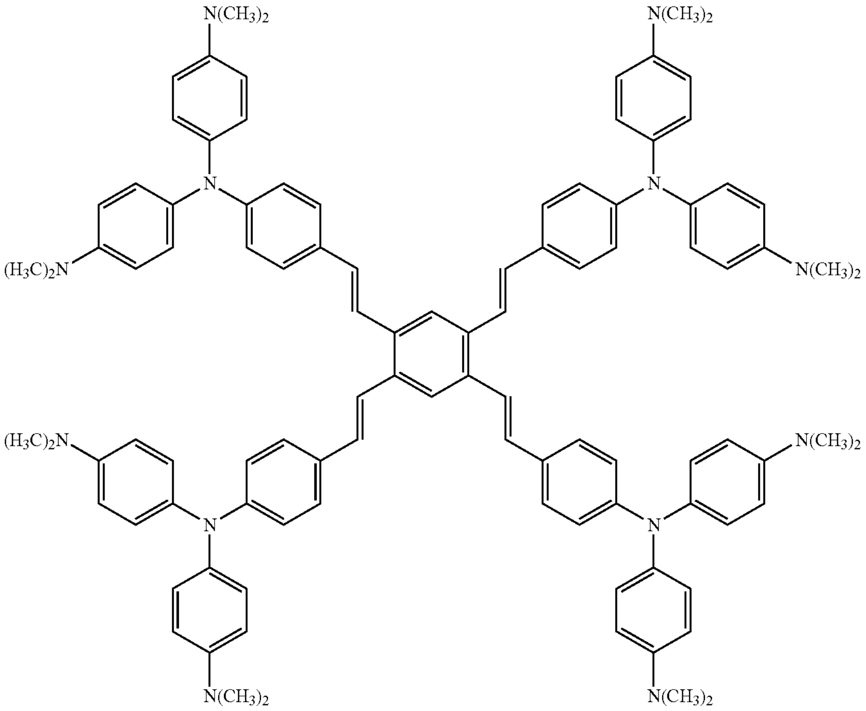
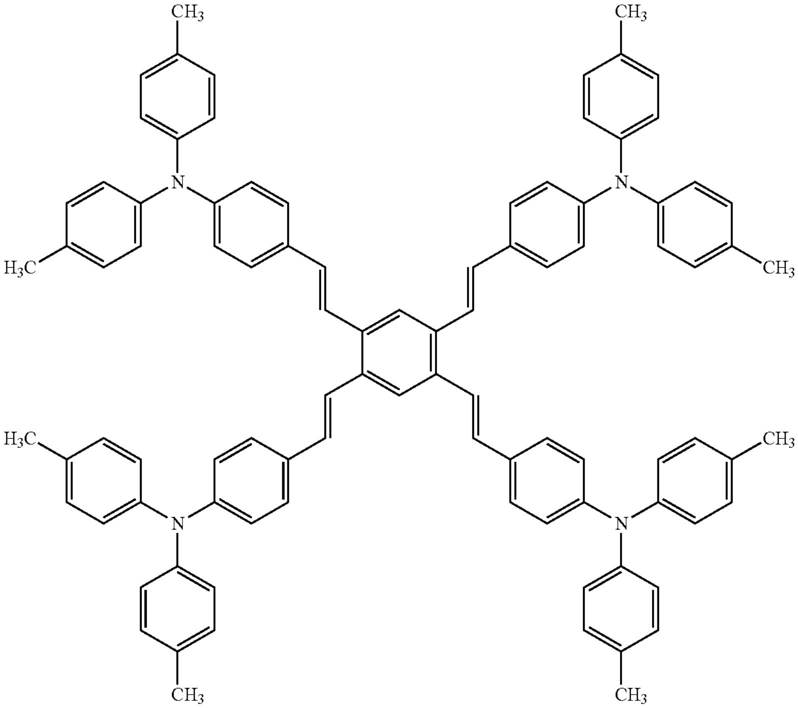

-continued

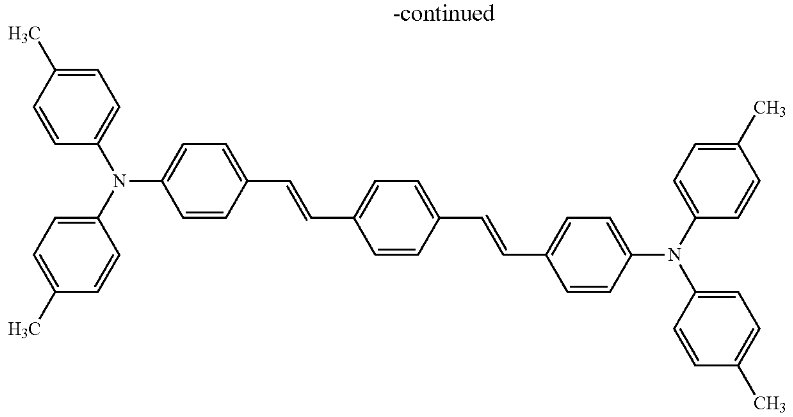

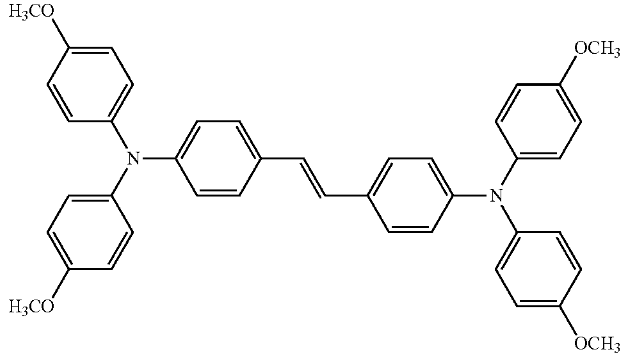

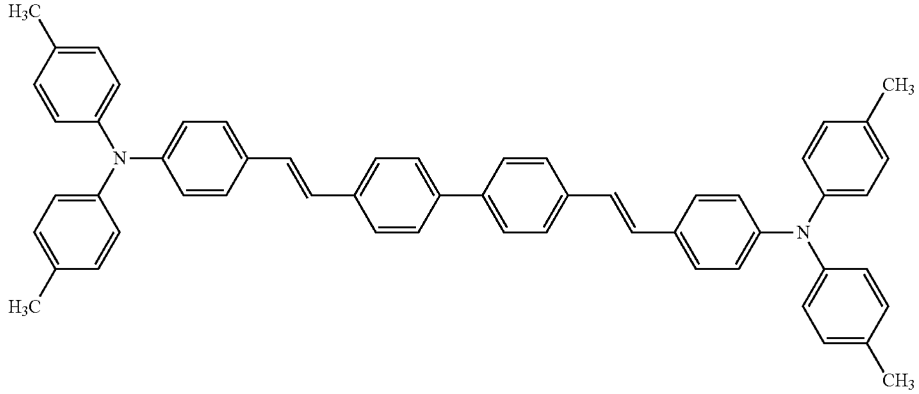

[4] The compound represented by the general formula (VIII) is a compound represented by the following general formula (V), (VI), (VII) or (XXVII). Hole transport for a perovskite solar cell according to [3] Layer formation composition.

General Formula [12]

(V)

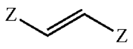

(VI)

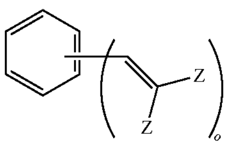

-continued (VII)

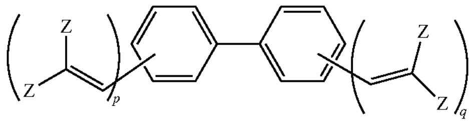

(XXVII)

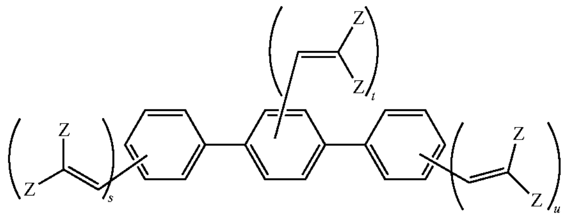

(In the general formula (VI), o is an integer of 1 to 6, in the general formula (VII), p is an integer of 1 to 5, q is an integer of 1 to 5, and in the general formula (XXVII), s is an integer of 1 to 5, t is an integer of 1 to 4, u is an integer of 1 to 5, and the general formula (V) shows that the configuration of the double bond is cis or trans. In any of the general formulas (V), (VI), (VII), and (XXVII), Z is synonymous with the definition in the general formula (VIII), but is represented by the general formula (V). In each of these compounds, the structure is independently represented by the general formula (III) or the structure represented by the formula (IV).)

[5] The compound represented by the general formula (VIII) is (i) a compound represented by the general formula (VI), and Z has hydrogen or a structure represented by the following general formula (III). The two Zs bonded to one carbon have a structure of hydrogen on one side and the structure of the following general formula (III) on the other side.

General Formula [13]

(III)

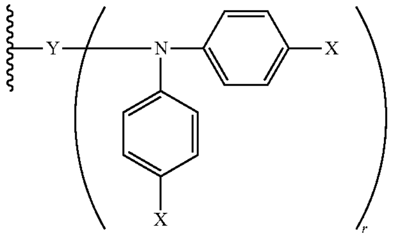

In the structure represented by the general formula (III), Y has the following structure.

General Formula [14]

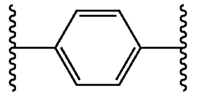

X is independently —OR, —SR, or —NR2, where R=CnH2n+1, an integer of n=1-10, o is 2, and r is 1. Compound, (Ii) A compound represented by the general formula (VI), in which Z is hydrogen or a structure represented by the following general formula (III), and one of the two Zs bonded to one carbon is one. Hydrogen, the other is the structure of the following general formula (III), General Formula [15]

(III)

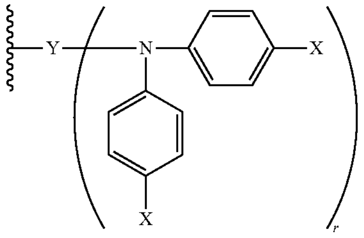

In the structure represented by the general formula (III), Y is a combination of one selected from the following (A) and (B).

General Formula [16]

(A)

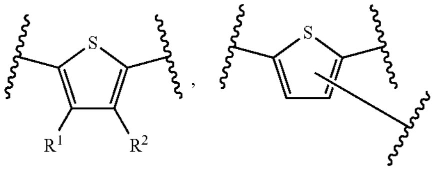

(B)

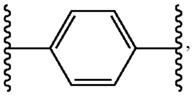

X is each independently —OR, —SR, or —NR2, where $R=C_nH_{2n+1}$, and $R^1$ and $R^2$ are both hydrogen or a ring having two oxygen atoms. A compound in which n=an integer of 1 to 10, o is 2, and r is 1 or 2.

(Iii) A compound represented by the general formula (VI), in which Z is hydrogen or a structure represented by the following general formula (III), and one of the two Zs bonded to one carbon is one. Hydrogen, the other is the structure of the following general formula (III), General Formula [17]

(III)

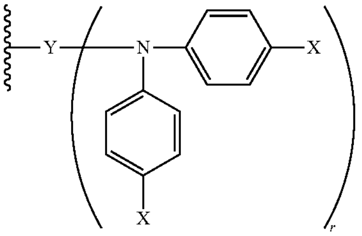

In the structure represented by the general formula (III), Y has the following structure.

General Formula [18]

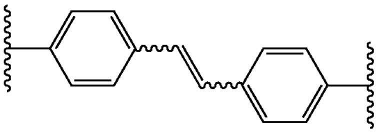

In a compound, X is independently —OR, —SR, or $—NR_2$, where $R=C_nH_{2n+1}$, n=an integer of 1-10, o is 2, and r is 1 or 2.

(Iv) A compound represented by the general formula (XXVII) in which Z is hydrogen or a structure represented by the following general formula (III), and one of the two Zs bonded to one carbon is one. Hydrogen, the other is the structure of the following general formula (III), General Formula [19]

(III)

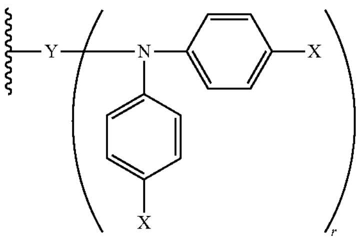

In the structure represented by the general formula (III), Y has the following structure.

General Formula [20]

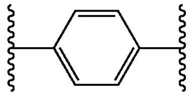

X is independently —OR, —SR, or —$NR_2$, where $R=C_nH_{2n+1}$, an integer of n=1-10, s is 1, and t is 2, U is 1 and r is 1.

The hole transport layer forming composition for a perovskite solar cell according to [4], which is at least one compound selected from the group consisting of.

[6] A compound represented by the following general formula (VIII).

General Formula [21]

$$(Ar)_k[A(Z)_l]_m \qquad (VIII)$$

(In the general formula (VIII), Ar is an aryl group, and when Ar is composed of a plurality of aromatic rings, A may be bonded to a plurality of aromatic rings, and A is represented by the following formula (II). Z is hydrogen, a structure represented by the following general formula (III) or a structure represented by the following formula (IV), which may be the same or different from each other. However, all of Z is not hydrogen.

General Formula [22]

(II)

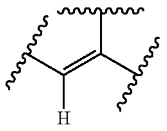

-continued

General Formula [23]

(III)

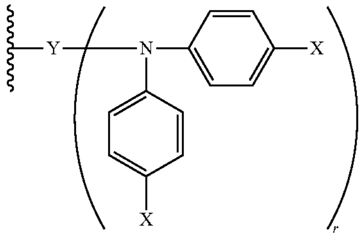

(IV)

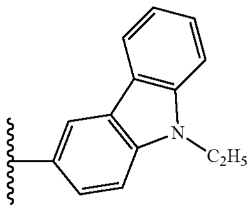

In the structure represented by the above general formula (III), Y is at least one species independently selected from the following groups.

General Formula [24]

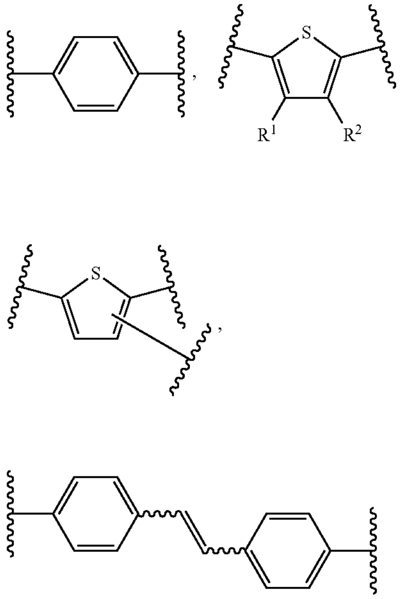

$R^1$ and $R^2$ may be independently hydrogen, alkyl groups, or alkoxy groups, or $R^1$ and $R^2$ may be combined to form a ring having one or two oxygen atoms.

X is an alkyl group, an alkoxy group, an alkylthio group, a monoalkylamino group or a dialkylamino group, which may be independently substituted with halogen, respectively.

k is 0 or 1, l is 2 or 3, m is an integer from 1 to 6, r is 1 or 2, where when k is 0, 1 is 3 and m is 1.

Yes, all three of A's hands are bound to Z.

A perovskite solar cell having a hole transport layer containing compounds other than the following compounds.

General Formula [25]
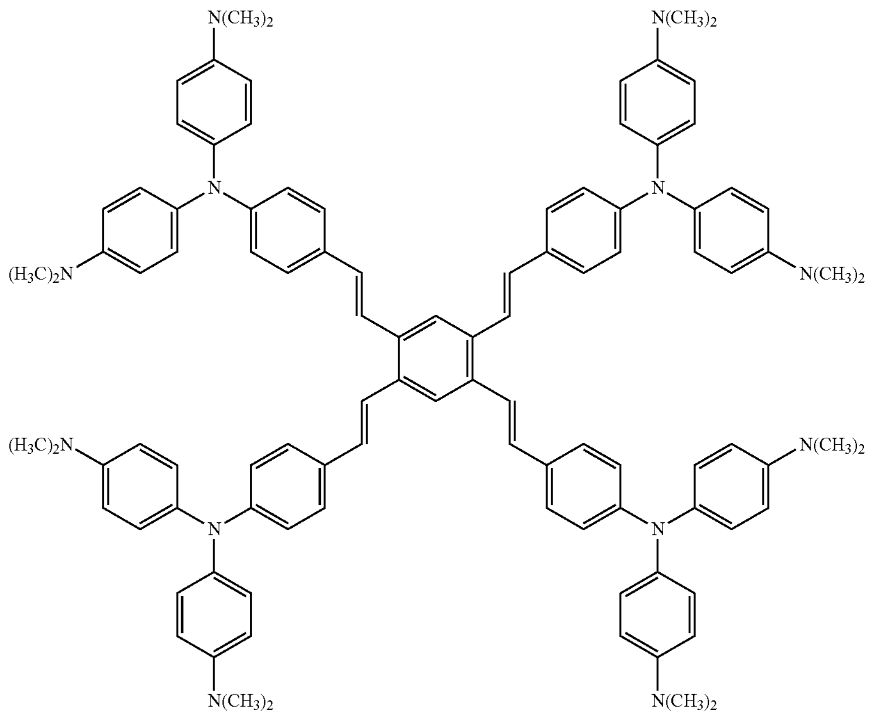
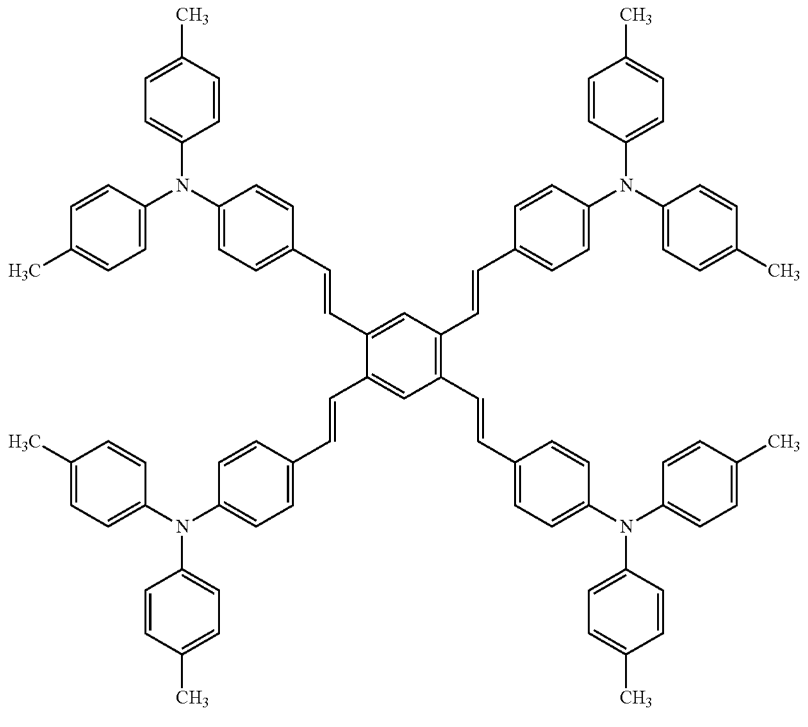

-continued

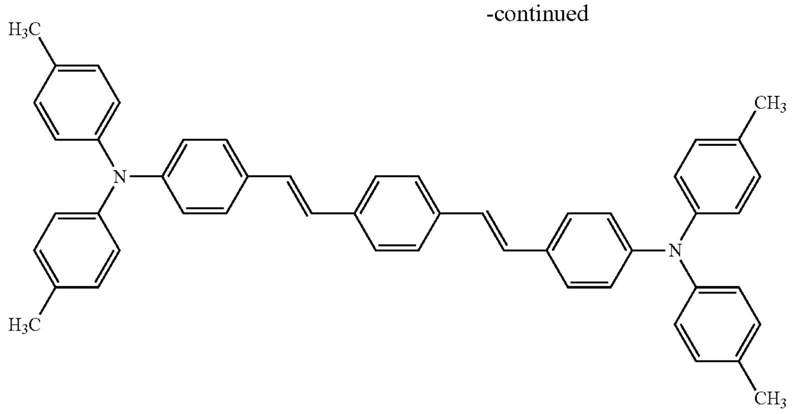

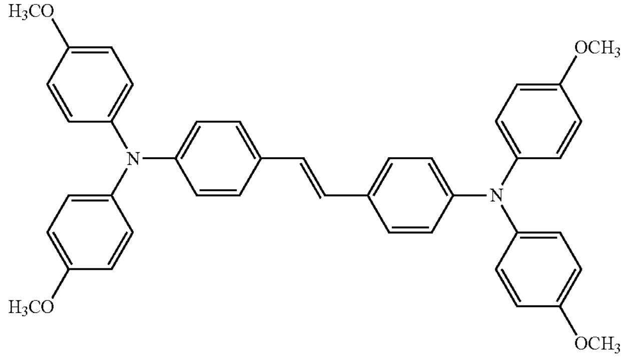

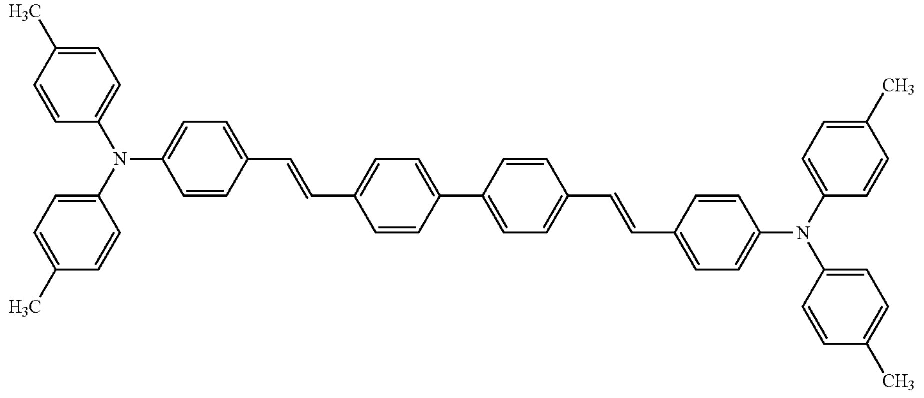

[7] A compound represented by the following general formula (VIII).

General Formula [26]

(VIII)

$$(Ar)_k[A-(Z)_l]_m$$

(In the general formula (VIII), Ar is an aryl group, and when Ar is composed of a plurality of aromatic rings, A may be bonded to a plurality of aromatic rings, and A is represented by the following formula (II). Z is hydrogen, a structure represented by the following general formula (III) or a structure represented by the following formula (IV), which may be the same or different from each other. However, all of Z is not hydrogen, General Formula [27]

(II)

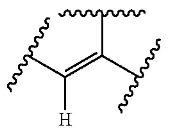

General Formula [28]

(III)

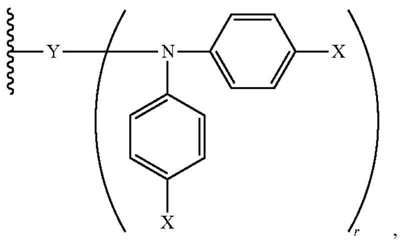

-continued (IV)

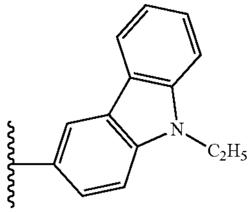

In the structure represented by the above general formula (III), Y is at least one species independently selected from the following groups.

General Formula [29]

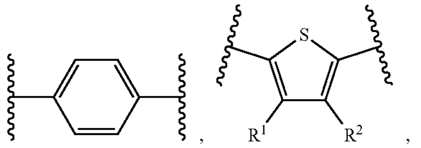

-continued

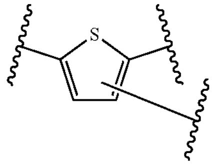

,

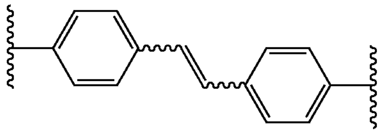

$R^1$ and $R^2$ may be independently hydrogen, alkyl groups, or alkoxy groups, or $R^1$ and $R^2$ may be combined to form a ring having one or two oxygen atoms.

X is an alkyl group, an alkoxy group, an alkylthio group, a monoalkylamino group or a dialkylamino group, which may be independently substituted with halogen, respectively.

k is 0 or 1, l is 2 or 3, m is an integer from 1 to 6, r is 1 or 2, when k is 0, l is 3 and m is 1. All three bonds of A are bound to Z.

Use of compounds other than the following compounds for the manufacture of perovskite solar cells.

General Formula [30]

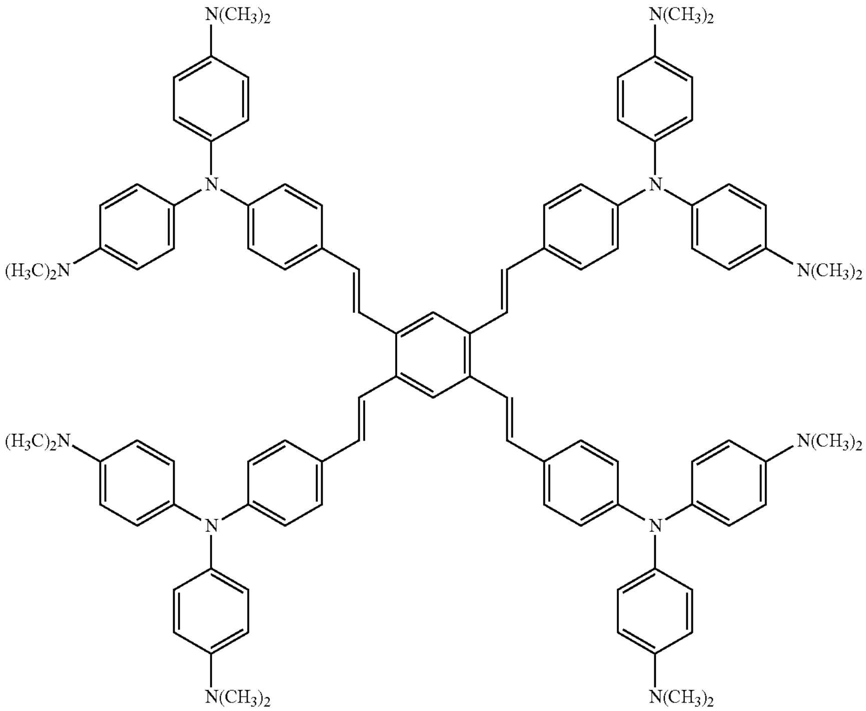

-continued
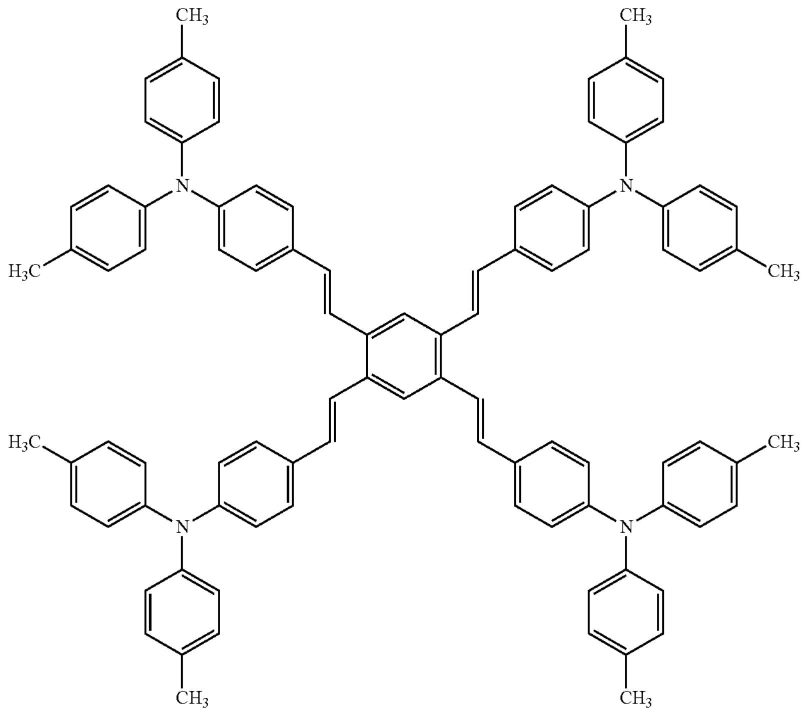
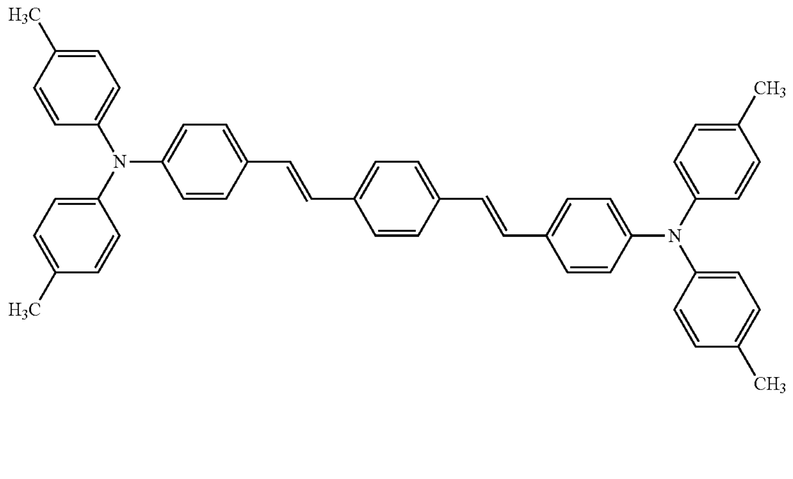
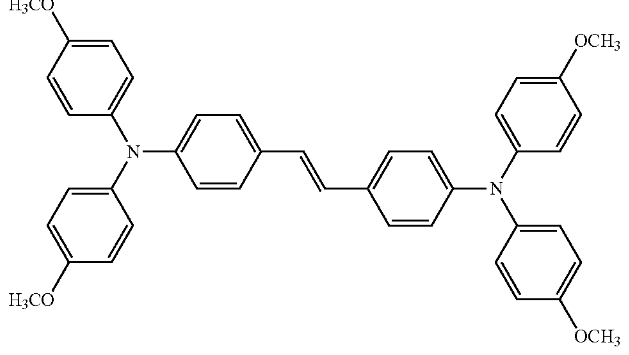

-continued

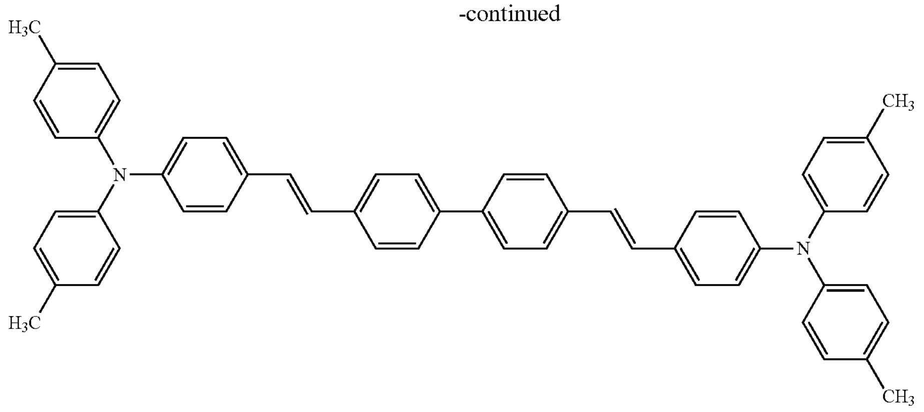

[8] A compound represented by the following general formula (VIII).

General Formula [31]

(VIII)

$$(Ar)_k-[A-(Z)_l]_m$$

(In the general formula (VIII), Ar is an aryl group, and when Ar is composed of a plurality of aromatic rings, A may be bonded to a plurality of aromatic rings, and A is represented by the following formula (II). Z is hydrogen, a structure represented by the following general formula (III) or a structure represented by the following formula (IV), which may be the same or different from each other. However, all of Z is not hydrogen, General Formula [32]

(II)

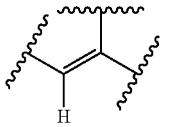

General Formula [33]

(III)

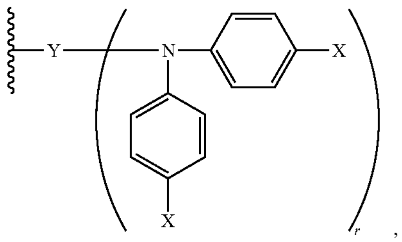

(IV)

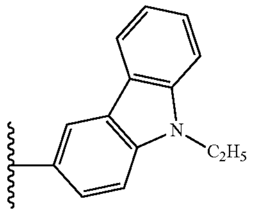

In the structure represented by the above general formula (III), Y is at least one species independently selected from the following groups.

General Formula [34]

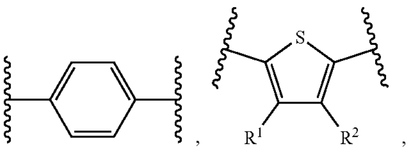

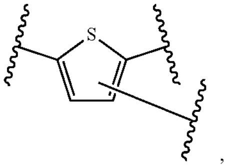

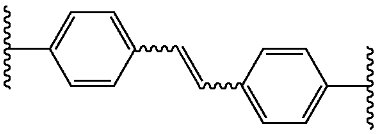

$R^1$ and $R^2$ may be independently hydrogen, alkyl groups, or alkoxy groups, or $R^1$ and $R^2$ may be combined to form a ring having one or two oxygen atoms.

X is an alkyl group, an alkoxy group, an alkylthio group, a monoalkylamino group or a dialkylamino group, which may be independently substituted with halogen, respectively.

k is 0 or 1, l is 2 or 3, m is an integer from 1 to 6, r is 1 or 2, where when k is 0, l is 3 and m is 1.

Yes, all three of A's hands are bound to Z.)

Use of compounds other than the following compounds for the manufacture of hole transport layers in perovskite solar cells.

General Formula [35]
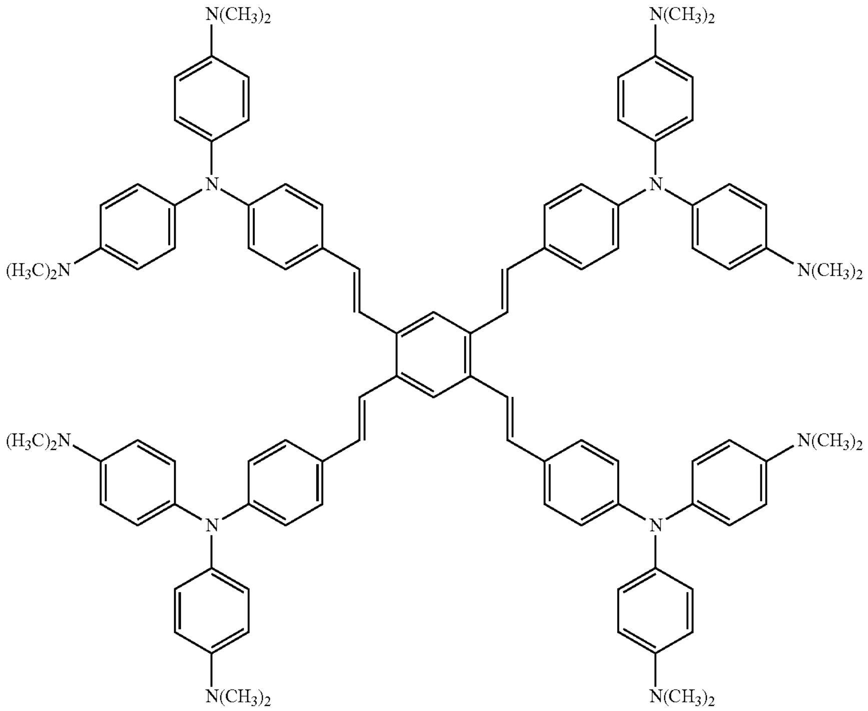
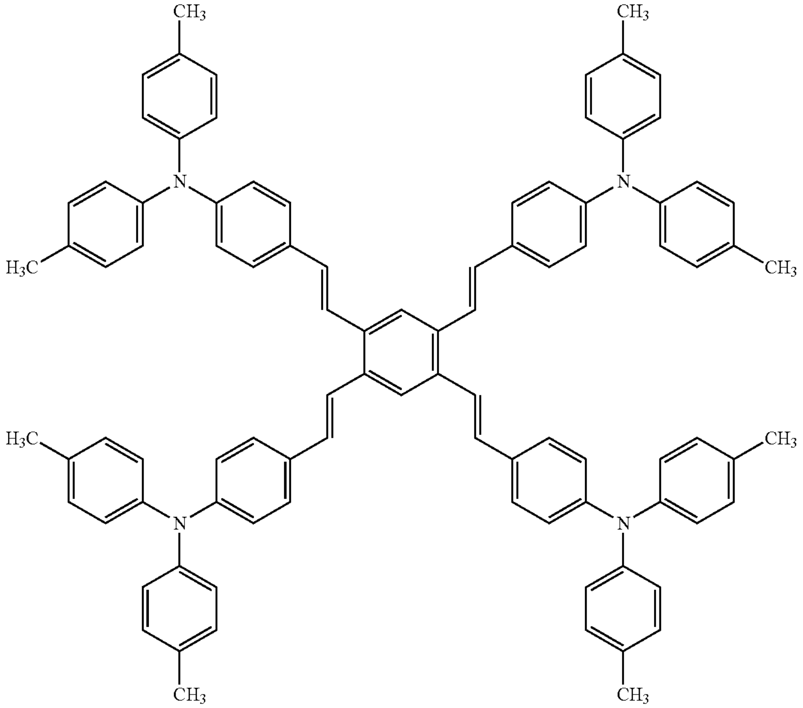

-continued

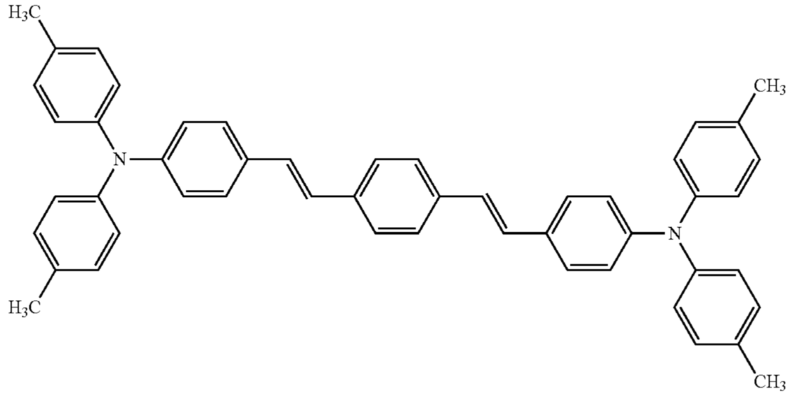

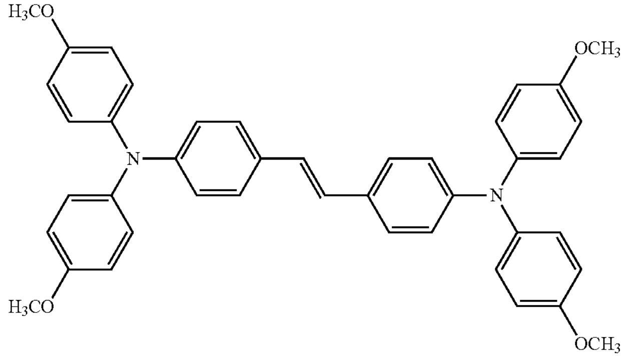

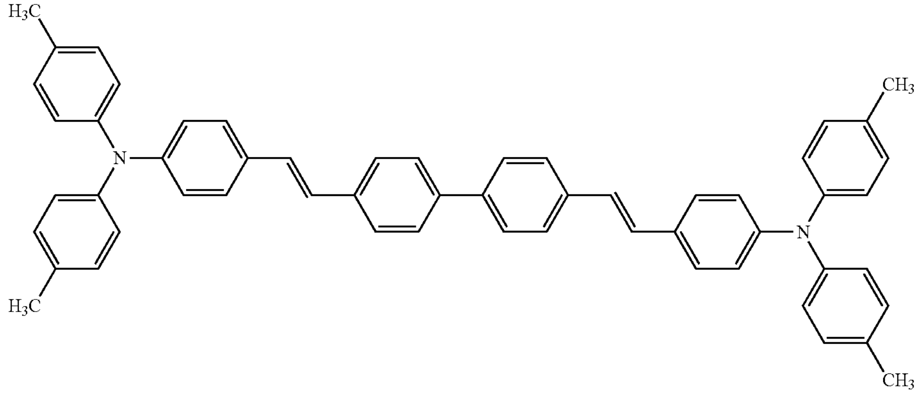

Advantageous Effects of Invention

By the present invention, it is possible to provide a hole transport layer forming composition and a compound contained in a hole transport layer forming composition of a perovskite solar cell which is inexpensive and does not need to be used together with a dopant.

BRIEF DESCRIPTION OF DRAWINGS

FIG. 1 Sectional view showing an example of a normal perovskite solar cell

FIG. 2 Sectional view showing an example of an inverted perovskite solar cell

DESCRIPTION OF EMBODIMENTS

<Compounds>

The first aspect of the present invention relates to the following compounds (also referred to herein as "compounds of the present invention").

The compound of the present invention is a compound represented by the following general formula (I).

General Formula [36]

$$(Ar)_k - [A - (Z)_l]_m \quad (I)$$

(In the general formula (I), Ar is an aryl group, and when Ar is composed of a plurality of aromatic rings, A may be bonded to a plurality of aromatic rings, and A is represented by the following formula (II). Z is hydrogen, a structure represented by the following general formula (III) or a structure represented by the following formula (IV), which may be the same or different from each other. However, all of Z is not hydrogen.

General Formula [37]

(II)

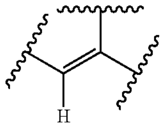

General Formula [38]

(III)

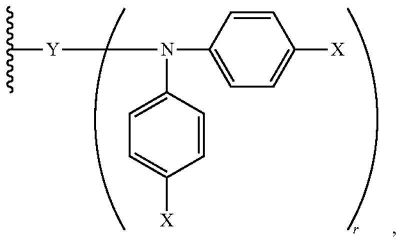

(IV)

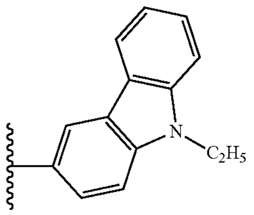

In the structure represented by the above general formula (III), Y is at least one species independently selected from the following groups.

General Formula [39]

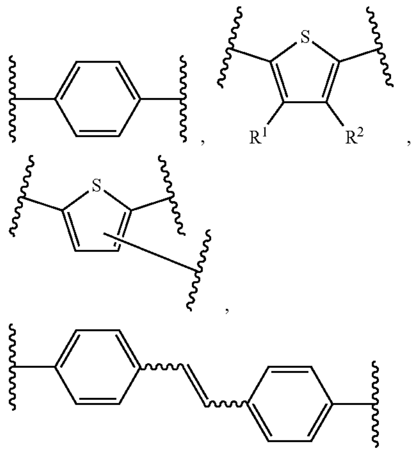

$R^1$ and $R^2$ may be independently hydrogen, alkyl groups, or alkoxy groups, or $R^1$ and $R^2$ may be combined to form a ring having one or two oxygen atoms.

X is an alkyl group, an alkoxy group, an alkylthio group, a monoalkylamino group or a dialkylamino group, which may be independently substituted with halogen, respectively.

k is 0 or 1, l is 2 or 3, m is an integer from 1 to 6, r is 1 or 2, where when k is 0, l is 3 and m is 1.

Yes, all three of A's hands are bound to Z.

However, compounds excluding the following compounds.

General Formula [40]

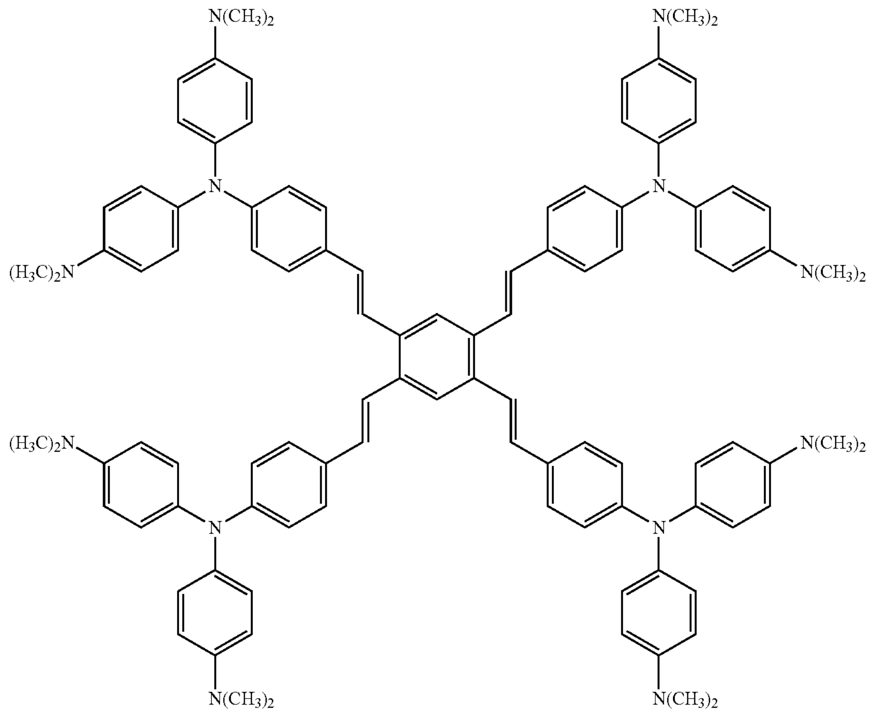

-continued
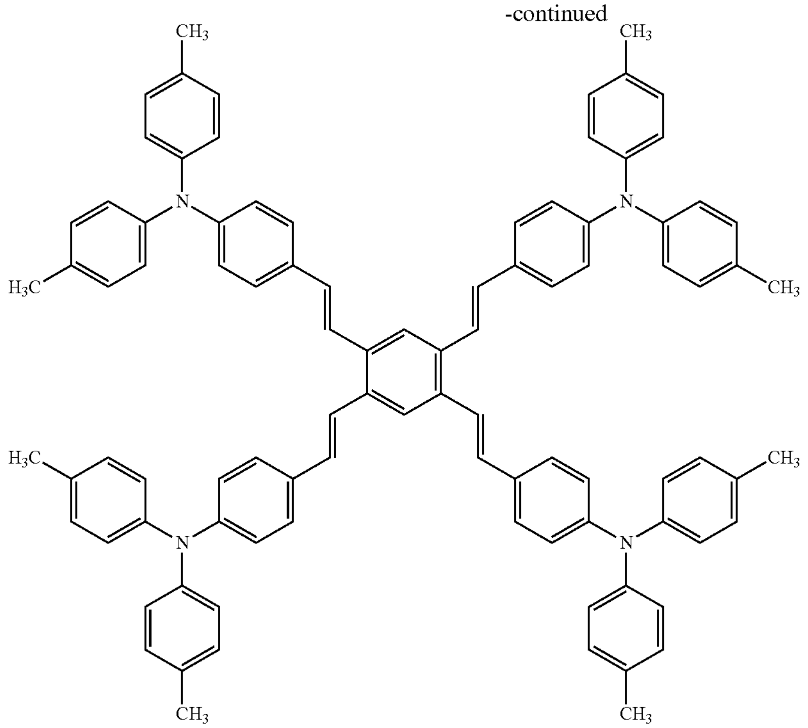
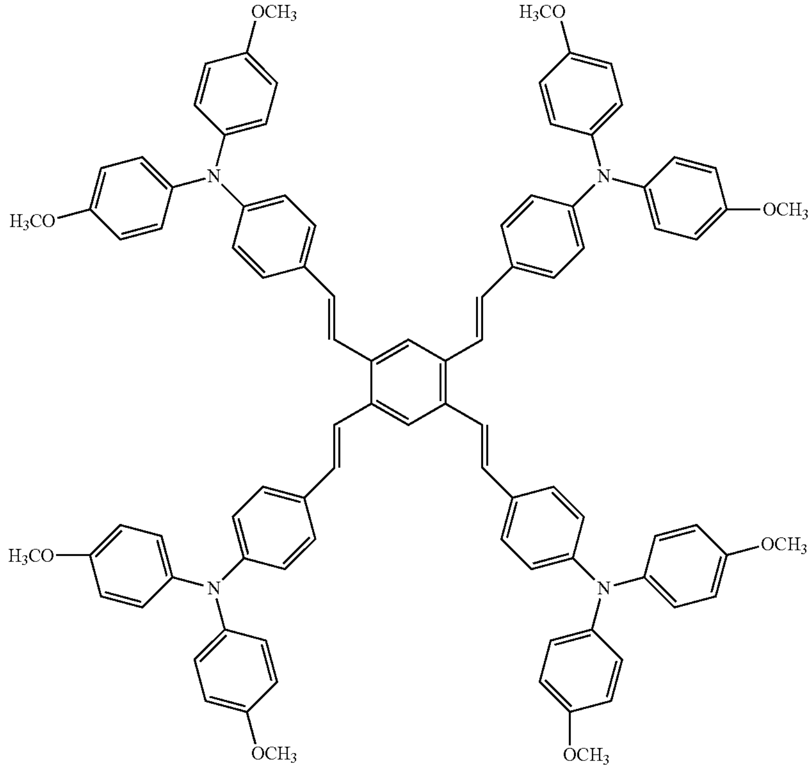 [SMILES: COc1ccc(N(c2ccc(/C=C/c3cc(/C=C/c4ccc(N(c5ccc(OC)cc5)c5ccc(OC)cc5)cc4)c(/C=C/c4ccc(N(c5ccc(OC)cc5)c5ccc(OC)cc5)cc4)cc3/C=C/c3ccc(N(c4ccc(OC)cc4)c4ccc(OC)cc4)cc3)cc2)c2ccc(OC)cc2)cc1]

-continued
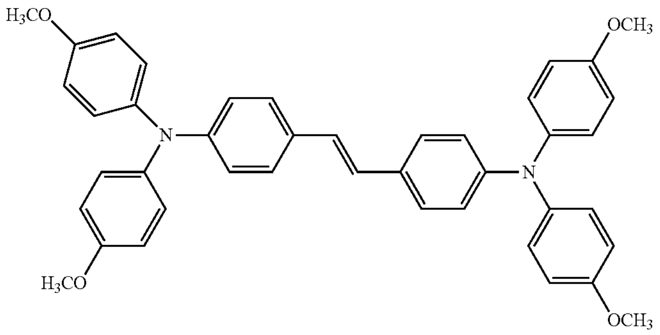
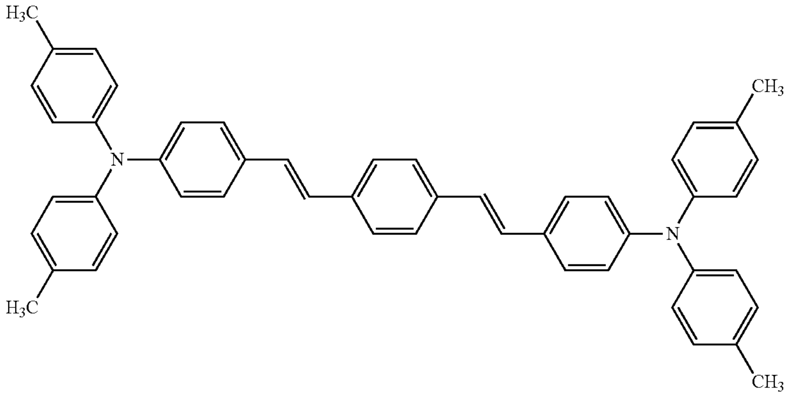
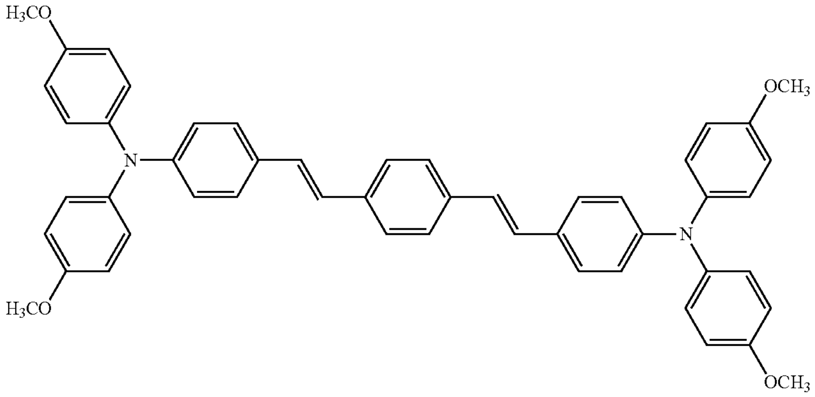
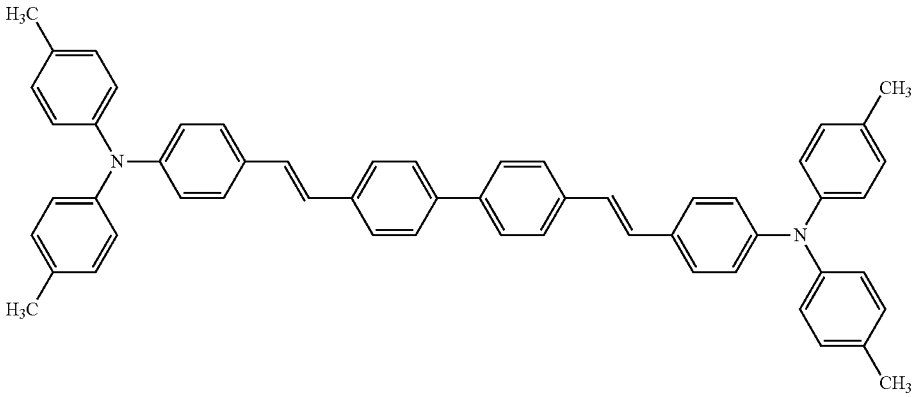
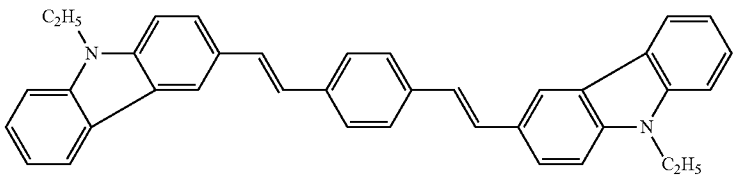

-continued

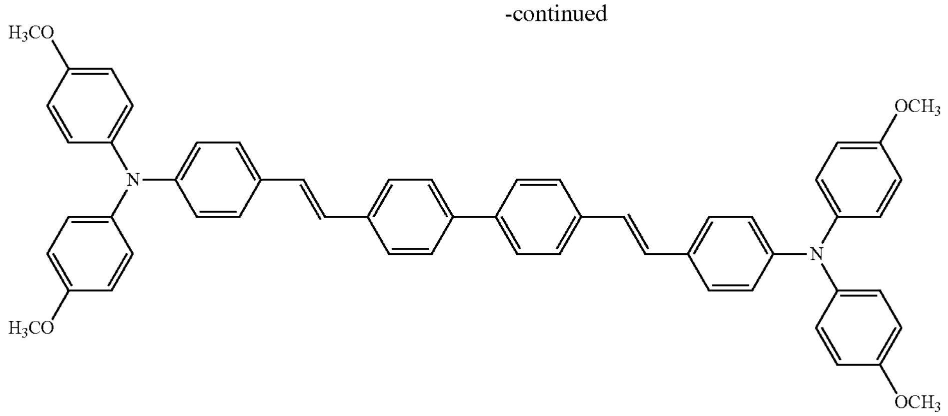

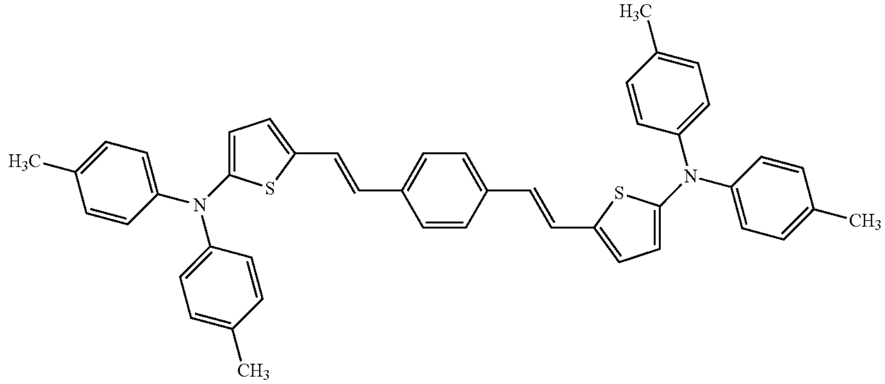

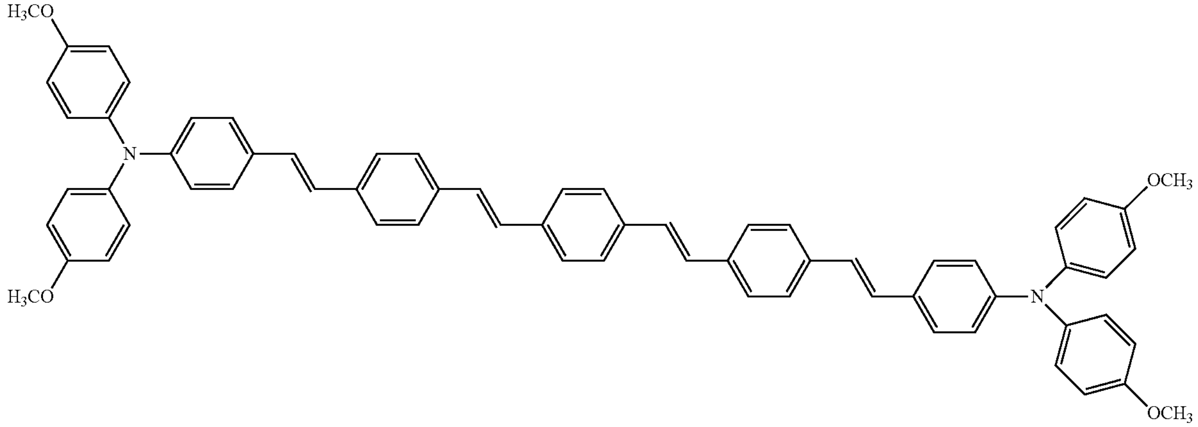

In the above formula, the alkyl group is linear, branched or cyclic, and the number of carbon atoms is preferably 1 to 10, more preferably 1 to 6, and even more preferably 1 to 3. Examples thereof include methyl group, ethyl group, propyl group, isopropyl group, butyl group, isobutyl group, tertiary butyl group, pentyl group, hexyl group, cyclohexyl group, heptyl group, octyl group, nonyl group, decyl group and the like. Methyl group, ethyl group and propyl group are preferable, and methyl group is most preferable.

Examples of the alkyl group of the alkylthio group, monoalkylamino group and dialkylamino group include those similar to the above alkyl group.

The alkoxy group preferably has 1 to 10 carbon atoms, more preferably 1 to 6 carbon atoms, and more preferably 1 to 3 carbon atoms. For example, a methoxy group, an ethoxy group, a propoxy group, a butoxy group, a hexoxy group and the like can be mentioned, with the methoxy group being the most preferable.

Examples of the aryl group include a phenyl group, a naphthyl group, a biphenyl group, a phenanthryl group, an anthryl group, a terphenyl group, a pyrenyl group, a fluorenyl group, a perylenel group and the like. A phenanthryl group and an anthryl group are preferable, and a phenyl group, a biphenyl group and a terphenyl group are preferable.

Examples of the halogen atom include fluorine, chlorine, bromine and iodine, and fluorine is preferable. As for the number of halogen substitutions, it is preferable that the group is substituted with 1 to 2 halogens, and it is more preferable that the group is substituted with 1 halogen.

Y may be a combination of groups included in the above group.

It is preferable that R1 and R2 both form a ring having hydrogen or two oxygen atoms together.

In the compound represented by the general formula (I), k is preferably 1, l is preferably 2, and m is preferably 2 or 4.

When the aryl group consists of a plurality of aromatic rings, it is preferable that A is bonded to all the aromatic rings.

It is an example of Y

General Formula [41]

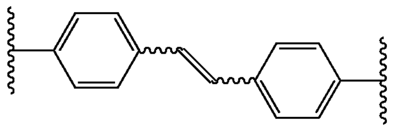

The configuration regarding the double bond may be either the trans form or the cis form below (geometrical isomer).

General Formula [42]

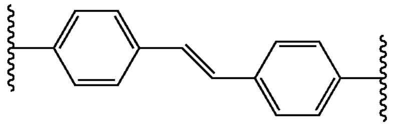

,

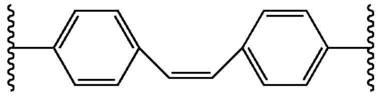

A trans form geometry would be preferable.

X is preferably an alkoxy group or an alkylthio group, more preferably a methoxy group and a methylthio group, and even more preferably a methoxy group.

The compound represented by the general formula (I) is preferably a compound represented by the following general formulas (V), (VI), (VII) or (XXVII).

General Formula [43]

(V)

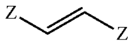

(VI)

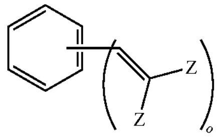

(VII)

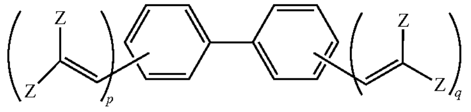

(XXVII)

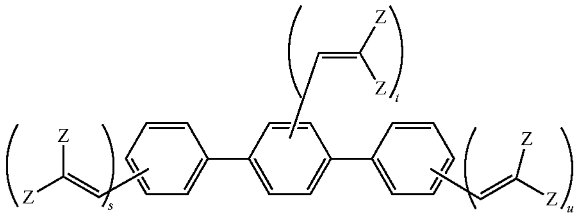

(In the general formula (VI), o is an integer of 1 to 6, in the general formula (VII), p is an integer of 1 to 5, q is an integer of 1 to 5, and in the general formula (XXVII), s is an integer of 1 to 5, t is an integer of 1 to 4, u is an integer of 1 to 5, and the general formula (V) shows that the configuration of the double bond is cis or trans. In any of the general formulas (V), (VI), (VII), and (XXVII), Z is synonymous with the definition in the general formula (I), but is represented by the general formula (V). Each of these compounds has a structure represented by the general formula (III) or a structure represented by the formula (IV) independently.) In the general formula (V), a transformer body is preferable for the configuration regarding the double bond.

Among these, the compound represented by the general formula (I) is a compound represented by the general formula (VI), (VII) or (XXVII), and Z is hydrogen or the following general formula (III). It is preferable that the structure is represented by.

(I) The compound represented by the general formula (I) is a compound represented by the general formula (VI), and Z is hydrogen or a structure represented by the following general formula (III). The two Zs bonded to one carbon have a structure of hydrogen on one side and the following general formula (III) on the other side.

General Formula [44]

(III)

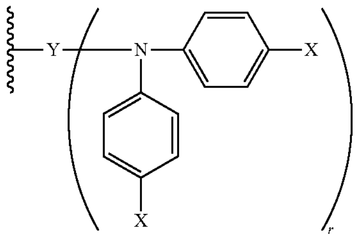

In the structure represented by the general formula (III), Y has the following structure.

General Formula [45]

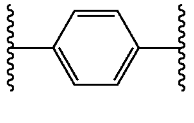

X is independently each of —OR, —SR, or —$NR_2$, where $R=C_nH_{2n+1}$.

A compound in which n=an integer of 1 to 10, o is 2, and r is 1.

(Ii) A compound represented by the general formula (VI), in which Z is hydrogen or a structure represented by the following general formula (III), and one of the two Zs bonded to one carbon is one. Hydrogen, the other is the structure of the following general formula (III), General Formula [46]

(III)

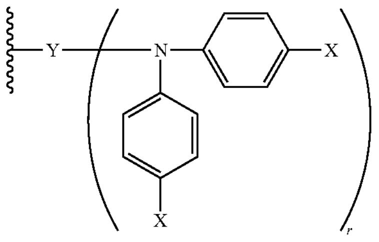

In the structure represented by the general formula (III), Y is a combination of one selected from the following (A) and (B).

Gneral Formula [47]

(A)

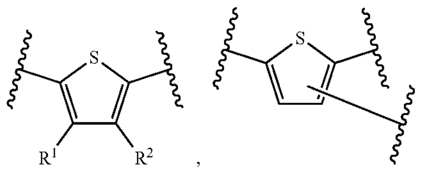

, (B)

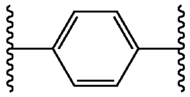

,

X is each independently —OR, —SR, or —$NR_2$, where $R=C_nH_{2n+1}$, and $R^1$ and $R^2$ are both hydrogen or a ring having two oxygen atoms. A compound in which n=an integer of 1 to 10, o is 2, and r is 1 or 2.

(Iii) A compound represented by the general formula (VI), in which Z is hydrogen or a structure represented by the following general formula (III), and one of the two Zs bonded to one carbon is one. Hydrogen, the other is the structure of the following general formula (III), General Formula[48]

(III)

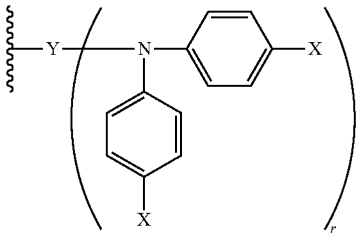

In the structure represented by the general formula (III), Y has the following structure.

General Formula[49]

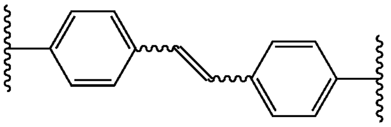

X is independently —OR, —SR, or —$NR_2$, where $R=C_nH_{2n+1}$, n=an integer of 1-10, o is 2, and r is 1 or 2.

(Iv) A compound represented by the general formula (XXVII) in which Z is hydrogen or a structure represented by the following general formula (III), and one of the two Zs bonded to one carbon is one. Hydrogen, the other is the structure of the following general formula (III), General Formula[50]

(III)

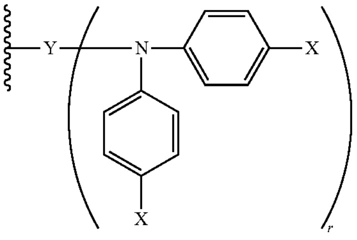

In the structure represented by the general formula (III), Y has the following structure.

General Formula[51]

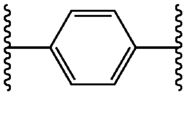

X is independently —OR, —SR, or —$NR_2$, where $R=C_nH_{2n+1}$, an integer of n=1-10, s is 1, and t is 2, U is 1 and r is 1.

At least one compound selected from the group consisting of (i) to (iV) is more preferable.

The compound of the general formula (I) can be synthesized by a method such as coupling or dehalogenation commonly used in synthetic organic chemistry. It will be described in more detail in the section of Examples below. Since it is not necessary to use expensive raw materials, the manufacturing cost can be suppressed.

<Hole Transport Layer Forming Composition>

A second aspect of the present invention is the following hole transport layer forming composition for a perovskite solar cell (in the present specification, the "composition of the present invention" or "hole transport layer for a perovskite solar cell of the present invention". Also referred to as "forming composition").

The hole transport layer forming composition for a perovskite solar cell of the present invention is a hole transport layer forming composition for a perovskite solar cell containing a compound represented by the following general formula (VIII) and a solvent and containing no dopant.

General Formula[52]

$$(Ar)_k[A(Z)_l]_m \qquad \text{(VIII)}$$

(In the general formula (VIII), Ar is an aryl group, and when Ar is composed of a plurality of aromatic rings, A may be bonded to a plurality of aromatic rings, and A is represented by the following formula (II). Z is hydrogen, a structure represented by the following general formula (III) or a structure represented by the following formula (IV), which may be the same or different from each other. However, all of Z is not hydrogen.

General Formula [53]

(II)

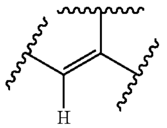

General Formula [54]

(III)

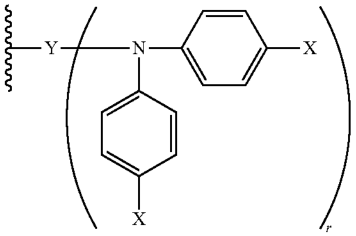

(IV)

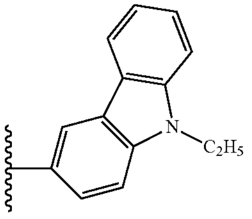

In the structure represented by the above general formula (III), Y is at least one species independently selected from the following groups.

General Formula[55]

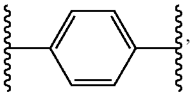,

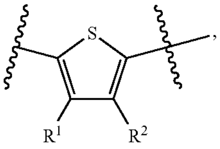,

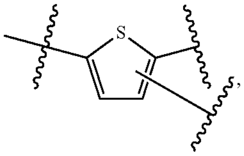,

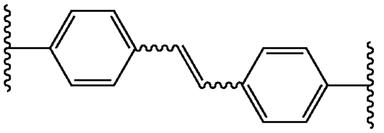

$R^1$ and $R^2$ may be independently hydrogen, alkyl groups, or alkoxy groups, or $R^1$ and $R^2$ may be combined to form a ring having one or two oxygen atoms.

X is an alkyl group, an alkoxy group, an alkylthio group, a monoalkylamino group or a dialkylamino group, which may be independently substituted with halogen, respectively.

k is 0 or 1, l is 2 or 3, m is an integer from 1 to 6, r is 1 or 2, where when k is 0, l is 3 and m is 1.

Yes, all three of A's hands are bound to Z.

However, the compound represented by the general formula (VIII) is a hole transport layer forming composition for a perovskite solar cell excluding the following compounds.

General Formula [56]
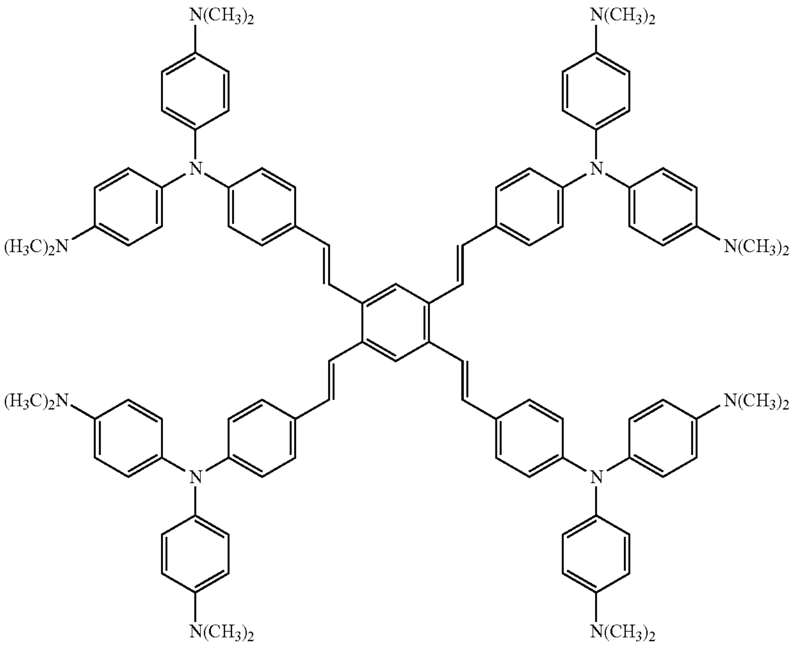
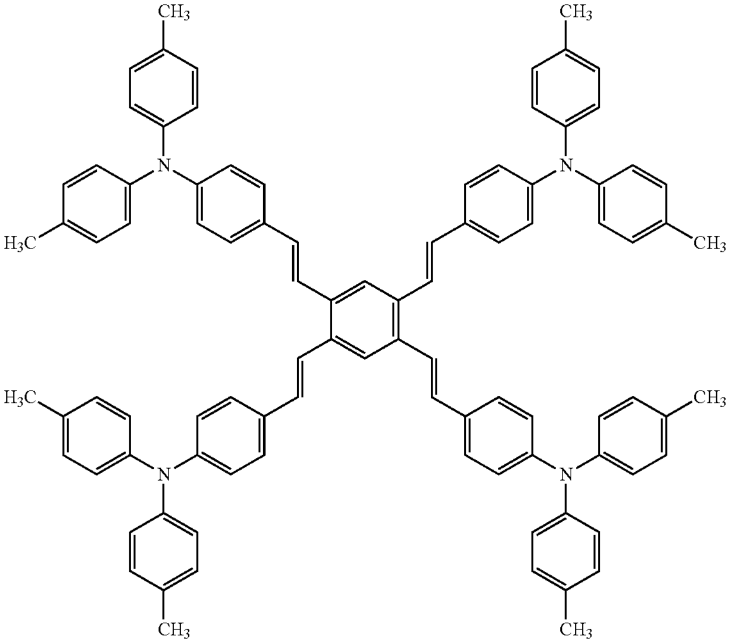
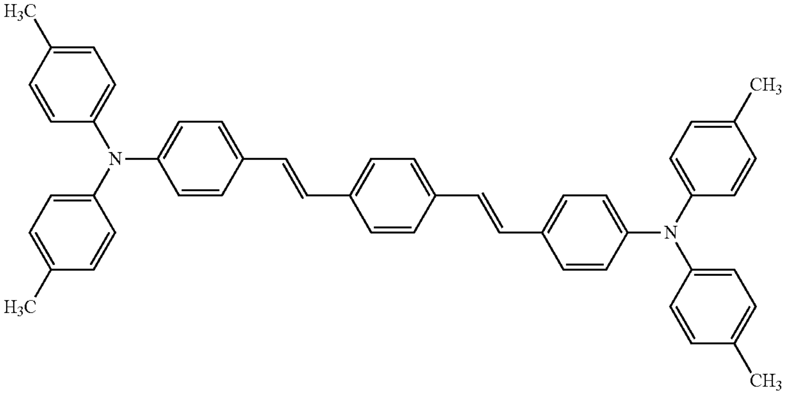

-continued

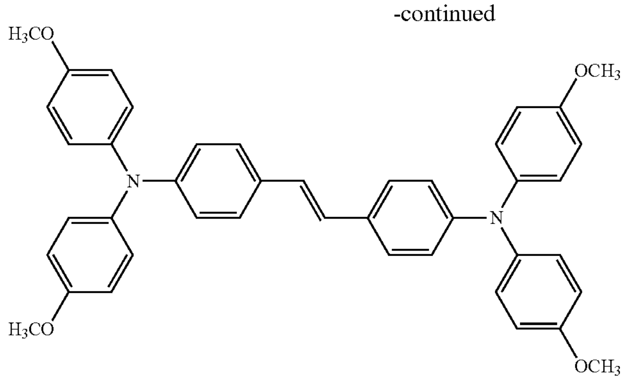

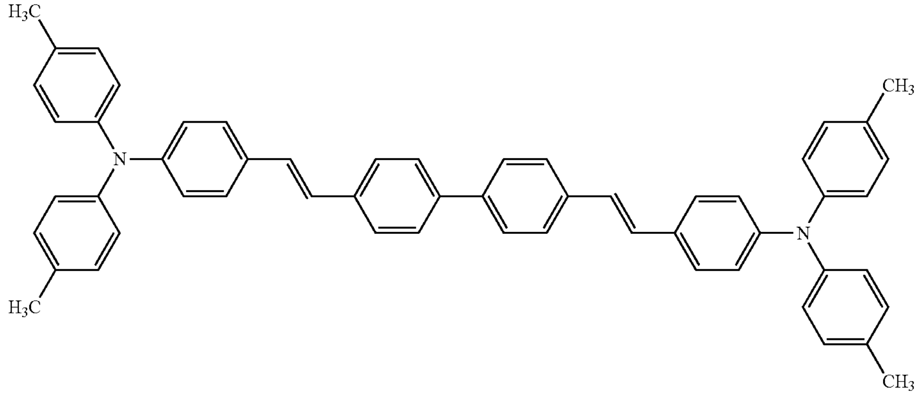

In the above formula, the alkyl group is linear, branched or cyclic, and the number of carbon atoms is preferably 1 to 10, more preferably 1 to 6, and even more preferably 1 to 3. Examples thereof include methyl group, ethyl group, propyl group, isopropyl group, butyl group, isobutyl group, tertiary butyl group, pentyl group, hexyl group, cyclohexyl group, heptyl group, octyl group, nonyl group, decyl group and the like. Methyl group, ethyl group and propyl group are preferable, and methyl group is most preferable.

Examples of the alkyl group of the alkylthio group, monoalkylamino group and dialkylamino group include those similar to the above alkyl group.

The alkoxy group preferably has 1 to 10 carbon atoms, more preferably 1 to 6 carbon atoms, and more preferably 1 to 3 carbon atoms. For example, a methoxy group, an ethoxy group, a propoxy group, a butoxy group, a hexoxy group and the like can be mentioned, with the methoxy group being the most preferable.

Examples of the aryl group include a phenyl group, a naphthyl group, a biphenyl group, a phenanthryl group, an anthryl group, a terphenyl group, a pyrenyl group, a fluorenyl group, a perylenel group and the like. A phenanthryl group and an anthryl group are preferable, and a phenyl group, a biphenyl group and a terphenyl group are preferable.

Examples of the halogen atom include fluorine, chlorine, bromine and iodine, and fluorine is preferable. As for the number of halogen substitutions, it is preferable that the group is substituted with 1 to 2 halogens, and it is more preferable that the group is substituted with 1 halogen.

Y may be a combination of groups included in the above group.

It is preferable that R1 and R2 both form a ring having hydrogen or two oxygen atoms together.

In the compound represented by the general formula (VIII), k is preferably 1, l is preferably 2, and m is preferably 2 or 4.

When the aryl group consists of a plurality of aromatic rings, it is preferable that A is bonded to all the aromatic rings.

It is an example of Y

General Formula[57]

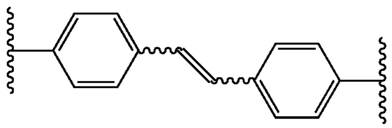

Regarding, the configuration regarding the double bond may be either the following cis-form or trans-form, General Formula[58]

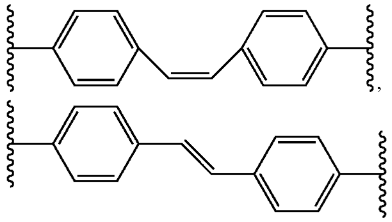

A trans form is preferable.

As X, an alkoxy group and an alkylthio group are preferable, a methoxy group and a methylthio group are more preferable, and a methoxy group is further preferable.

The compound represented by the general formula (VIII) is preferably a compound represented by the following general formulas (V), (VI), (VII) or (XXVII).

General Formula[59]

(V)

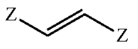

(VI)

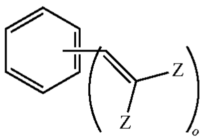

(VII)

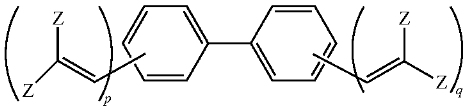

(XXVII)

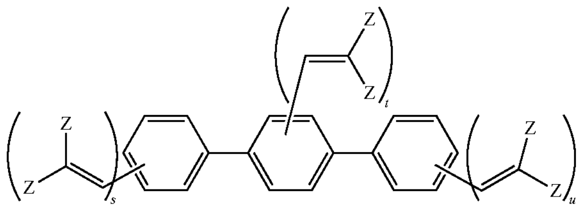

(In the general formula (VI), o is an integer of 1 to 6, in the general formula (VII), p is an integer of 1 to 5, q is an integer of 1 to 5, and in the general formula (XXVII), s is an integer of 1 to 5, t is an integer of 1 to 4, u is an integer of 1 to 5, and the general formula (V) shows that the configuration of the double bond is cis or trans. In any of the general formulas (V), (VI), (VII), and (XXVII), Z is synonymous with the definition in the general formula (VIII), but is represented by the general formula (V). In each of these compounds, the structure is independently represented by the general formula (III) or the structure represented by the formula (IV).) In the general formula (V), a transformer body is preferable for the configuration regarding the double bond.

Among these, the compound represented by the general formula (VIII) is a compound represented by the general formula (VI), (VII) or (XXVII), and Z is hydrogen or the following general formula (III). It is preferable that the structure is represented by.

(I) The compound represented by the general formula (VIII) is a compound represented by the general formula (VI), and Z is hydrogen or a structure represented by the following general formula (III). The two Zs bonded to one carbon have a structure of hydrogen on one side and the following general formula (III) on the other side.

General Formula[60]

(III)

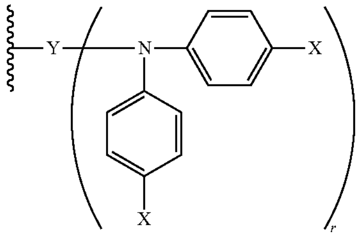

In the structure represented by the general formula (III), Y has the following structure.

General Formula[61]

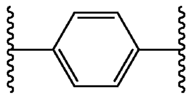

X is independently —OR, —SR, or —$NR_2$, where $R=C_nH_{2n+1}$, an integer of n=1-10, o is 2, and r is 1.

(Ii) A compound represented by the general formula (VI), in which Z is hydrogen or a structure represented by the following general formula (III), and one of the two Zs bonded to one carbon is one. Hydrogen, the other is the structure of the following general formula (III), General Formula[62]

(III)

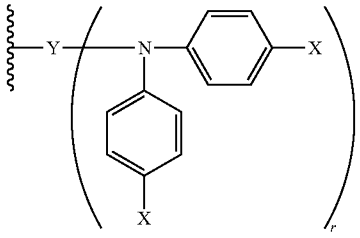

In the structure represented by the general formula (III), Y is a combination of one selected from the following (A) and (B).

General Formula[63]

(A)

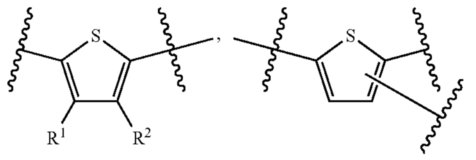

(B)

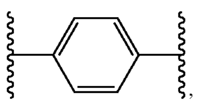

X is each independently —OR, —SR, or —$NR_2$, where R=CnH2n+1, and R1 and R2 are both hydrogen or a ring having two oxygen atoms. A compound in which n=an integer of 1 to 10, o is 2, and r is 1 or 2.

(Iii) A compound represented by the general formula (VI), in which Z is hydrogen or a structure represented by the following general formula (III), and one of the two Zs bonded to one carbon is one. Hydrogen, the other is the structure of the following general formula (III), General Formula[64]

(III)

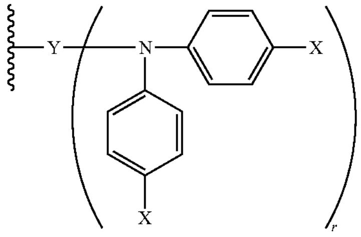

In the structure represented by the general formula (III), Y has the following structure.

General Formula[65]

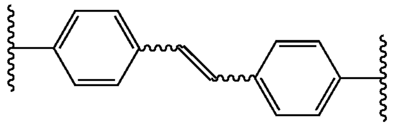

X is independently —OR, —SR, or —$NR_2$, where $R=C_nH_{2n+1}$, n=an integer of 1-10, o is 2, and r is 1 or 2.

(Iv) A compound represented by the general formula (XXVII) in which Z is hydrogen or a structure represented by the following general formula (III), and one of the two Zs bonded to one carbon is one. Hydrogen, the other is the structure of the following general formula (III), General Formula [66]

(III)

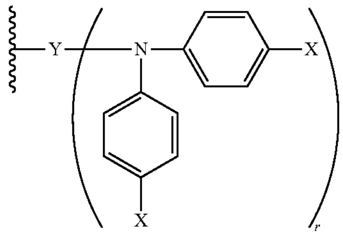

In the structure represented by the general formula (III), Y has the following structure.

General Formula [67]

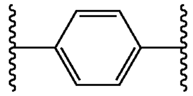

X is independently —OR, —SR, or —$NR_2$, where $R=C_nH_{2n+1}$, an integer of n=1-10, s is 1, and t is 2, U is 1 and r is 1.

At least one compound selected from the group consisting of (i) to (iv) is more preferable.

Specific examples of the compound represented by the general formula (VIII) include General Formula [68]

(IX)

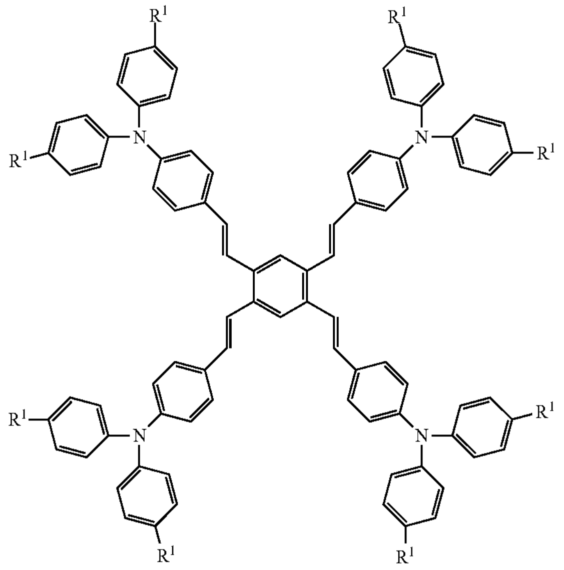

-continued
(X)
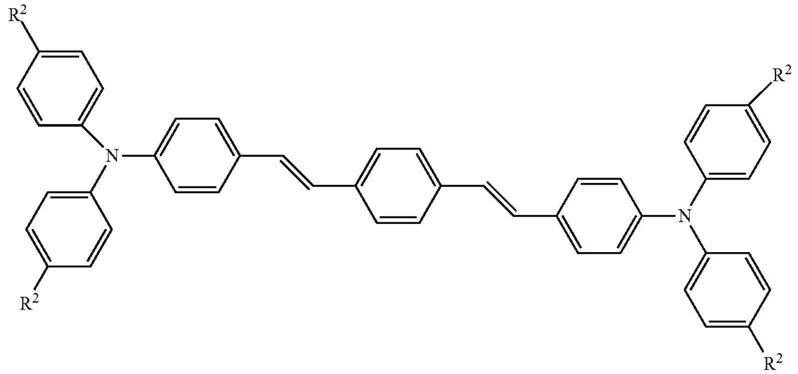
(XI)
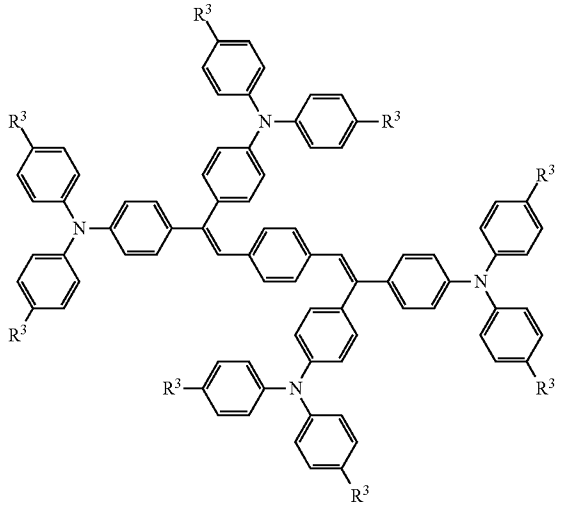
(XII)
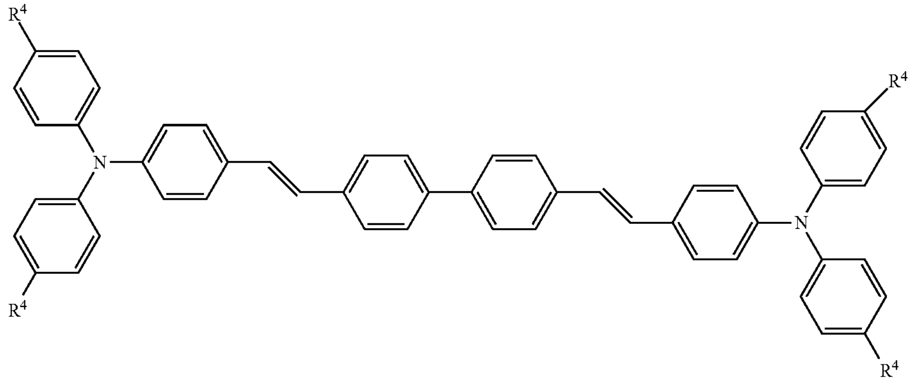
(XIII)
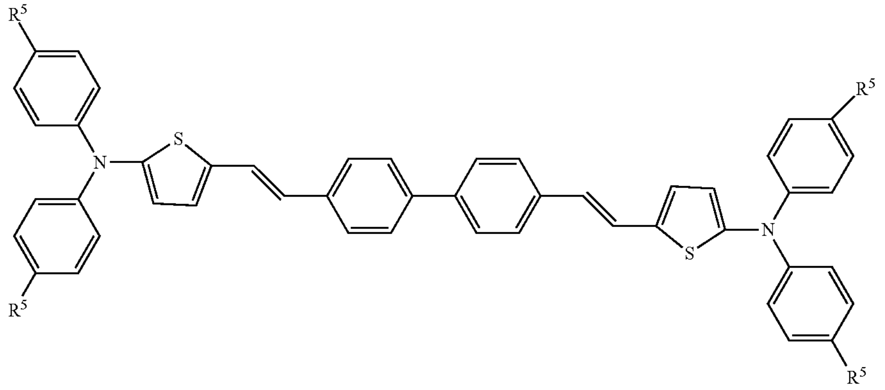

-continued
(XIV)
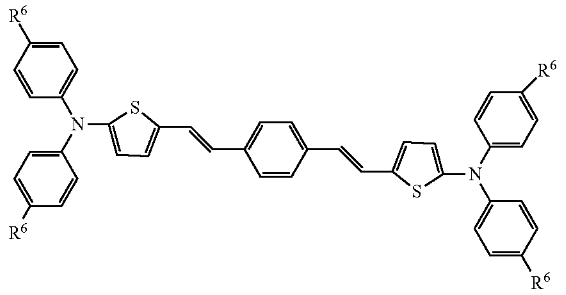
(XVI)
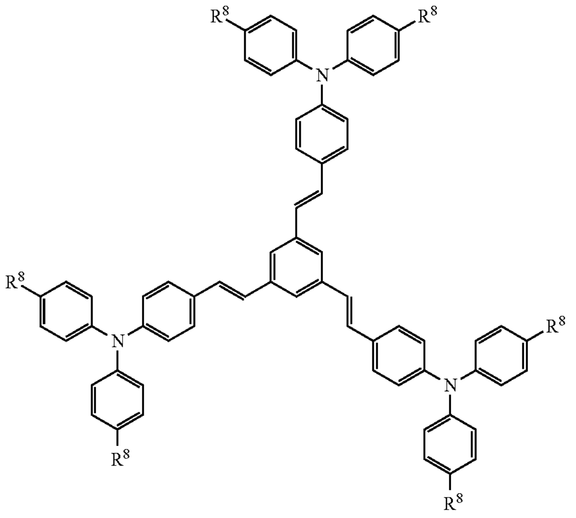
(XVII)
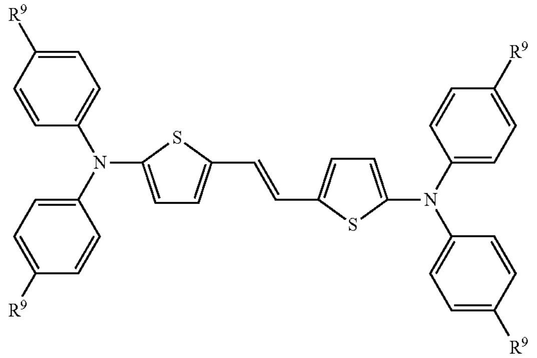
(XVIII)
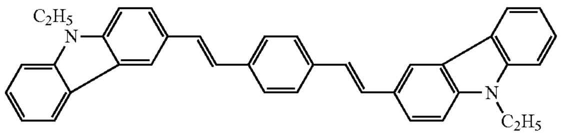
(XIX)
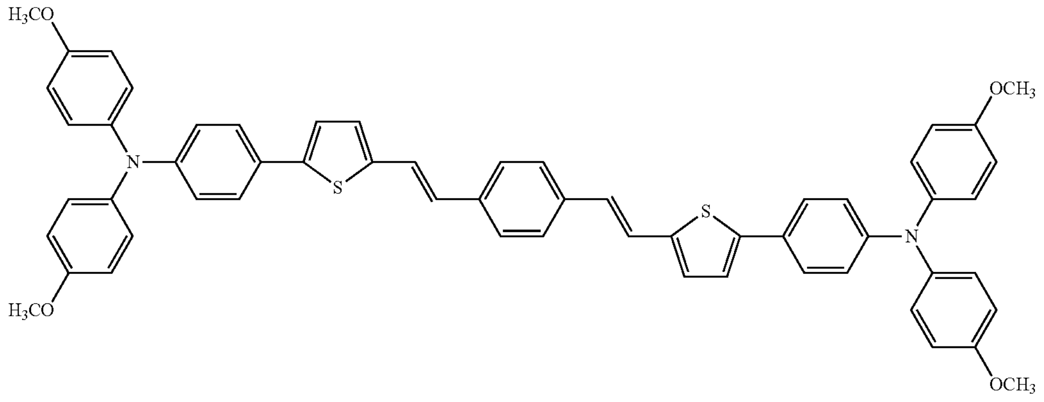

-continued
(XX)
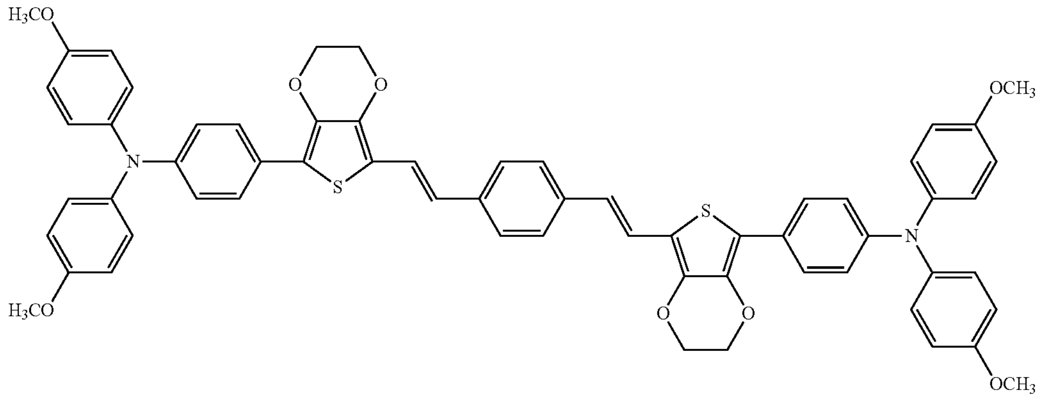
(XXI)
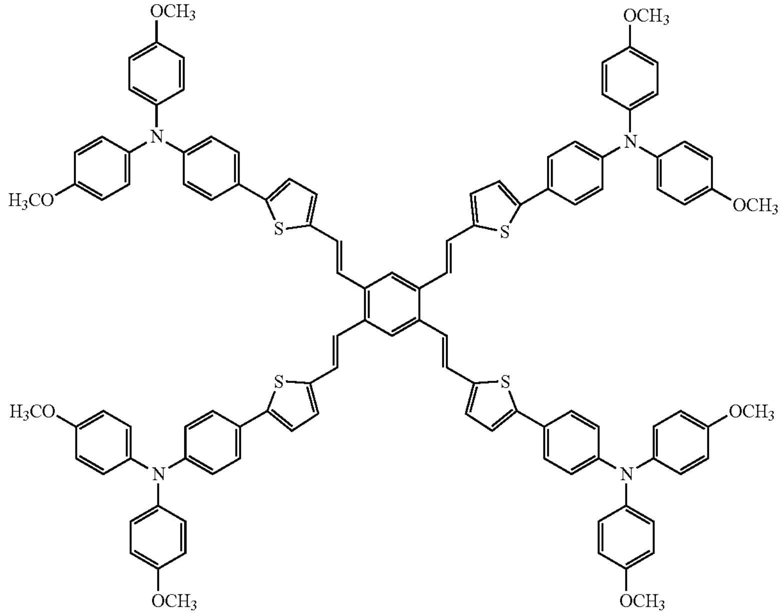
(XXII)
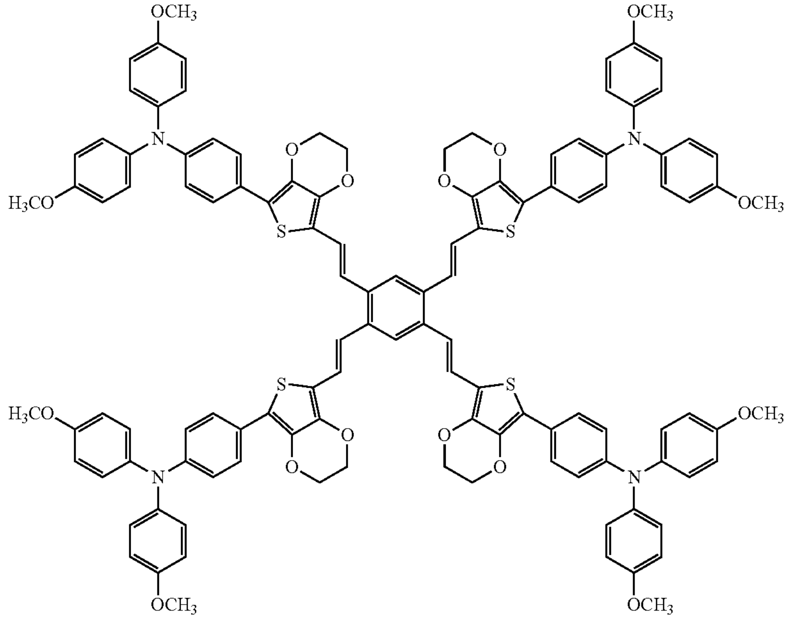

-continued
(XXIII)
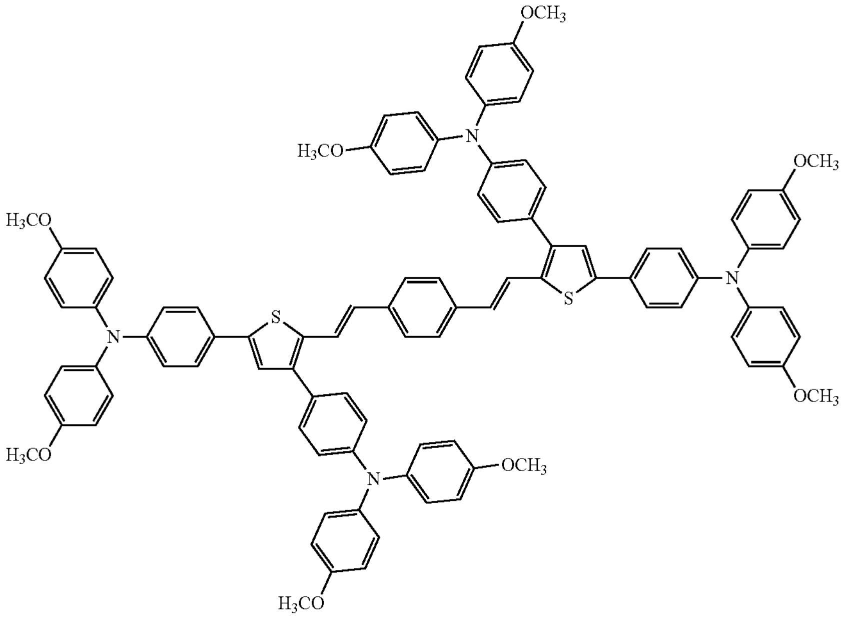
(XXIV)
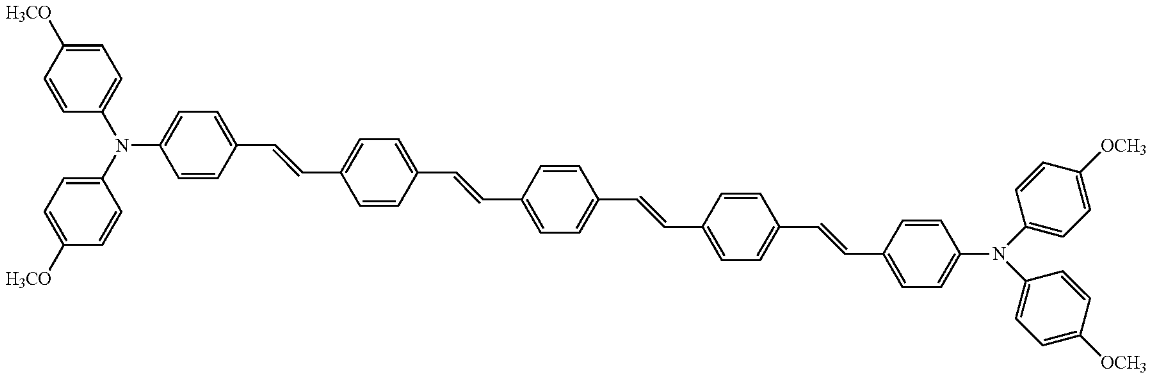 [SMILES: COc1ccc(N(c2ccc(/C=C/c3ccc(/C=C/c4ccc(/C=C/c5ccc(/C=C/c6ccc(N(c7ccc(OC)cc7)c7ccc(OC)cc7)cc6)cc5)cc4)cc3)cc2)c2ccc(OC)cc2)cc1]
(XXV)
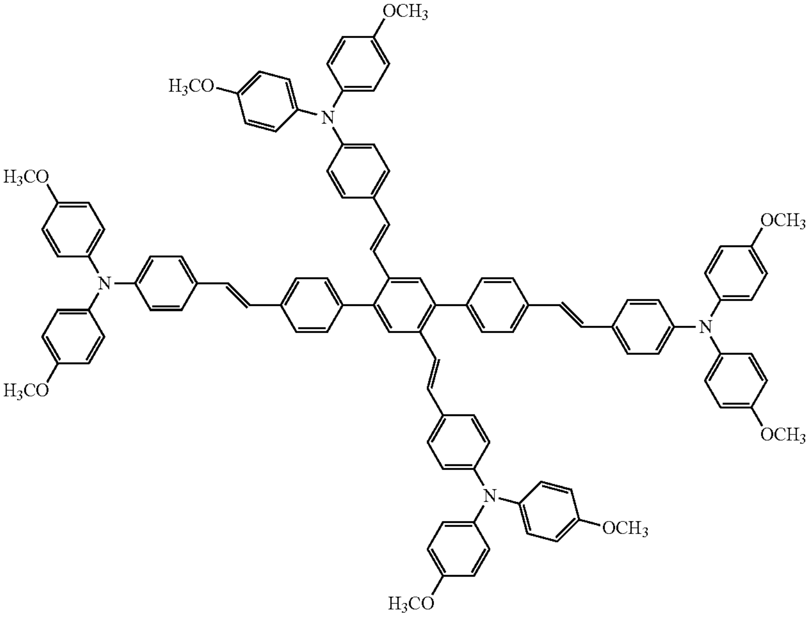

-continued (XXVI)

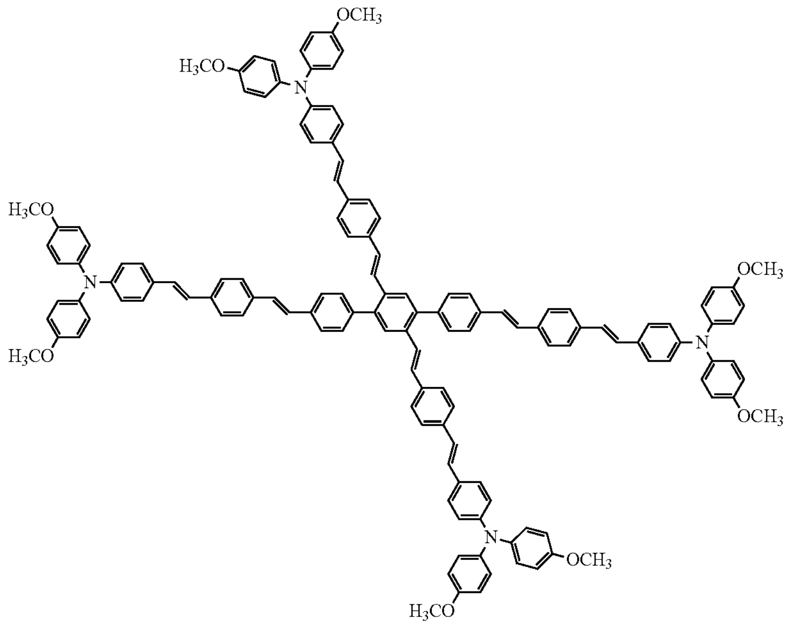

(In the general formula (IX), $R^1$ is the same as each other and is a methoxy group, a methylthio group or a hexoxy group, and in the formula (X), $R^2$ is the same as each other and is a methoxy group, a methylthio group or a dimethyl group. It is an amino group or a hexoxy group, and in formula (XI), $R^3$ is the same as each other and is a methoxy group or a methylthio group, and in formula (XII), $R^4$ is the same as each other and is a methoxy group. For the methylthio group, in formula (XIII), $R^5$ is identical to each other and is a methoxy group or a methyl group, and in formula (XIV), $R^6$ is identical to each other and is a methoxy group, formula. In (XVI), $R^8$ are identical to each other and are methoxy groups, and in formula (XVII), $R^9$ are identical to each other and are methoxy groups or methyl groups.)

Among these, from the viewpoint of photoelectric conversion efficiency, a compound of the formula (IX) in which R' is the same methoxy group or a methylthio group, and a compound of the formula (X) in which $R^2$ is the same methoxy group or a methylthio group. Compound of formula (XI) in which $R^3$ is the same methoxy group or methylthio group, compound of formula (XII) in which $R^4$ is the same methoxy group or methylthio group, compound of formula (XIX). Compounds of formula (XX), formula (XXI), formula (XXIII), formula (XXIV), formula (XXV) and compounds of formula (XXVI) are preferred.

A compound of formula (IX) in which R' is the same methoxy group or methylthio group, a compound of formula (X) in which $R^2$ is the same methoxy group or methylthio group, a compound of formula (XXIV), a compound of formula (XX). Formula (XXIII), Formula (XXIV) and Formula (XXV) are more preferred.

Compounds of formula (IX) in which R' is the same methoxy group as each other, compounds of formula (X) in which $R^2$ is the same methoxy group or methylthio group, compounds of formula (XIX), compounds of formula (XX) and Compounds of formula (XXIV) are more preferred.

Compounds of formula (IX) in which R' is the same methoxy group as each other, compounds of formula (X) in which $R^2$ is the same methoxy group or methylthio group, and compounds of formula (XXIV) have particularly high photoelectric conversion efficiency. It is represented by the following equations, respectively.

General Formula [69]
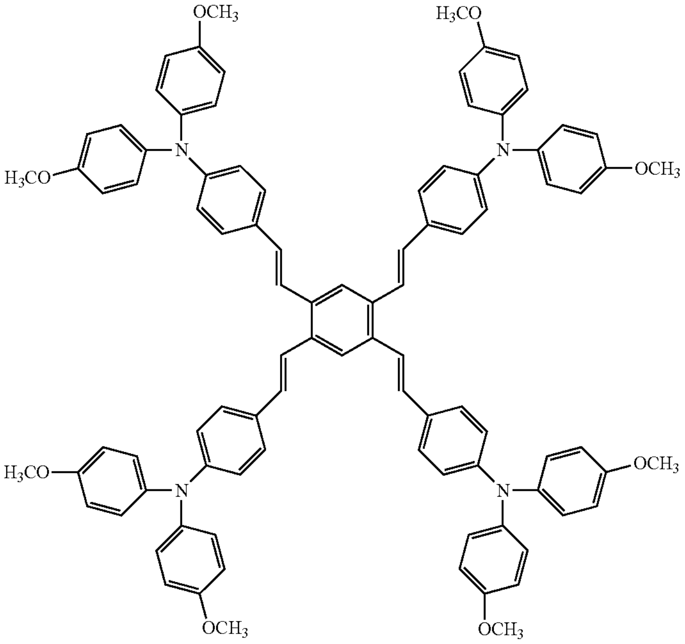
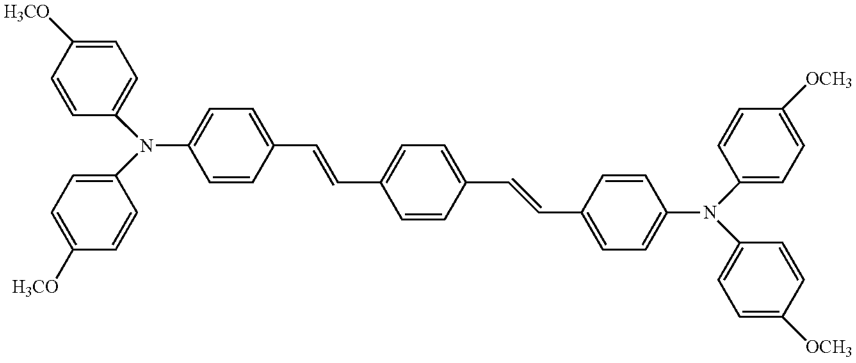
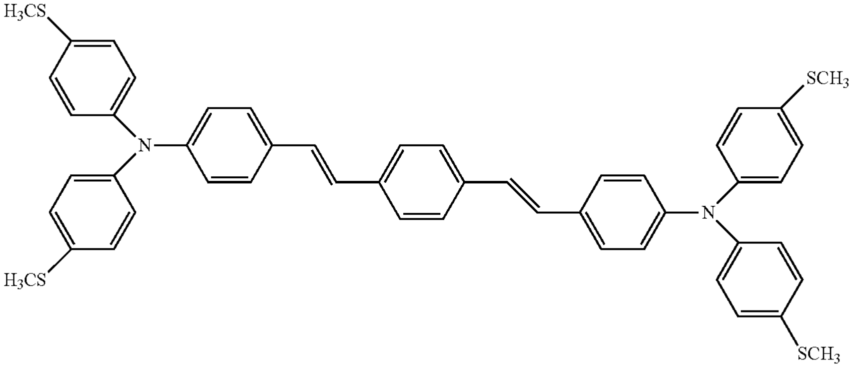

-continued

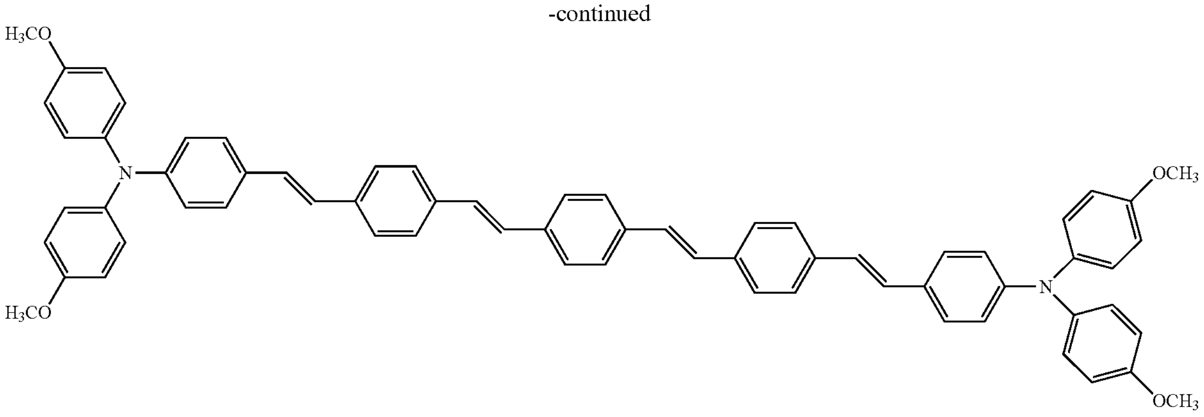

The compound of the general formula (VIII) contained in the composition of the present invention can be synthesized by a method such as coupling or dehalogenation commonly used in synthetic organic chemistry. It will be described in more detail in the section of Examples below. Since it is not necessary to use expensive raw materials, the manufacturing cost can be suppressed.

The composition of the present invention contains a solvent. The solvent is not particularly limited as long as it can dissolve the compound of the general formula (VII), and examples thereof include a hydrocarbon solvent, a halogenated hydrocarbon solvent, an aromatic solvent, and dimethyl sulfoxide. Halogenated hydrocarbon solvent is preferable, 1,1,2,2-tetrachloroethane, chloroform and chlorobenzene are more preferable.

The compositions of the present invention do not contain any dopants. Examples of the dopant include p-type dopants, such as Lithium (Fluorosulfonyl)(trifluoromethanesulfonyl) imide, Lithium Bis(trifluoromethanesulfonyl)imide, and Tris[4-tert-butyl-2-(1H-pyrazol-1-yl)pyridine] cobalt(II) Bis (trifluoromethanesulfonyl)imide and some more related compounds.

The composition of the present invention can be produced by dissolving or mixing the compound of the general formula (VIII) and other optional components in the solvent.

<Perovskite Solar Cells>

The hole transport layer forming composition is used for the hole transport layer of a perovskite solar cell.

As shown in FIGS. 1 and 2, a perovskite solar cell usually includes a substrate 3, a first electrode 4, a second electrode 8, a perovskite layer 6, a hole transport layer 7, and an electron transport layer 5.

In the perovskite solar cell, as shown in FIG. 1, the first electrode is a negative electrode and the second electrode is a positive electrode, and the substrate 3, the first electrode 4, the electron transport layer 5, the perovskite layer 6, and the hole transport A normal type 1 in which the layer 7 and the second electrode 8 are laminated in this order, and as shown in FIG. 2, the first electrode is a positive electrode and the second electrode is a negative electrode, and the substrate 3 and the first electrode There is an inverted type 2 in which an electrode 4, a hole transport layer 7, a perovskite layer 6, an electron transport layer 5, and a second electrode 8 are laminated in this order.

(1) Substrate 3

The substrate 3 is not particularly problematic as long as it has a function of holding the layers laminated on the substrate, but a transparent substrate having a total light transmittance of 50% or more is preferable, and the transparent substrate is not particularly limited. However, glass and transparent resins such as acrylic resin, polyolefin resin, polyester resin, polycarbonate resin, and polyamide resin can be mentioned. The substrate 3 may be replaced by a first electrode.

(2) First Electrode 4

As the first electrode 4, a material having conductivity and transmitting light can be used, for example, tin-doped indium oxide (ITO), fluorine-doped tin oxide (FTO), antimon-doped tin oxide (ATO), and oxidation. Zinc (ZnO), tin oxide ($SnO_2$), indium zinc oxide (ITO), indium gallium zinc oxide (IGZO), aluminum-doped zinc (AZO), graphene and the like can be used. These may be used alone or in combination of two or more. Further, it may be used in combination with an electrode material that is not transparent due to pattern formation.

The thickness of the first electrode 4 is, for example, 200 nm to 1200 nm. It is desirable to adjust the resistance value so that it is 5 to 15 Ω/□.

The first electrode 4 can be formed by a coating method such as vapor deposition, sputtering, a spray method, a spin coating method, or a dip coating method.

The first electrode may be washed, ozone-treated, etc. before laminating the next layer.

(3) Second Electrode 8

The second electrode 8 includes gold, silver, aluminum, copper, platinum, rhodium, indium, titanium, iron, nickel, tin, zinc, molybdenum, oxides thereof, alloys containing any of these, and conductive. A carbon material or the like can be used. The electrode 8 may be one layer or two layers using different materials. Further, the material used for the first electrode 7 can also be used.

The thickness of the second electrode 8 is, for example, 50 nm to 100 nm.

The second electrode 8 can be formed by a coating method such as vapor deposition, sputtering, a spray method, a spin coating method, or a dip coating method.

(4) Perovskite Layer 6

The perovskite layer 6 contains a compound having a perovskite structure represented by ABX3. Here, A is a monovalent cation, preferably an alkali metal cation, an organic cation, more preferably a cesium cation, a francium cation, $RNH_3^+$ (R is an alkyl group having 1 to 10 carbon atoms), $NH_2CHNH_2^+$, and B. Is a divalent cation, preferably a transition metal element or a divalent cation of a group 13 to 15 element, more preferably $Pb^{2+}$, $Sn^{2+}$, $Ge^{2+}$, and X is an anion, preferably an anion halide. Is. Each of A, B, and X may be one kind alone or a combination of a plurality of kinds, but it is preferable that one kind alone. Specific examples thereof include $RNH_3PbX_3$, R $(NH_2)$ $2PbX_3$, $RNH_3SnX_3$, R $(NH_2)$ $2SnX_3$ (R is an alkyl group having 1 to 10 carbon atoms), and a complex of these with dimethylformamide. These may be used alone or in combination of two or more.

The thickness of the perovskite layer 6 is, for example, 100 nm to 600 nm.

The perovskite layer 6 can be formed by dissolving the component forming the perovskite layer 6 in a solvent and applying it by a spray method, a spin coating method, a dip coating method, a die coating method or the like.

(5) Hole Transporting Layer 7

The hole transport layer 7 is formed by using the hole transport layer forming composition. Therefore, the hole transport layer 7 contains the compound represented by the general formula (VIII). Further, the hole transport layer 7 does not contain a dopant.

The thickness of the hole transport layer 7 is, for example, 10 nm to 500 nm, more preferably 50 nm to 150 nm.

The hole transport layer 7 is obtained by applying the hole transport layer forming composition by a spray method, a doctor blade method, a bar coating method, a spin coating method, a dip coating method, a die coating method, or the like, or printing by a screen printing method. It can be formed by doing. Then, the solvent is dried while heating as necessary.

(6) Electron Transporting Layer 5

The electron transport layer 5 includes a semiconductor. Examples of semiconductors include organic n-type semiconductors and inorganic n-type semiconductors. The band gap of the semiconductor is 1.5 to 4.2 eV.

Examples of the organic n-type semiconductor include imide compounds, quinone compounds, fullerenes and derivatives thereof. Examples of the inorganic n-type semiconductor include metal oxides and perovskite oxides. Examples of the metal element include transition metals and typical metals of groups 12 to 15, and titanium dioxide is preferable. Examples of titanium dioxide (titania) include compact titania and porous titania, which can also be treated with titanium tetrachloride.

Examples of perovskite oxides include $SrTiO_3$ and $CaTIO_3$.

The thickness of the electron transport layer 5 is, for example, 10 nm to 500 nm.

The electron transport layer 5 can be formed by a spray method, a spin coating method, a vacuum vapor deposition method, or the like.

(7) Others

A configuration that can be provided by a normal perovskite solar cell, such as sealing an element with a blocking layer or a glass plate, can be provided as long as the object of the present invention is not impaired.

EXAMPLES OF EXECUTION

Hereinafter, the present invention will be described in more detail with reference to Examples and Comparative Examples, but the present invention is not limited to these Examples.

Synthesis Example 1

Synthesis of 4-Methoxy-N-(4-Methoxyphenyl)-N-Phenylaniline (Compound 27)

4-Bromoanisole (Compound 26; 25.1 g, 134 mmol)), tris (dibenzylideneacetone) dipalladium (635 mg, 0.694 mmol), and tertiary butoxysodium (19.1 g, 199 mmol) are placed in a two-necked flask. did. Next, triterchary butylphosphine (584 mg, 2.89 mmol), aniline (compound 25; 6.17 g, 66.3 mmol), and toluene (160 mL) were added and stirred at 90° C. for 1 hour. After the reaction, the insoluble solid was filtered off and washed with toluene. The filtrate was washed twice with water (50 mL) and once with saturated brine (50 mL), and then the organic layer was dried over magnesium sulfate. After the magnesium sulfate was filtered off, the filtrate was concentrated under reduced pressure. The obtained crude product was filtered through a silica pad using a mixed solvent of dichloromethane:hexane=1:1. The filtrate was concentrated and then washed with hexane to give 18.7 g (61.2 mmol) of compound 27 as a white solid in 92% yield.

$^1H$ NMR (400 MHz, $CDCl_3$): δ 7.17 (t, $^3J$(H,H)=8.4 Hz, 2H), 7.04 (d, $^3J$(H,H)=9.2 Hz, 4H), 6.94 (d, $^3J$(H,H)=8.4 Hz, 2H), 6.86 (t, $^3J$(H,H)=8.0 Hz, 1H), 6.82 (d, $^3J$(H,H)=9.2 Hz, 4H), 3.79 (s, 6H).

Synthesis Example 2

Synthesis of 4-(Bis(4-methoxyphenyl)amino) Benzaldehyde (Compound 28)

4-Methoxy-N-(4-methoxyphenyl)-N-phenylaniline (Compound 27; 18.7 g, 61.2 mmol) was dissolved in DMF (300 mL). Phosphoryl oxychloride (17 mL) was added, and the mixture was stirred at 80° C. for 2 hours. After adding water (370 mL), the pH was adjusted to 10 with a 25% aqueous sodium hydroxide solution to precipitate a solid. The solid was collected by filtration and washed with water (50 mL). The obtained crude product was filtered through a silica pad using dichloromethane, and then concentrated to obtain 18.7 g (56.1 mmol) of Compound 28 as a yellow solid in a yield of 92%.

$^1H$ NMR (400 MHz, $CDCl_3$): δ 9.76 (s, 1H), 7.63 (d, $^3J$(H,H)=8.8 Hz, 2H), 7.13 (d, $^3J$(H,H)=8.8 Hz, 4H), 6.89 (d, $^3J$(H,H)=8.8 Hz, 4H), 6.84 (d, $^3J$(H,H)=8.8 Hz, 2H), 3.82 (s, 6H).

General Formula [70]

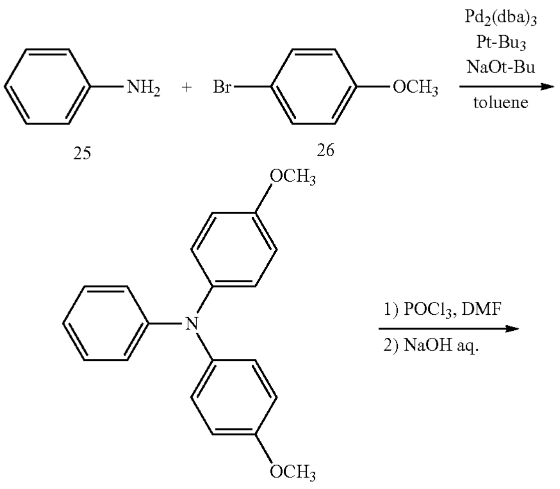

25 26

27

-continued

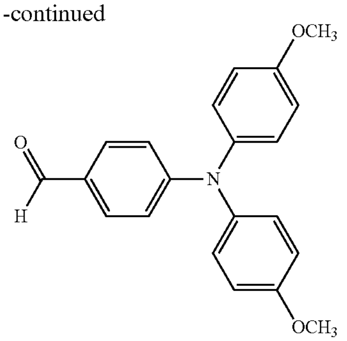

28

General Formula [71]

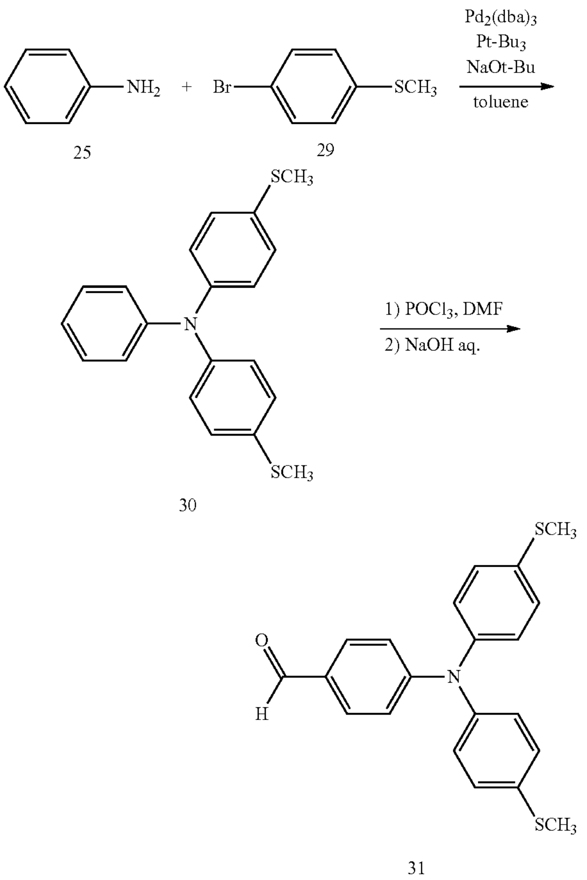

Synthesis Example 3

Synthesis of 4-Methylthio-N-(4-Methylthiophenyl)-N-Phenylaniline (Compound 30)

4-Bromothioanisole (Compound 29; 9.49 g, 46.7 mmol)), tris (dibenzylideneacetone) dipalladium (223 mg, 0.244 mmol), and tertiary butoxysodium (6.75 g, 70.2 mmol) in a four-necked flask. I put it in. Next, triterchary butylphosphine (211 mg, 1.04 mmol), aniline (compound 25; 2.17 g, 23.3 mmol), and toluene (60 mL) were added and stirred at 90° C. for 4 hours. After the reaction, the insoluble solid was filtered off and washed with toluene. The filtrate was washed twice with water (20 mL) and once with saturated brine (20 mL), and then the organic layer was dried over magnesium sulfate. After the magnesium sulfate was filtered off, the filtrate was concentrated under reduced pressure. The obtained crude product was filtered through a silica pad using a mixed solvent of dichloromethane:hexane=1:4. The filtrate was concentrated and then washed with hexane to give 6.31 g (18.6 mmol) of compound 30 as a pale orange solid in 80% yield.

$^1$H NMR (400 MHz, $CDCl_3$): δ 7.23 (t, $^3$J(H,H)=8.0 Hz, 2H), 7.17 (d, $^3$J(H,H)=8.8 Hz, 4H), 7.05 (d, $^3$J(H,H)=8.0 Hz, 2H), 7.02-6.97 (m, 5H), 2.46 (s, 6H).

Synthesis Example 4

Synthesis of 4-(Bis(4-methylthiophenyl)amino) Benzaldehyde (Compound 31)

4-Methylthio-N-(4-methylthiophenyl)-N-phenylaniline (Compound 30; 2.52 g, 7.44 mmol) was dissolved in DMF (50 mL). Phosphoryl oxychloride (6.9 mL) was added, and the mixture was stirred at 80° C. for 2 hours. After adding water (50 mL), the pH was adjusted to 8 with a 25% aqueous sodium hydroxide solution to precipitate a solid. The solid was collected by filtration and washed with water (250 mL). The obtained crude product was filtered through a silica pad using dichloromethane, and then concentrated to obtain 2.59 g (7.08 mmol) of Compound 31 as a yellow solid in a yield of 95%.

$^1$H NMR (400 MHz, DMSO-$d_6$): δ 9.75 (s, 1H), 7.70 (d, $^3$J(H,H)=8.0 Hz, 2H), 7.29 (d, $^3$J(H,H)=8.8 Hz, 4H), 7.12 (d, $^3$J(H,H)=8.8 Hz, 4H), 6.87 (d, $^3$J(H,H)=8.8 Hz, 2H), 2.47 (s, 6H).

Synthesis Example 5

Synthesis of 4-(Bis(4-dimethylaminophenyl)amino) Benzaldehyde (Compound 34)

4-Iodobenzaldehyde (Compound 32; 9.28 g, 40.0 mmol), bis (4-dimethylaminophenyl) amine (Compound 33; 5.13 g, 20.1 mmol), Tris (dibenzylideneacetone) dipalladium (183 mg, 0.200 mmol), And tertiarybutoxysodium (2.88 g, 30.0 mmol) were charged into a four-necked flask. Next, triterchary butylphosphine (174 mg, 0.86 mmol) and toluene (60 mL) were added, and the mixture was stirred at 100° C. for 5 hours. After the reaction, the mixture was quenched with water (100 mL) and separated. Extraction was performed three times with toluene (30 mL) and then washed once with saturated brine (50 mL). The organic layer was dried over magnesium sulfate, magnesium sulfate was filtered off, and the filtrate was concentrated under reduced pressure. The resulting crude product was purified by silica gel column chromatography using a mixed solvent of dichloromethane: ethyl acetate=20:1 to obtain 2.91 g (8.09 mmol) of compound 34 as a yellow solid in a yield of 40%.

$^1$H NMR (400 MHz, DMSO-$d_6$): δ 9.64 (s, 1H), 7.59 (d, $^3$J(H,H)=8.0 Hz, 2H), 7.07 (d, $^3$J(H,H)=8.0 Hz, 4H), 6.74 (d, $^3$J(H,H)=8.0 Hz, 4H), 6.62 (d, $^3$J(H,H)=8.0 Hz, 2H), 2.89 (s, 12H).

General Formula [72]

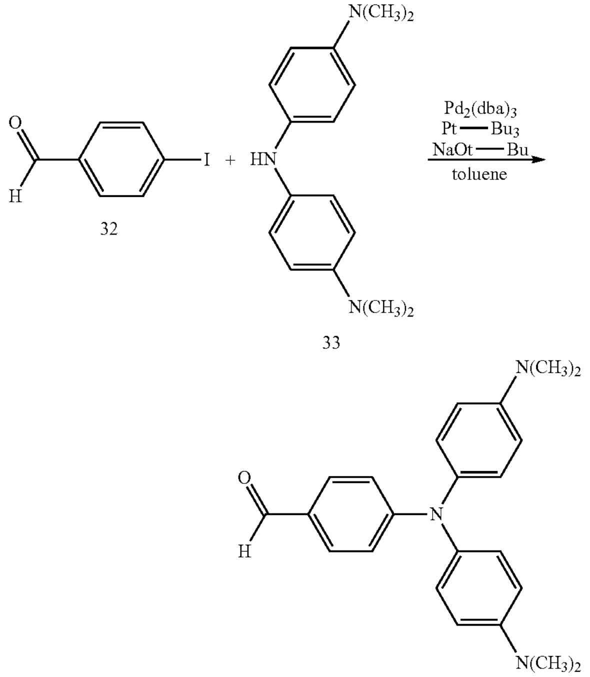

32 33 34

Synthesis Example 6

Synthesis of Bis(3-methoxyphenyl)amine (Compound 37)

Palladium acetate (306 mg, 1.36 mmol), BINAP (802 mg, 1.29 mmol), and cesium carbonate (7.30 g, 22.4 mmol) were placed in a two-necked flask. 3-Methoxyaniline (Compound 35; 3.05 g, 24.8 mmol), 3-bromoanisole (Compound 36; 3.31 g, 17.7 mmol), and toluene (50 mL) were added, and the mixture was stirred at 100° C. for 15 hours. Palladium acetate (150 mg, 0.67 mmol), BINAP (403 mg, 0.65 mmol), and cesium carbonate (768 mg, 2.36 mmol) were added and stirred for an additional 19 hours. After the reaction, the mixture was quenched with water (100 mL) and separated. Extraction was performed three times with toluene (30 mL) and then washed once with saturated brine (100 mL). The organic layer was dried over magnesium sulfate, magnesium sulfate was filtered off, and the filtrate was concentrated under reduced pressure. The crude product obtained was purified by silica gel column chromatography using a mixed solvent of dichloromethane:hexane=1:1 to obtain 3.22 g (14.0 mmol) of Compound 37 as a brown oil in a yield of 79%.

$^1$H NMR (400 MHz, DMSO-d$_6$): δ 8.16 (s, 1H), 7.12 (t, $^3$J(H,H)=8.0 Hz, 2H), 6.65 (dd, $^3$J(H,H)=8.0 Hz, $^4$J(H,H)=2.0 Hz, 2H), 6.60 (t, $^4$J(H,H)=2.0 Hz, 2H), 6.40 (dd, $^3$J(H,H)=8.0 Hz, $^4$J(H,H)=2.0 Hz, 2H), 3.70 (s, 6H).

Synthesis Example 7

Synthesis of 4-(Bis(3-methoxyphenyl)amino) Benzaldehyde (Compound 38)

4-Iodobenzaldehyde (Compound 32; 3.15 g, 13.6 mmol), tris (dibenzylideneacetone) dipalladium (104 mg, 0.114 mmol), and tertiary butoxysodium (1.32 g, 13.7 mmol) were placed in a two-necked flask. Next, bis (3-methoxyphenyl) amine (Compound 37; 2.17 g, 9.46 mmol), tritersial butylphosphine (94 mg, 0.46 mmol) and toluene (50 mL) were added and stirred at 100° C. for 4 hours. After the reaction, the mixture was quenched with water (30 mL) and separated. After extraction with toluene (10 mL) and dichloromethane (10 mL), the organic layer was dried over magnesium sulfate. After the magnesium sulfate was filtered off, the filtrate was concentrated under reduced pressure. The crude product obtained was purified by silica gel column chromatography using a mixed solvent of dichloromethane: hexane=2:1 to obtain 1.78 g (5.34 mmol) of Compound 38 as a white solid in a yield of 56%.

$^1$H NMR (400 MHz, DMSO-d$_6$): δ 9.76 (s, 1H), 7.71 (d, $^3$J(H,H)=8.0 Hz, 2H), 7.32 (t, $^3$J(H,H)=8.0 Hz, 2H), 6.90 (d, $^3$J(H,H)=8.0 Hz, 2H), 6.82 (dd, $^3$J(H,H)=8.0 Hz, $^4$J(H,H)=2.4 Hz, 2H), 6.75 (dd, $^3$J(H,H)=8.0 Hz, $^4$J(H,H)=2.4 Hz, 2H), 6.72 (t, $^4$J(H,H)=2.4 Hz, 2H), 3.70 (s, 6H).

General Formula [73]

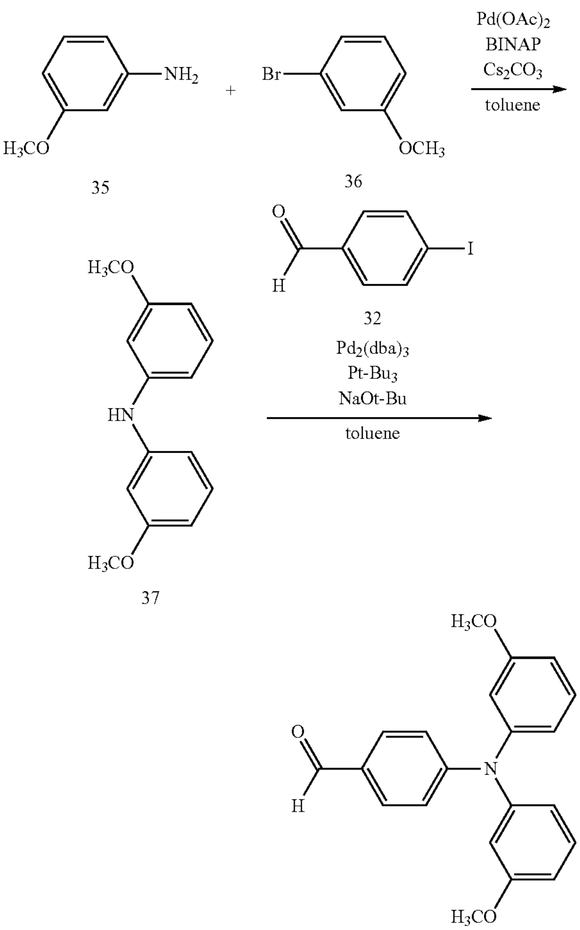

35 36 32 37 38

Synthesis Example 8

Synthesis of (E,E)-1,4-Bis[4-[bis(4-methoxyphenyl) amino]styryl]Benzene (Compound 1)

Add p-bis (diethylphosphono) xylene (Compound 39; 1.14 g, 3.00 mmol) and 4-(bis (4-methoxyphenyl) amino)

benzaldehyde (Compound 28; 2.01 g, 6.05 mmol) to THF (90 mL). Melted and cooled with ice water. Tarshary butoxy-potassium (1.35 g, 12.0 mmol) was added to the solution, and the mixture was stirred at room temperature for 1 hour. After the reaction, water (90 mL) was quenched and the mixture was stirred while cooling with ice to precipitate a yellow solid. The precipitated solid was collected by filtration and washed with water (50 mL) and methanol (50 mL). The crude product obtained was dissolved in dichloromethane (30 mL) and reprecipitated with diethyl ether (60 mL) to give 1.51 g (2.05 mmol) of compound 1 as a yellow solid in 68% yield.

$^1$H NMR (400 MHz, $CDCl_3$): δ 7.44 (s, 4H), 7.32 (d, $^3$J(H,H)=8.4 Hz, 4H), 7.07 (d, $^3$J(H,H)=8.8 Hz, 8H), 7.03 (d, $^3$J(H,H)=16.0 Hz, 2H), 6.94 (d, $^3$J(H,H)=16.0 Hz, 2H), 6.90 (d, $^3$J(H,H)=8.8 Hz, 4H), 6.83 (d, $^3$J(H,H)=8.4 Hz, 8H), 3.80 (s, 12H).

General Formula [74]

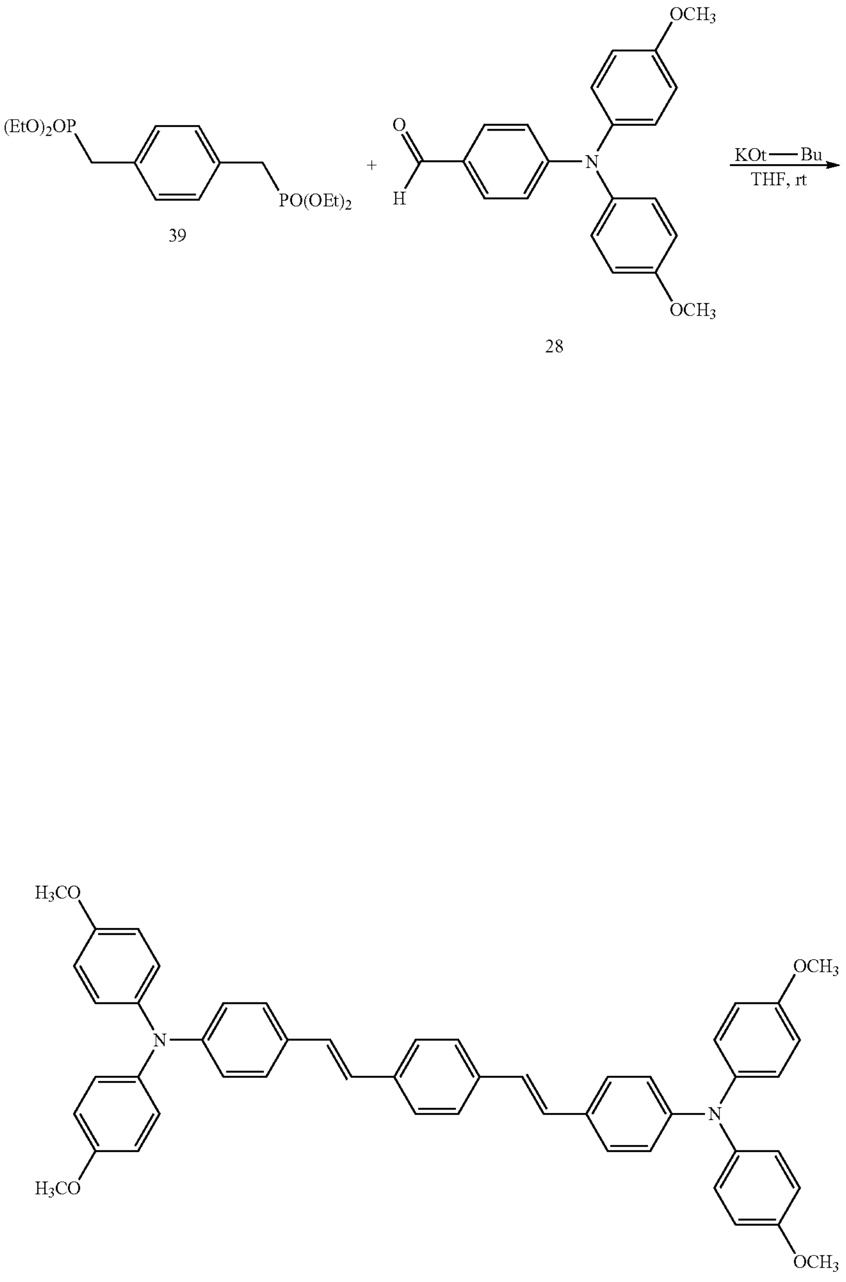

39

28

1

Synthesis Example 9

Synthesis of (E, E)-1,4-Bis[4-[bis(4-methylthiophenyl)amino]styryl] Benzene (Compound 2)

Add p-bis (diethylphosphono) xylene (Compound 39; 756 mg, 2.00 mmol) and 4-(bis (4-methylthiophenyl) amino) benzaldehyde (Compound 31; 1.47 g, 4.03 mmol) to THF (60 mL). Melted and cooled with ice water. Tarshary butoxy-potassium (900 mg, 8.02 mmol) was added to the solution, and the mixture was stirred at room temperature for 1 hour. After the reaction, water (60 mL) was quenched and the mixture was stirred while cooling with ice to precipitate a yellow solid. The precipitated solid was collected by filtration and washed with water (50 mL) and methanol (50 mL). The crude product obtained was dissolved in dichloromethane (35 mL) and reprecipitated with diethyl ether (35 mL) to give 1.31 g (1.64 mmol) of compound 2 as a yellow solid in a yield of 82%.

$^{1}$H NMR (400 MHz, DMSO-$d_6$): δ 7.55 (s, 4H), 7.49 (d, $^{3}$J(H,H)=8.8 Hz, 4H), 7.22 (d, $^{3}$J(H,H)=8.4 Hz, 8H), 7.21 (d, $^{3}$J(H,H)=16.8 Hz, 2H), 7.10 (d, $^{3}$J(H,H)=16.8 Hz, 2H), 6.98 (d, $^{3}$J(H,H)=8.4 Hz, 8H), 6.93 (d, $^{3}$J(H,H)=8.4 Hz, 4H), 2.45 (s, 12H).

General Formula [75]

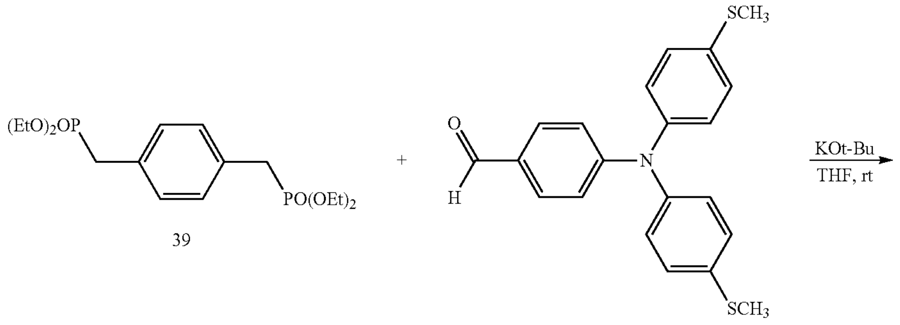

39

31

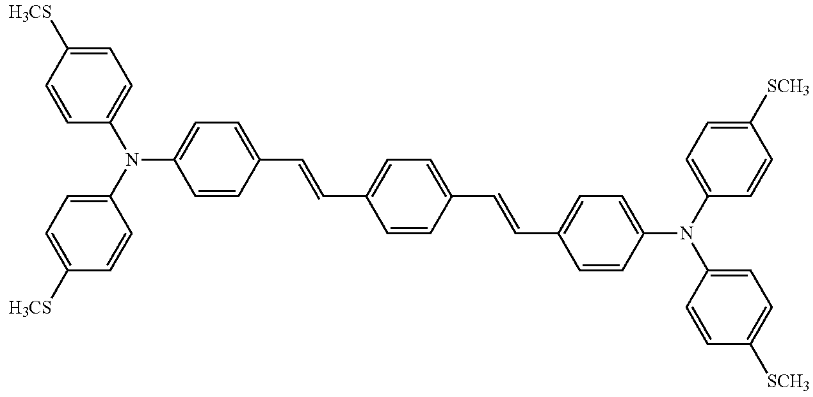

2

Synthesis Example 10

Synthesis of (E, E)-1,4-Bis[4-[bis(4-dimethylamino-phenyl)amino]styryl]Benzene (Compound 3)

THF (30 mL) of p-bis (diethylphosphono) xylene (Compound 39; 378 mg, 1.00 mmol) and 4-(bis (4-dimethylaminophenyl) amino) benzaldehyde (Compound 34; 730 mg, 2.03 mmol) Dissolved in, cooled with ice water. Tarshary butoxypotassium (450 mg, 4.01 mmol) was added to the solution, and the mixture was stirred at room temperature for 4 hours. After the reaction, the orange solid was precipitated by quenching with water (20 mL). The precipitated solid was collected by filtration and washed with water (10 mL) and methanol (10 mL) to give 710 mg (0.90 mmol) of Compound 3 as an orange solid in 90% yield.

$^1$H NMR (400 MHz, $CD_2Cl_2$): δ 7.44 (s, 4H), 7.29 (d, $^3J$(H,H)=8.8 Hz, 4H), 7.03 (d, $^3J$(H,H)=16.4 Hz, 2H), 7.02 (d, $^3J$(H,H)=8.8 Hz, 8H), 6.90 (d, $^3J$(H,H)=16.4 Hz, 2H), 6.80 (d, $^3J$(H,H)=8.4 Hz, 4H), 6.69 (d, $^3J$(H,H)=8.8 Hz, 8H), 2.92 (s, 24H).

General Formula [76]

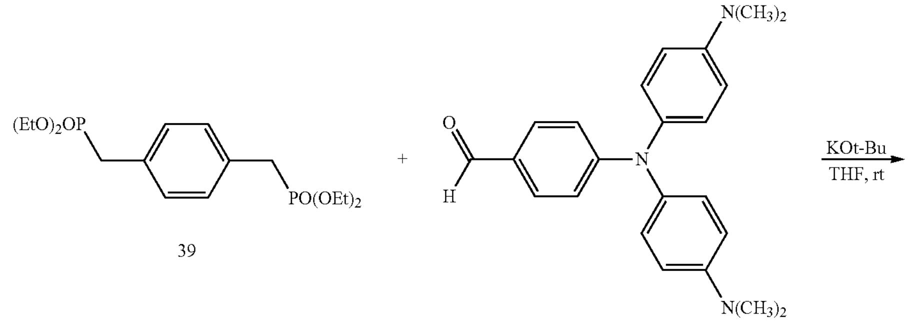

39

34

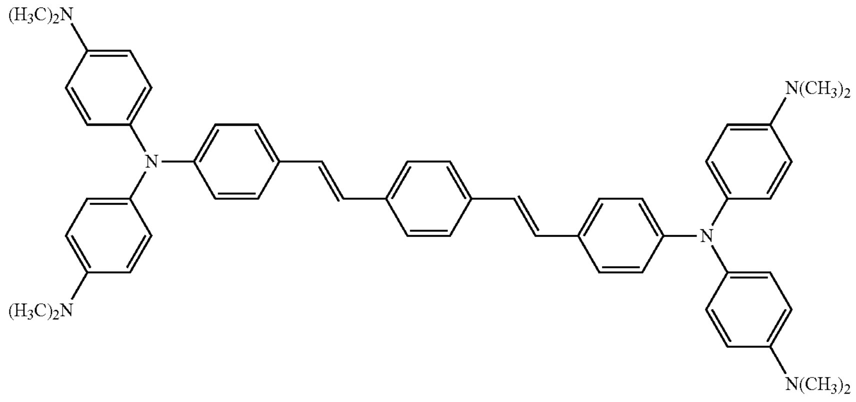

3

Synthesis Example 11

Synthesis of (E, E)-1,4-Bis[4-[bis(3-methoxyphenyl)amino]styryl] Benzene (Compound 5)

Add p-bis (diethylphosphono) xylene (Compound 39; 378 mg, 1.00 mmol) and 4-(bis (3-methoxyphenyl) amino) benzaldehyde (Compound 38; 700 mg, 2.10 mmol) to THF (30 mL). Melted and cooled with ice water. Tarshary butoxypotassium (460 mg, 4.10 mmol) was added to the solution, and the mixture was stirred at room temperature for 4 hours. After the reaction, water (50 mL) was quenched, dichloromethane (30 mL) was added, and the liquid was separated. After further extraction with dichloromethane (15 mL) twice, the organic layer was washed with saturated brine (40 mL). After the magnesium sulfate was filtered off, the filtrate was concentrated under reduced pressure. The crude product obtained was dissolved in dichloromethane (10 mL) and reprecipitated with methanol (40 mL) to give 698 mg (0.95 mmol) of Compound 5 as a yellow solid in 95% yield.

$^1$H NMR (400 MHz, $CDCl_3$): δ 7.47 (s, 4H), 7.39 (d, $^3J$(H,H)=8.4 Hz, 4H), 7.17 (t, $^3J$(H,H)=8.0 Hz, 4H), 7.073 (d, $^3J$(H,H)=16.0 Hz, 2H), 7.07 (d, $^3J$(H,H)=8.8 Hz, 4H), 6.99 (d, $^3J$(H,H)=16.4 Hz, 2H), 6.70 (dd, $^3J$(H,H)=8.0 Hz, $^4J$(H,H)=1.2 Hz, 4H), 6.66 (t, $^4J$(H,H)=1.2 Hz, 4H), 6.59 (dd, $^3J$(H,H)=8.0 Hz, $^4J$(H,H)=1.6 Hz, 4H), 3.73 (s, 12H).

General Formula [77]

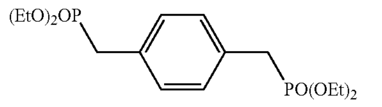

+

39

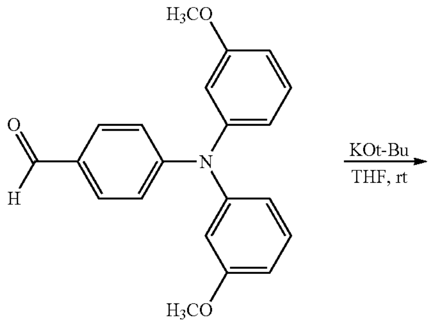

38

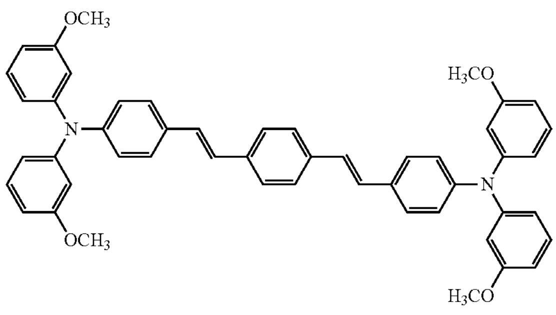

5

Synthesis Example 12

Synthesis of 1,3,5-Tris(diethylphosphonomethyl)benzene (Compound 41)

1,3,5-Tris (bromomethyl) benzene (Compound 40; 2.50 g, 7.01 mmol) and triethyl phosphate (5.5 mL, 31.8 mmol) were mixed and stirred at 130° C. for 1 hour. After the reaction, the reaction mixture was concentrated while heating at 100° C. to obtain 3.46 g (6.55 mmol) of Compound 41 as a pale yellow oil in a yield of 93%.

$^1$H NMR (400 MHz, $CDCl_3$): δ7.13 (m, 3H), 4.02 (m, 12H), 3.11 (d, $^3J$(H,P)=22.8 Hz, 6H), 1.25 (t, $^3J$(H,H)=6.8 Hz, 18H).

Synthesis Example 13

Synthesis of (E, E, E)-1,3,5-Tris[4-[bis(4-methoxyphenyl)amino]styryl] Benzene (Compound 7)

1,3,5-Tris (diethylphosphonomethyl) benzene (Compound 41; 1.06 g, 2.00 mmol) and 4-(bis (4-methoxyphenyl) amino) benzaldehyde (Compound 28; 2.02 g, 6.06 mmol) were dissolved in THF (90 mL) and cooled with ice water. Tarshary butoxypotassium (1.35 g, 12.0 mmol) was added to the solution, and the mixture was stirred at room temperature for 1.5 hours. After the reaction, it was quenched with water (90 mL). The organic layer was extracted twice with dichloromethane (30 mL) and washed with water (30 mL) and saturated brine (30 mL). After the magnesium sulfate was filtered off, the filtrate was concentrated under reduced pressure. The crude product obtained was dissolved in dichloromethane (12 mL) and reprecipitated with methanol (18 mL) to give 1.87 g (1.76 mmol) of compound 7 as a yellow solid in 88% yield.

$^1$H NMR (400 MHz, $CDCl_3$): δ 7.45 (s, 3H), 7.35 (d, $^3J$(H,H)=8.8 Hz, 6H), 7.11 (d, $^3J$(H,H)=16.0 Hz, 3H), 7.08 (d, $^3J$(H,H)=8.8 Hz, 12H), 6.97 (d, $^3J$(H,H)=16.0 Hz, 3H), 6.92 (d, $^3J$(H,H)=8.8 Hz, 6H), 6.84 (d, $^3J$(H,H)=9.2 Hz, 12H), 3.81 (s, 18H).

General Formula [78]

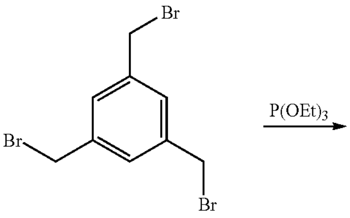

40

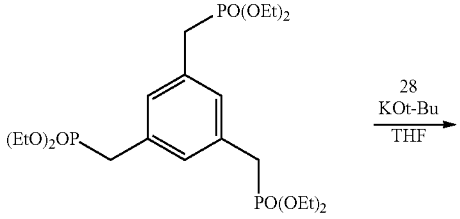

41

-continued

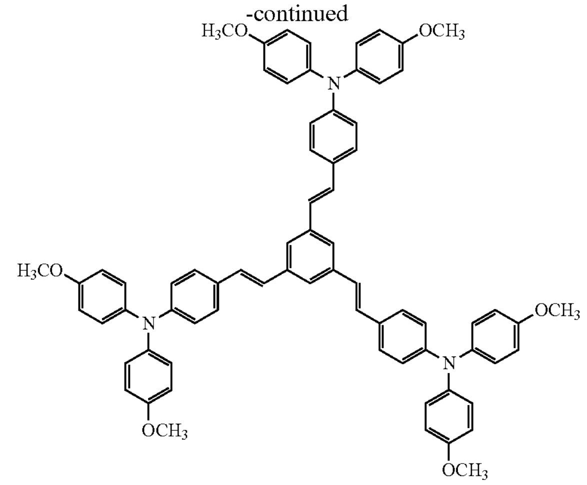

7

-continued

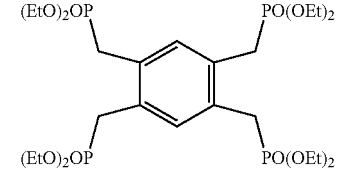

44

Synthesis Example 14

Synthesis of 1,2,4,5-Tetrakis(bromomethypbenzene (Compound 43)

1,2,4,5-Tetramethylbenzene (Compound 42; 5.37 g, 40.0 mmol) was dissolved in ethyl acetate (120 mL). N-Bromosuccinimide (32.0 g, 180 mmol) and AIBN (330 mg, 2.01 mmol) were added, and the mixture was stirred at 70° C. for 2 hours. After the reaction, the precipitate was filtered off and the filtrate was concentrated under reduced pressure. The crude product obtained was washed with methanol (80 mL) and recrystallized from toluene (30 mL) to give compound 43 in 6.27 g (13.9 mmol) in 35% yield as a white solid.

$^1$H NMR (400 MHz, $CDCl_3$) δ 7.37 (s, 2H), 4.60 (s, 8H).

Synthesis Example 15

Synthesis of 1,2,4,5-Tetrakis(diethylphosphonomethyl)benzene (Compound 44)

1,2,4,5-Tetrakis (bromomethyl) benzene (Compound 43; 4.50 g, 10.0 mmol) and triethyl phosphate (10.3 mL, 60.0 mmol) were mixed and stirred at 130° C. for 1 hour. After the reaction, the reaction solution was concentrated while heating at 130° C. to obtain a colorless oil as a crude product. After air cooling, hexane (10 mL) was added and stirred to form a white solid. The resulting solid was collected by filtration and washed with hexane to give 6.61 g (9.74 mmol) of compound 44 as a white solid in 97% yield.

$^1$H NMR (400 MHz, $CDCl_3$) δ 7.14 (s, 2H), 3.97 (m, 16H), 3.34 (d, $^3$J(H,P)=19.6 Hz, 8H), 1.21 (t, $^3$J(H,H)=7.2 Hz, 24H).

General Formula [79]

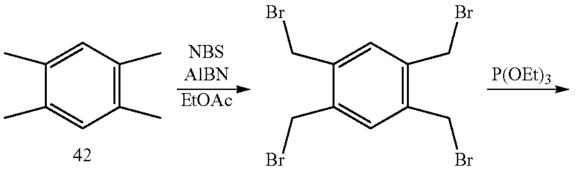

42 43

Synthesis Example 16

Synthesis of (E, E, E, E)-1,2,4,5-Tetrakis[4-[bis(4-methoxyphenyl)amino]styryl]benzene (Compound 8)

1,2,4,5-Tetrakis (diethylphosphonomethyl)benzene (Compound 44; 1.02 g, 1.50 mmol) and 4-(bis (4-methoxyphenyl) amino) benzaldehyde (Compound 28; 2.02 g, 6.06 mmol) Was dissolved in THF (100 mL) and cooled with ice water. Tarshary butoxypotassium (1.35 g, 12.0 mmol) was added to the solution, and the mixture was stirred at room temperature for 1 hour. After the reaction, water (90 mL) was quenched to precipitate an orange solid. The precipitated solid was collected by filtration and washed with water (50 mL) and methanol (50 mL). The crude product obtained was dissolved in dichloromethane (45 mL) and reprecipitated with diethyl ether (45 mL) to give 1.52 g (1.09 mmol) of compound 8 as an orange solid in a yield of 73%.

$^1$H NMR (400 MHz, $CDCl_3$): δ 7.73 (s, 2H), 7.35 (d, $^3$J(H,H)=8.4 Hz, 8H), 7.30 (d, $^3$J(H,H)=16.0 Hz, 4H), 7.07 (d, $^3$J(H,H)=9.2 Hz, 16H), 6.99 (d, $^3$J(H,H)=16.0 Hz, 4H), 6.91 (d, $^3$J(H,H)=8.8 Hz, 8H), 6.83 (d, $^3$J(H,H)=9.2 Hz, 16H), 3.80 (s, 24H).

General Formula [80]

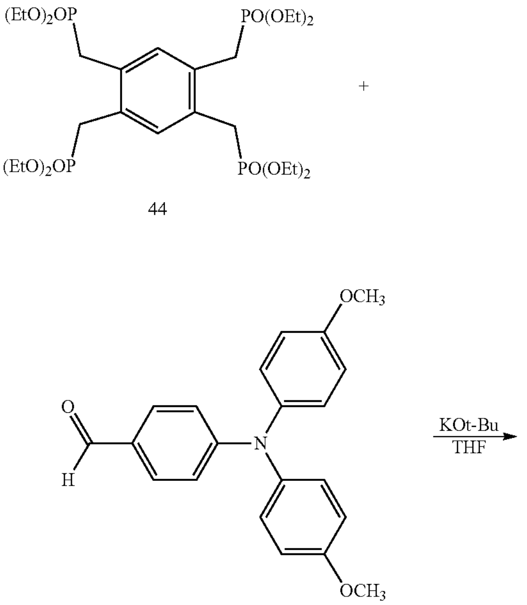

44 28

-continued

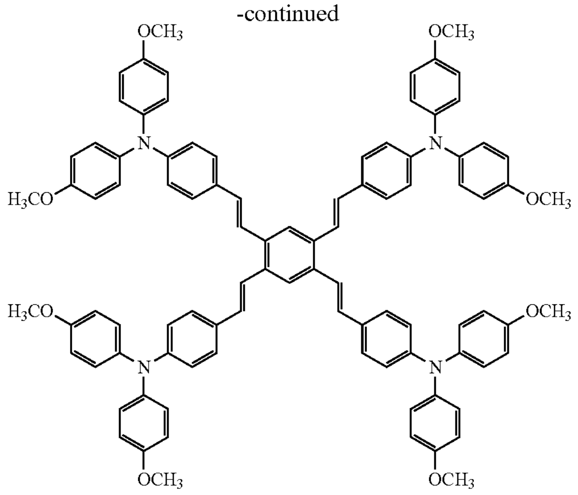

8

Synthesis Example 17

Synthesis of (E, E, E, E)-1,2,4,5-Tetrakis[4-[bis(4-methylthiophenyl)amino]styryl]benzene (Compound 9)

1,2,4,5-Tetrakis (diethylphosphonomethyl) benzene (Compound 44; 372 mg, 0.55 mmol) and 4 -(bis (4-methylthiophenyl) amino) benzaldehyde (Compound 31; 804 mg, 2.20 mmol) Was dissolved in THF (40 mL) and cooled with ice water. Tarshary butoxypotassium (450 mg, 4.01 mmol) was added to the solution, and the mixture was stirred at room temperature for 5 hours. After the reaction, the orange solid was precipitated by quenching with water (30 mL). The precipitated solid was collected by filtration and washed with water (15 mL) and methanol (15 mL). The crude product obtained was dissolved in dichloromethane (80 mL) and reprecipitated with acetonitrile (20 mL) to give 590 mg (0.39 mmol) of Compound 9 as an orange solid in 71% yield.

$^1$H NMR (400 MHz, $CDCl_3$): δ 7.75 (s, 2H), 7.42 (d, $^3J$(H,H)=8.8 Hz, 8H), 7.36 (d, $^3J$(H,H)=16.4 Hz, 4H), 7.19 (d, $^3J$(H,H)=8.8 Hz, 16H), 7.05-6.98 (m, 28H), 2.48 (s, 24H).

General Formula [81]

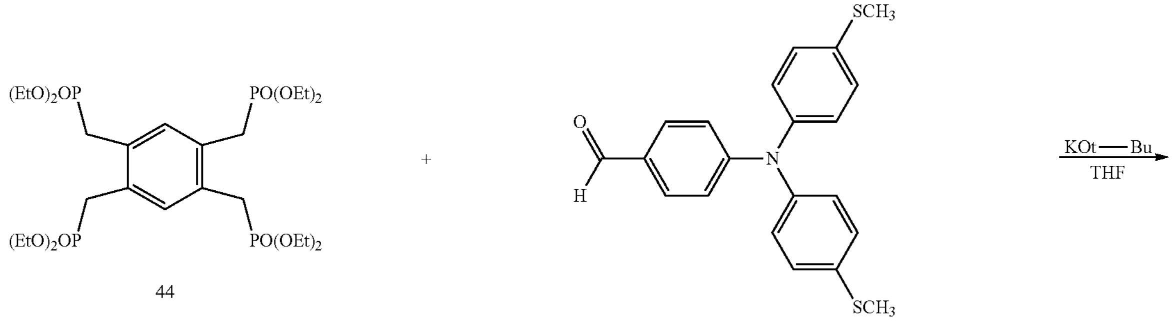

44

31

-continued

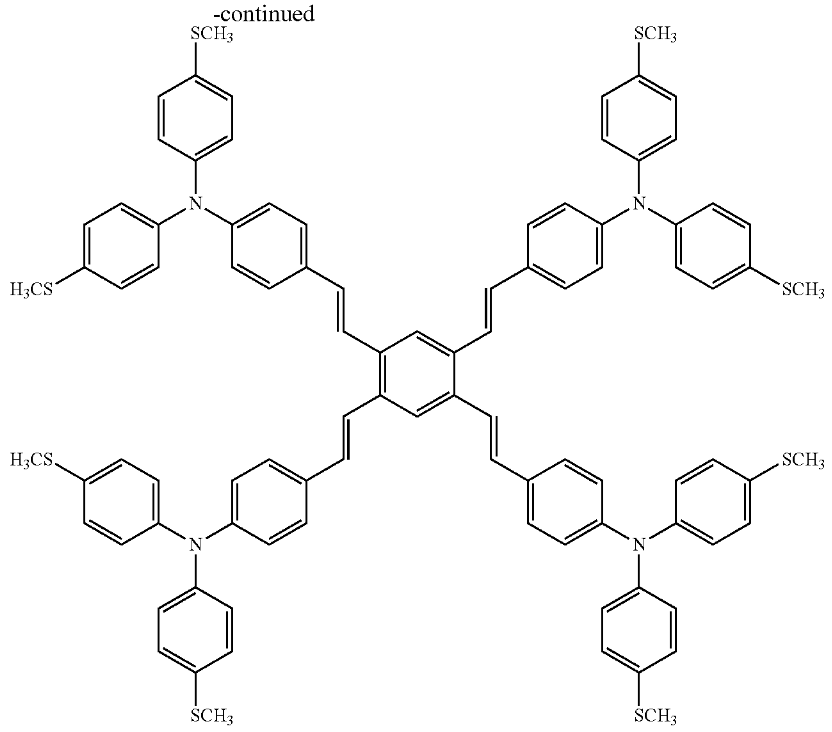

9

Synthesis Example 18

Synthesis of (E, E, E, E)-1,2,4,5-Tetrakis[4-[bis(4-dimethylaminophenyl)amino] styryl]benzene (Compound 10)

1,2,4,5-Tetrakis (diethylphosphonomethyl) benzene (Compound 44; 339 mg, 0.50 mmol) and 4-(bis (4-dimethylaminophenyl) amino) benzaldehyde (Compound 34; 735 mg, 2.04 mmol)) Was dissolved in THF (30 mL) and cooled with ice water. Tarshary butoxypotassium (457 mg, 4.07 mmol) was added to the solution, and the mixture was stirred at room temperature for 20 hours. Compound 34 (97 mg, 0.27 mmol) and THF (10 mL) were added, and the mixture was stirred for 3 hours, then tertiary butoxypotassium (46 mg, 0.41 mmol) was added, and the mixture was stirred for 18 hours. After the reaction, the orange solid was precipitated by quenching with water (20 mL). The precipitated solid was collected by filtration and washed with water (15 mL), acetonitrile (15 mL) and methanol (15 mL). The crude product obtained was dissolved in dichloromethane (50 mL) and reprecipitated with acetonitrile (45 mL) to give 548 mg (0.37 mmol) of compound 10 as an orange solid in a yield of 73%.

$^1$H NMR (400 MHz, DMSO-$d_6$): δ 7.78 (s, 2H), 7.35 (d, $^3$J(H,H)=8.8 Hz, 8H), 7.30 (d, $^3$J(H,H)=15.6 Hz, 4H), 7.04 (d, $^3$J(H,H)=16.0 Hz, 4H), 6.97 (d, $^3$J(H,H)=8.8 Hz, 16H), 6.73 (d, $^3$J(H,H)=8.0 Hz, 8H), 6.67 (d, $^3$J(H,H)=9.2 Hz, 16H), 2.88 (s, 48H).

General Formula [82]

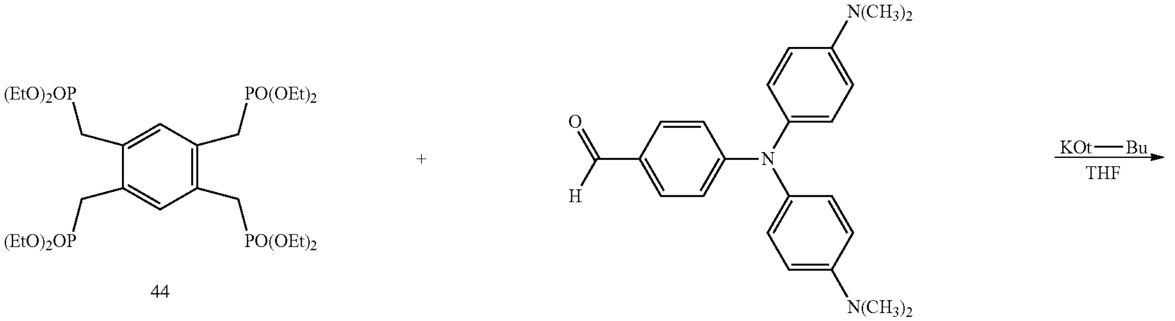

44

34

-continued

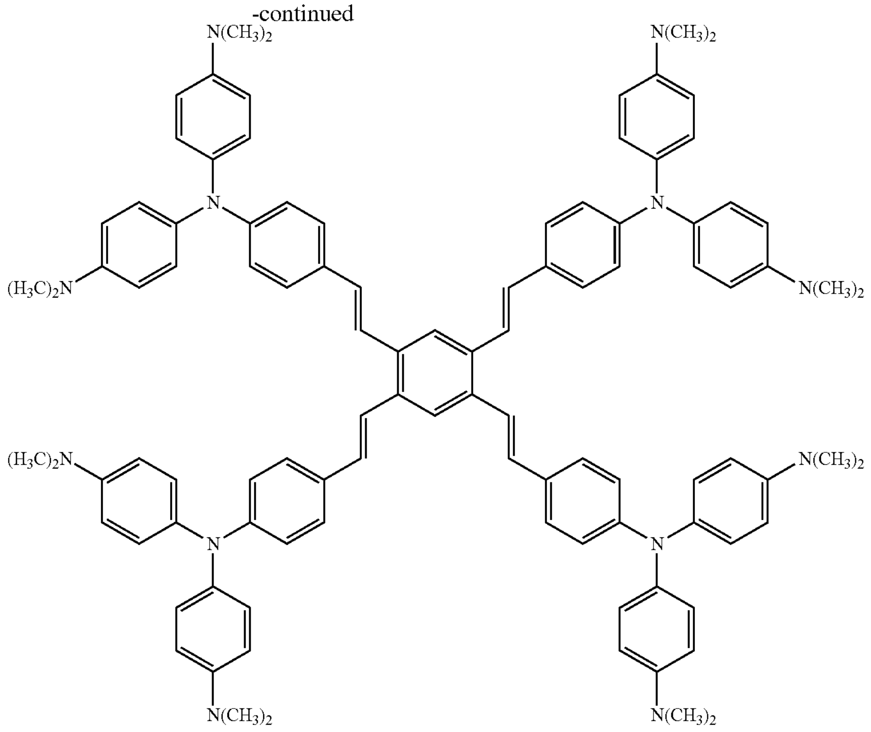

10

Synthesis Example 19

Synthesis of (E, E, E, E)-1,2,4,5-Tetrakis[4-[bis(3-methoxyphenyl)amino]styryl]benzene (Compound 12)

General Formula [83]

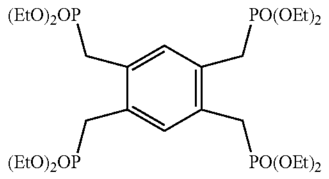

44

+

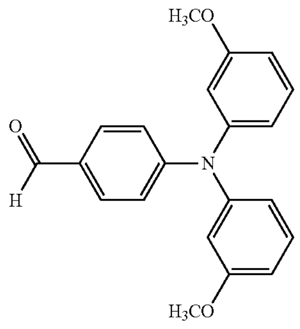

38

KOt—Bu
THF 1,2,4,5-Tetrakis (diethylphosphonomethyl) benzene (Compound 44; 339 mg, 0.50 mmol) and 4-(bis (3-methoxy-phenyl) amino) benzaldehyde (Compound 38; 689 mg, 2.07 mmol) Was dissolved in THF (40 mL) and cooled with ice water. Tarshary butoxypotassium (452 mg, 4.03 mmol) was added to the solution, and the mixture was stirred at room temperature for 4 hours. After the reaction, the mixture was quenched with water (80 mL), extracted three times with dichloromethane (20 mL), and the organic layer was washed with saturated brine (40 mL). The organic layer was dried over magnesium sulfate, filtered off, and the filtrate was concentrated under reduced pressure. The crude product obtained was dissolved in dichloromethane (5 mL) and reprecipitated with acetonitrile (20 mL) to give 563 mg (0.40 mmol) of compound 12 as a yellow solid in 81% yield.

$^{1}$H NMR (400 MHz, DMSO-d6): δ 7.92 (s, 4H), 7.60 (d, $^{3}$J(H,H)=8.8 Hz, 4H), 7.52 (d, $^{3}$J(H,H)=16.4 Hz, 4H), 7.21 (d, $^{3}$J(H,H)=16.4 Hz, 4H), 7.19 (t, $^{3}$J(H,H)=8.0 Hz, 8H), 6.96 (d, $^{3}$J(H,H)=8.4 Hz, 2H), 6.62 (dd, $^{3}$J(H,H)=8.0 Hz, $^{4}$J(H,H)=2.0 Hz, 8H), 6.57 (dd, $^{3}$J(H,H)=8.0 Hz, $^{4}$J(H,H)=2.0 Hz, 8H), 6.50 (dd, $^{4}$J(H,H)=3.0 Hz, 8H), 3.64 (s, 24H).

-continued

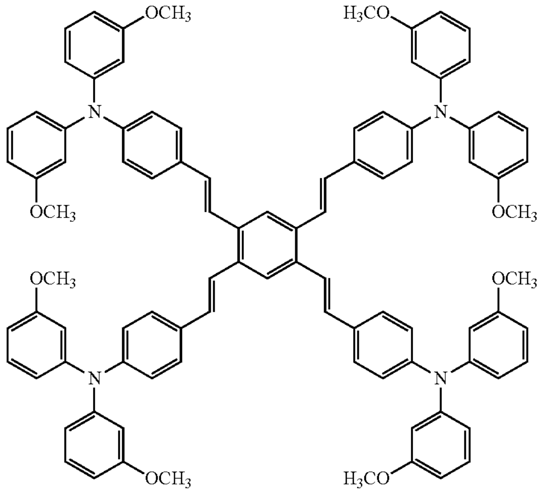

12

Synthesis Example 20

Synthesis of (E, E)-4,4'-Bis[4-[bis(4-methoxyphenyl)amino]styryl]biphenyl (Compound 13)

4,4'-Bis (diethylphosphonomethyl) biphenyl (Compound 46; 454 mg, 1.00 mmol) and 4-(bis (4-methoxyphenyl) amino) benzaldehyde (Compound 28; 675 mg, 2.03 mmol) in THF (It was dissolved in 30 mL) and cooled with ice water. Tarshary butoxypotassium (446 mg, 3.97 mmol) was added to the solution, and the mixture was stirred at room temperature for 16 hours. After the reaction, the mixture was quenched with water (50 mL), extracted three times with dichloromethane (40 mL), and the organic layer was washed with saturated brine (30 mL). The organic layer was dried over magnesium sulfate, filtered off, and the filtrate was concentrated under reduced pressure. The obtained crude product was subjected to silica gel column chromatography using a mixed solvent of dichloromethane/hexane=2:1 as a developing solvent, and 784 mg (0.96 mmol) of Compound 13 was obtained as a yellow solid with a yield of 97%.

$^1$H NMR (400 MHz, $CD_2Cl_2$): δ 7.62 (d, $^3$J(H,H)=8.8 Hz, 4H), 7.56 (d, $^3$J(H,H)=8.0 Hz, 4H), 7.35 (d, $^3$J(H,H)=8.8 Hz, 4H), 7.10 (d, $^3$J(H,H)=16.4 Hz, 2H), 7.06 (d, $^3$J(H,H)=9.2 Hz, 8H), 6.99 (d, $^3$J(H,H)=16.4 Hz, 2H), 6.88 (d, $^3$J(H,H)=8.0 Hz, 4H), 6.85 (d, $^3$J(H,H)=9.2 Hz, 8H), 3.79 (s, 12H).

General Formula [84]

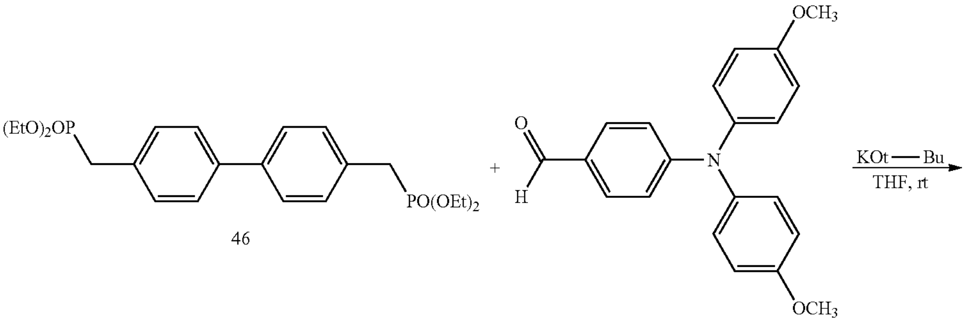

46

28

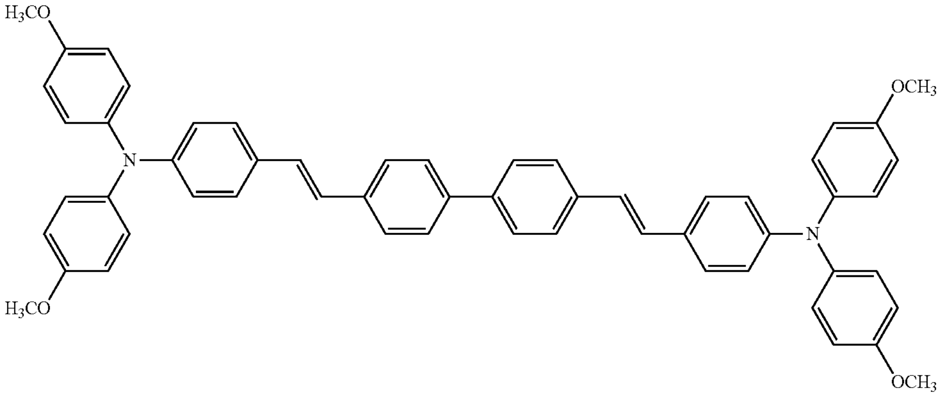

13

Synthesis Example 21

Synthesis of (E, E)-4,4'-Bis[4-[bis(4-methylthiophenyl)amino]styryl]biphenyl (Compound 14)

4,4'-Bis(diethylphosphonomethyl)biphenyl (Compound 46; 454 mg, 1.00 mmol) and 4-(Bis(4-methylthiophenyl)amino)benzaldehyde (Compound 31; 739 mg, 2.02 mmol) in THF (It was dissolved in 30 mL) and cooled with ice water. Tarshary butoxypotassium (447 mg, 3.98 mmol) was added to the solution, and the mixture was stirred at room temperature for 2.5 hours. After the reaction, water (45 mL) was quenched to precipitate a yellow solid. The precipitated solid was collected by filtration and washed with water (50 mL) and methanol (30 mL). The crude product obtained was dissolved in dichloromethane (10 mL) and reprecipitated with diethyl ether (40 mL) to give 696 mg (0.79 mmol) of compound 14 as a yellow solid in 79% yield.

$^1$H NMR (400 MHz, DMSO-$d_6$): δ 7.71 (d, $^3J$(H,H)=8.4 Hz, 4H), 7.65 (d, $^3J$(H,H)=8.4 Hz, 4H), 7.52 (d, $^3J$(H,H)=9.2 Hz, 4H), 7.25 (d, $^3J$(H,H)=16.0 Hz, 2H), 7.23 (d, $^3J$(H,H)=8.8 Hz, 8H), 7.15 (d, $^3J$(H,H)=16.0 Hz, 2H), 6.98 (d, $^3J$(H,H)=8.8 Hz, 8H), 6.94 (d, $^3J$(H,H)=8.8 Hz, 4H), 2.45 (s, 12H).

General Formula [85]

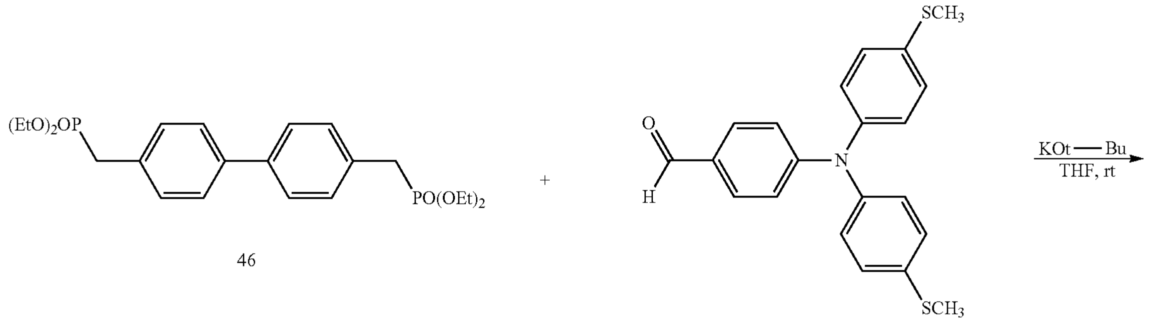

46

31

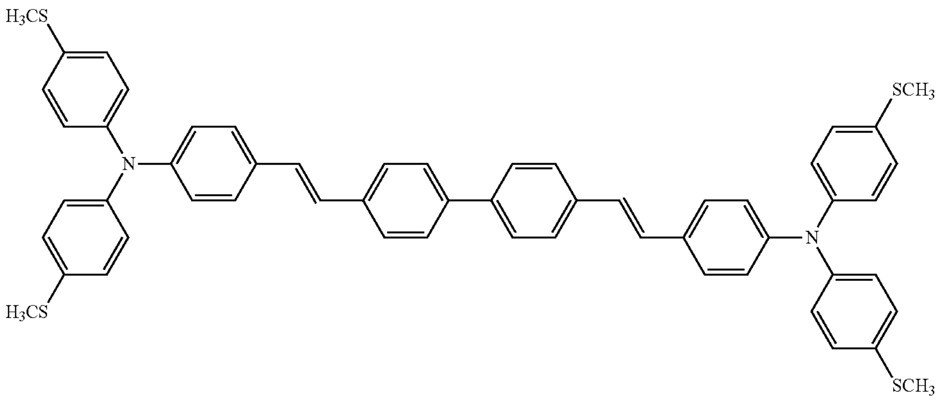

14

Synthesis Example 22

Synthesis of 1,4-Bis[2,2-bis(4-bromophenyl)vinyl]benzene (Compound 48)

Dissolve p-bis (diethylphosphono) xylene (Compound 39; 379 mg, 1.00 mmol) and 4,4'-dibromobenzophenone (Compound 47; 683 mg, 2.01 mmol) in THF (20 mL) and cool in ice water. t-BuOK (483 mg, 4.30 mmol) was added to the solution, and the mixture was stirred at room temperature for 2 hours. After the reaction, quenching with water (10 mL) precipitated a white solid. The precipitated solid was collected by filtration and washed with water (10 mL), methanol (20 mL) and diethyl ether (20 mL) to produce 694 mg (0.93 mmol) of compound 48 as a white solid with a yield of 93%.

$^1$H NMR (400 MHz, $CDCl_3$): δ 7.45 (d, $^3$J(H,H)=9.2 Hz, 4H), 7.42 (d, $^3$J(H,H)=9.2 Hz, 4H), 7.12 (d, $^3$J(H,H)=8.0 Hz, 4H), 7.02 (d, $^3$J(H,H)=8.0 Hz, 4H), 6.84 (s, 2H), 6.82 (s, 4H).

General Formula [86]

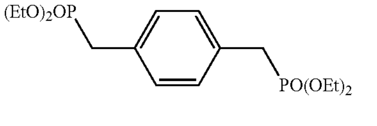

+

39

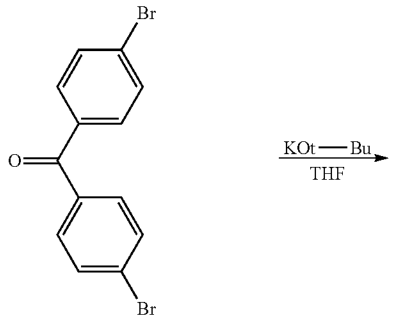

47

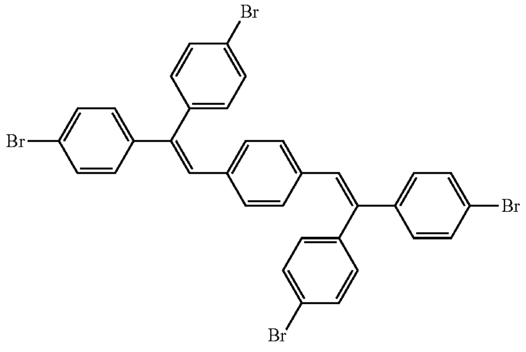

48

Synthesis Example 23

Synthesis of 1,4-Bis[2,2-bis[4-[bis(4-methoxyphenyl)amino]phenyl]vinyl]benzene (Compound 16)

1,4-Bis[2,2-bis(4-bromophenyl)vinyl]benzene (Compound 48; 463 mg, 0.62 mmol), 4,4'-Dimethoxydiphenylamine (Compound 49; 731 mg, 3.19 mmol), Tris(dibenzylideneacetone) Dipalladium (87 mg, 0.095 mmol) and tertiary butoxysodium (459 mg, 4.78 mmol) were charged into a two-necked flask. Next, triterchary butylphosphine (87 mg, 0.43 mmol) and toluene (18 mL) were added, and the mixture was stirred at 90° C. for 15 hours. After the reaction, it was quenched with water (30 mL) and extracted 3 times with dichloromethane (15 mL). The organic layer was dried over magnesium sulfate, magnesium sulfate was filtered off, and the filtrate was concentrated under reduced pressure. The obtained crude product was subjected to silica gel column chromatography using toluene as a developing solvent and then concentrated. Further, by dissolving in dichloromethane (5 mL) and reprecipitation with isopropanol (3.5 mL), 432 mg (0.32 mmol) of Compound 16 was obtained as a yellow solid in a yield of 52%.

$^1$H NMR (400 MHz, $CDCl_3$): δ 7.16 (d, $^3$J(H,H)=8.8 Hz, 4H), 7.06 (d, $^3$J(H,H)=8.8 Hz, 8H), 7.05 (d, $^3$J(H,H)=8.8 Hz, 8H), 7.00 (d, $^3$J(H,H)=8.8 Hz, 4H), 6.87 (d, $^3$J(H,H)=8.8 Hz, 4H), 6.86 (s, 4H), 6.84 (d, $^3$J(H,H)=8.8 Hz, 4H), 6.82 (d, $^3$J(H,H)=8.8 Hz, 8H), 6.80 (d, $^3$J(H,H)=8.8 Hz, 8H), 6.73 (s, 2H), 3.79 (s, 12H), 3.77 (s, 12H).

General Formula [87]

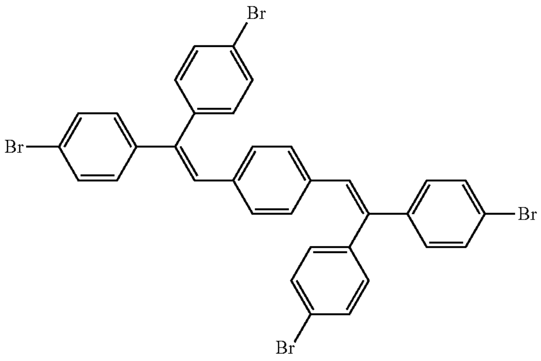

+

48

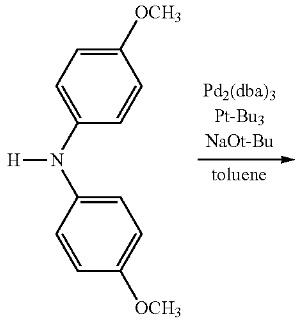

49

-continued

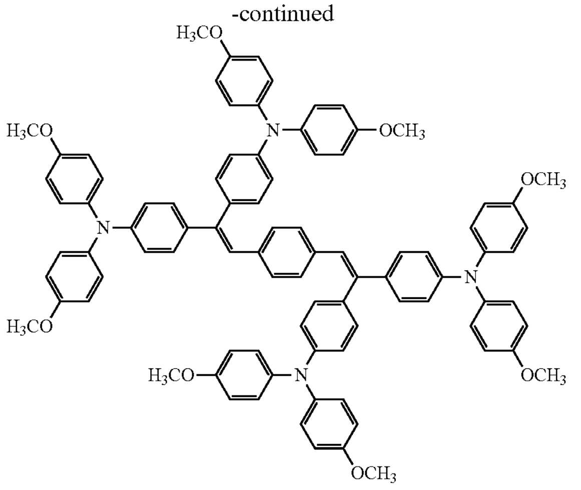

16

Synthesis Example 24

Synthesis of 4,4'-Dimethylthiodiphenylamine (Compound 52)

4-Bromothioanisole (Compound 50; 2.03 g, 9.99 mmol), tris (dibenzylideneacetone) dipalladium (91 mg, 0.099 mmol), and tertiary butoxysodium (1.44 g, 15.0 mmol) are placed in a two-necked flask. did. 4-Methylthioaniline (Compound 51; 2.25 g, 16.2 mmol), tritersial butylphosphine (82 mg, 0.41 mmol) and toluene (15 mL) were added and stirred at 90° C. for 2 hours. After the reaction, the mixture was quenched with water (20 mL) and extracted twice with dichloromethane (10 mL). The organic layer was dried over magnesium sulfate, magnesium sulfate was filtered off, and the filtrate was concentrated under reduced pressure. Silica gel column chromatography using hexane: dichloromethane=2:1 as the developing solvent gave 1.90 g (7.28 mmol) of compound 52 as a yellow solid in a yield of 73%.

$^1$H NMR (400 MHz, DMSO-$d_6$): δ 8.20 (s), 7.19 (d, $^3$J(H,H)=8.8 Hz, 4H), 7.00 (d, $^3$J(H,H)=8.8 Hz, 4H), 2.40 (s, 6H).

Synthesis Example 25

Synthesis of 1,4-Bis[2,2-bis[4-[bis(4-methylthiophenyl)amino]phenyl]vinyl]benzene (Compound 17)

1,4-Bis[2,2-bis(4-bromophenyl)vinyl]benzene (Compound 48; 506 mg, 0.67 mmol), 4,4'-Dimethylthiodiphenylamine (Compound 52; 860 mg, 3.29 mmol), Tris(dibenzylideneacetone) Dipalladium (92 mg, 0.10 mmol) and tertiary butoxysodium (483 mg, 5.03 mmol) were placed in a two-necked flask. Next, triterchary butylphosphine (91 mg, 0.45 mmol) and toluene (20 mL) were added, and the mixture was stirred at 90° C. for 15 hours. After the reaction, it was quenched with water (30 mL) and extracted 3 times with dichloromethane (25 mL). The organic layer was dried over magnesium sulfate, magnesium sulfate was filtered off, and the filtrate was concentrated under reduced pressure. The obtained crude product was subjected to silica gel column chromatography using toluene:hexane=5:4 as a developing solvent, and then concentrated. Further washing with dichloromethane:methanol=1:1 (100 mL) gave 650 mg (0.44 mmol) of compound 17 as a yellow solid in 65% yield.

$^1$H NMR (400 MHz, $CDCl_3$): δ 7.22 (d, $^3$J(H,H)=8.8 Hz, 4H), 7.18 (d, $^3$J(H,H)=8.8 Hz, 8H), 7.15 (d, $^3$J(H,H)=8.8 Hz, 8H), 7.07 (d, $^3$J(H,H)=8.8 Hz, 2H), 7.04 (d, $^3$J(H,H)=8.8 Hz, 8H), 7.02-6.95 (m, 16H), 6.86 (s, 4H), 6.81 (s, 2H), 2.47 (s, 12H), 2.44 (s, 12H).

General Formula [88]

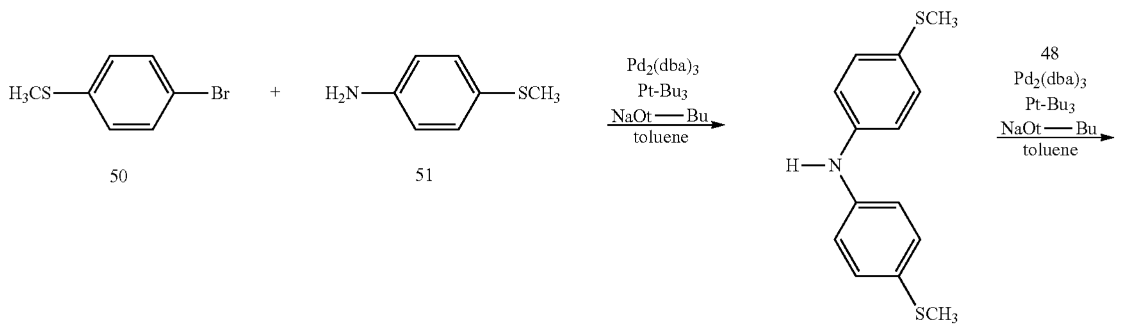

50 51 52

-continued

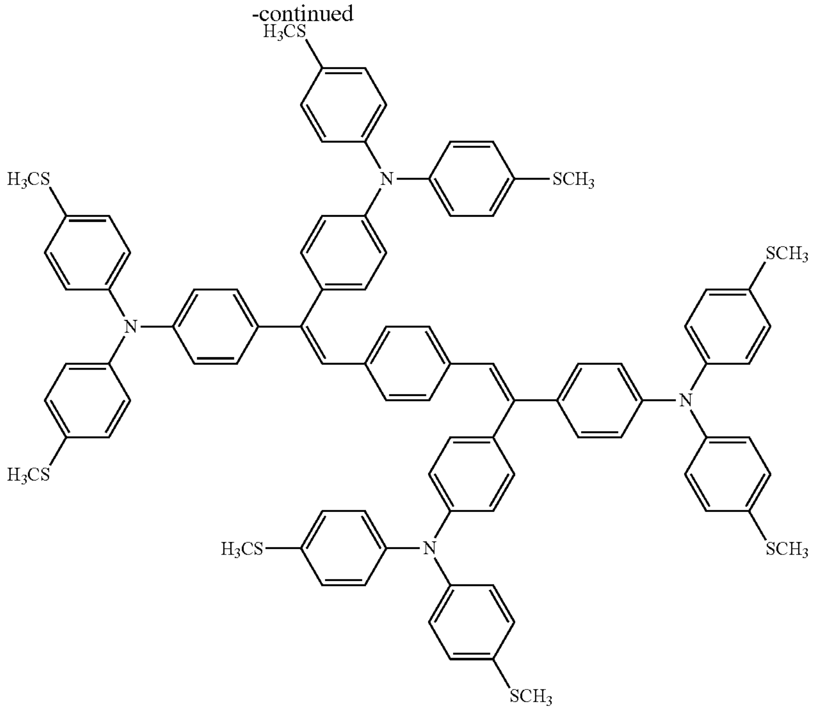

17

Synthesis Example 26

Synthesis of N, N-Bis(4-methoxyphenyl)-2-thiophenamine (Compound 54) 4,4'-Dimethoxydiphenylamine (Compound 49; 4.80 g, 21.0 mmol), Bis(dibenzylideneacetone) Palladium (181 mg, 0.315 mmol), tritersial butylphosphine (259 mg, 1.28 mmol) and tertiary butoxysodium (2.89 g, 30.1 mmol) was charged into a four-necked flask. Next, 2-bromothiophene (Compound 53; 4.12 g, 25.2 mmol) and toluene (60 mL) were added, and the mixture was stirred at 80° C. for 22 hours. After the reaction, quench with water (60 mL) and separate. Extracted three times with toluene (20 mL) and dried over magnesium sulfate. After the magnesium sulfate was filtered off, the filtrate was concentrated under reduced pressure. The obtained crude product was subjected to silica gel column chromatography using dichloromethane:hexane=1:1 as a developing solvent, and then concentrated to produce 5.26 g (16.9 mmol) of compound 54 in a yield of 80% as a yellow oil.

$^1H$ NMR (400 MHz, $CDCl_3$): δ 7.06 (d, $^3J(H,H)$=9.2 Hz, 4H), 6.85-6.78 (m, 6H), 6.53 (d, $^3J(H,H)$=2.0 Hz, 2H), 3.79 (s, 6H).

Synthesis Example 27

Synthesis of 5-[Bis (4-methoxyphenyl)amino]-2-thiophenecarboxyaldehyde (Compound 55)

N, N-Bis(4-methoxyphenyl)-2-thiopheneamine (Compound 54; 5.26 g, 16.9 mol) was dissolved in DMF (100 mL) and cooled with ice water. Phosphoryl oxychloride (3.00 mL, 32.9 mmol) was added, and the mixture was stirred at room temperature for 15 hours. After the reaction, the mixture was quenched with water (200 mL) and adjusted to pH=10 with a 25% aqueous sodium hydroxide solution. The organic layer was extracted 3 times with dichloromethane (40 mL) and dried over magnesium sulfate. After the magnesium sulfate was filtered off, the filtrate was concentrated under reduced pressure. The obtained crude product was purified by silica gel column chromatography using dichloromethane:ethyl acetate=1:1 as a developing solvent to obtain 5.01 g (14.8 mmol) of the target product 55 as a yellow oil in a yield of 87%.

General Formula [89]

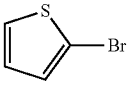

53

+

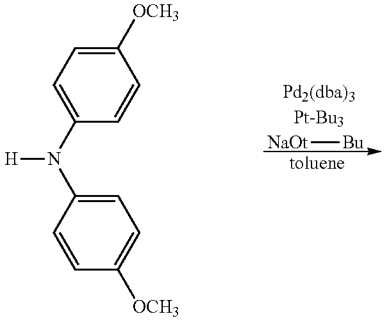

49

-continued

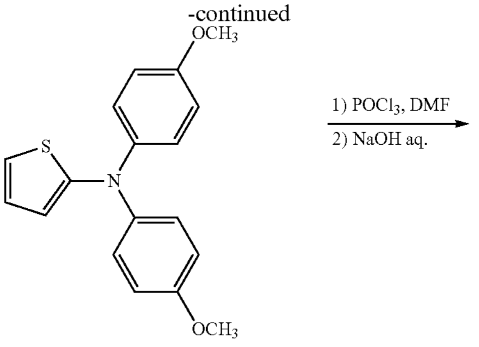

54

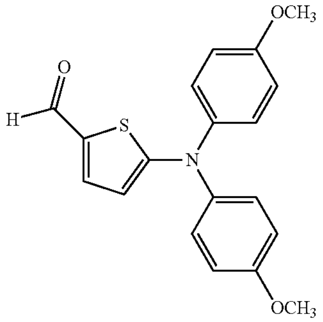

55

Synthesis Example 28

Synthesis of N, N-Bis(4-tolyl)-2-thiopheneamine (Compound 57)

4,4'-Ditrilamine (Compound 56; 8.00 g, 40.6 mmol), 2-Bromothiophene (Compound 53; 9.26 g, 56.8 mmol), tertiary butoxysodium (5.46 g, 56.8 mmol), triterly butylphosphine (Compound 53; 9.26 g, 56.8 mmol) 492 mg, 2.43 mmol) and was charged into a four-necked flask. Next, bis (dibenzylideneacetone) palladium (350 mg, 0.608 mmol) and toluene (120 mL) were added, and the mixture was stirred at 80° C. for 5 hours. 2-Bromothiophene (Compound 53; 1.00 g, 6.13 mmol) was added and stirred for an additional 2 hours. After the reaction, quench with water (100 mL) and separate. It was extracted twice with toluene (20 mL) and dried over magnesium sulfate. After the magnesium sulfate was filtered off, the filtrate was concentrated under reduced pressure. The obtained crude product was subjected to silica gel column chromatography using ethyl acetate:hexane=1:20 as a developing solvent, and then concentrated to obtain 6.00 g (21.5 mmol) of compound 57 as a yellow oil in a yield of 53%.

$^1H$ NMR (400 MHz, $CDCl_3$): δ 7.08 (d, $^3J$(H,H)=8.8 Hz, 4H), 7.04 (d, $^3J$(H,H)=8.8 Hz, 4H), 6.94 (d, $^3J$(H,H)=4.4 Hz, 1H), 6.94 (d, $^3J$(H,H)=5.6 Hz, 1H), 6.87 (dd, $^3J$(H,H)=5.6 Hz, $^3J$(H,H)=3.6 Hz, 1H), 6.67 (d, $^3J$(H,H)=3.6 Hz, 1H), 2.33 (s, 6H).

Synthesis Example 29

Synthesis of 5-[Bis (4-tolyl) amino]-2-thiophenecarboxyaldehyde (Compound 58)

N, N-Bis(4-tolyl)-2-thiopheneamine (Compound 57; 5.00 g, 17.9 mol) was dissolved in DMF (80 mL) and cooled with ice water. Phosphoryl oxychloride (3.30 mL, 36.0 mmol) was added, and the mixture was stirred at room temperature for 17 hours. After the reaction, the mixture was quenched with water (40 mL) and adjusted to pH=10 with a 25% aqueous sodium hydroxide solution. Diethyl ether (100 mL) was added, and the organic layer was washed three times with saturated brine (100 mL) and dried over magnesium sulfate. After the magnesium sulfate was filtered off, the filtrate was concentrated under reduced pressure. The obtained crude product was purified by silica gel column chromatography using hexane:ethyl acetate=15:1 as a developing solvent, and 3.50 g (11.4 mmol) of the target product 58 was obtained as an orange oil in a yield of 64%.

General Formula [90]

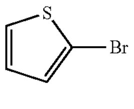

53

+

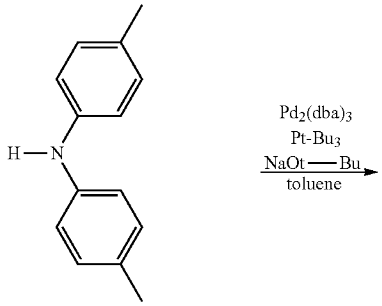

56

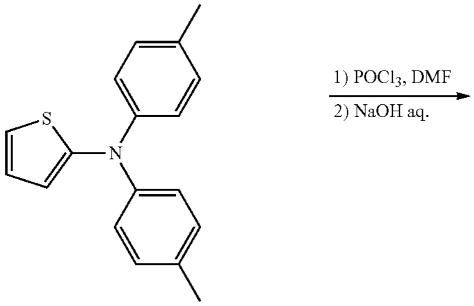

57

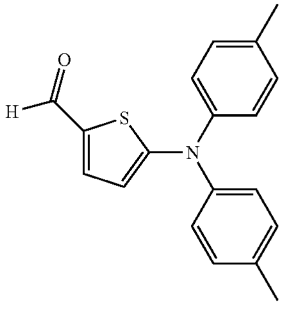

58

Synthesis Example 30

Synthesis of 5,5'-[(E, E)-1,4-Phenylene-bis(ethen-2, 1-diyl)]-Bis[N, N-bis(4-methoxyphenyl)-thiophen-2-amine] (Compound 19)

THF with p-bis (diethylphosphono) xylene (Compound 39; 615 mg, 1.63 mmol) and 5-[bis (4-methoxyphenyl) amino]-2-thiophenecarboxyaldehyde (Compound 55; 1.10 g, 3.26 mmol) It was dissolved in (80 mL) and cooled with ice water. Tarshary butoxypotassium (733 mg, 6.53 mmol) was added to the solution, and the mixture was stirred at room temperature for 2 hours. After the reaction, water (120 mL) was quenched to precipitate a yellow solid. The precipitated solid was collected by filtration and washed with water (80 mL). The crude product obtained was dissolved in dichloromethane (100 mL) and filtered through a silica pad. Thermal recrystallization with toluene (40 mL) gave 705 mg (0.94 mmol) of compound 19 as an orange solid in 58% yield.

$^1$H NMR (400 MHz, $CDCl_3$): δ 7.30 (s, 4H), 7.13 (d, $^3$J(H,H)=8.8 Hz, 8H), 7.07 (d, $^3$J(H,H)=16.0 Hz, 2H), 6.84 (d, $^3$J(H,H)=8.8 Hz, 8H), 6.73 (d, $^3$J(H,H)=4.0 Hz, 2H), 6.55 (d, $^3$J(H,H)=16.0 Hz, 2H), 6.29 (d, $^3$J(H,H)=3.6 Hz, 2H), 3.80 (s, 12H).

General Formula [91]

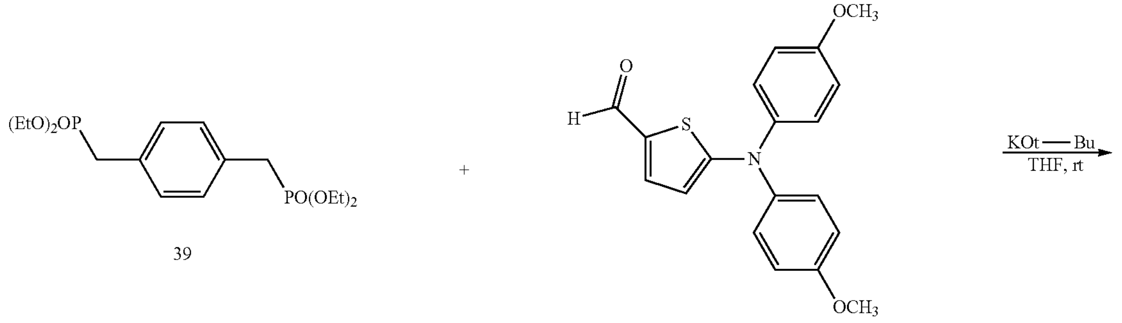

39

55

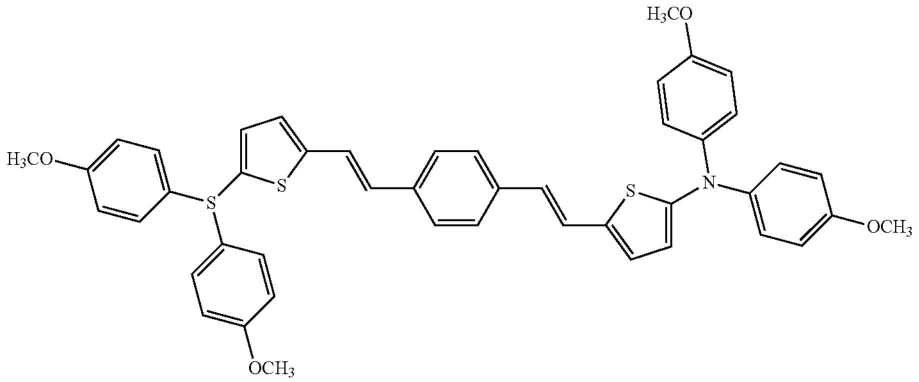

19

Synthesis Example 31

Synthesis of 5,5'-[(E, E)[1,1'-Biphenyl]-4,4'-diyl-bis (ethene-2,1-diyl)]-bis[N, N-bis(4-methoxyphenyl) Thiophene-2-amine] (Compound 21)

4,4'-bis(diethylphosphonomethyl) biphenyl (Compound 46; 601 mg, 1.32 mmol) and 5-[bis(4-methoxyphenyl) amino]-2-thiophenecarboxyaldehyde (Compound 55; 900 mg, 2.65) mmol) was dissolved in THF (40 mL) and cooled with ice water. Tarshary butoxypotassium (605 mg, 5.39 mmol) was added to the solution, and the mixture was stirred at room temperature for 3 hours. After the reaction, the orange solid was precipitated by quenching with water (80 mL). The precipitated solid was collected by filtration and washed with water (40 mL) and methanol (40 mL). Silica gel column chromatography of the obtained crude product using dichloromethane:toluene=1:1 as the developing solvent gave 730 mg (0.88 mmol) of compound 21 as an orange solid in a yield of 67%.

$^{1}$H NMR (400 MHz, $CDCl_3$): δ 7.55 (d, $^{3}$J(H,H)=8.4 Hz, 4H), 7.43 (d, $^{3}$J(H,H)=8.4 Hz, 4H), 7.14 (d, $^{3}$J(H,H)=8.4 Hz, 8H), 7.13 (d, $^{3}$J(H,H)=16.4 Hz, 2H), 6.84 (d, $^{3}$J(H,H)=8.4 Hz, 8H), 6.76 (d, $^{3}$J(H,H)=4.4 Hz, 2H), 6.61 (d, $^{3}$J(H,H)=16.4 Hz, 2H), 6.30 (d, $^{3}$J(H,H)=3.6 Hz, 2H), 3.80 (s, 12H).

General Formula [91]

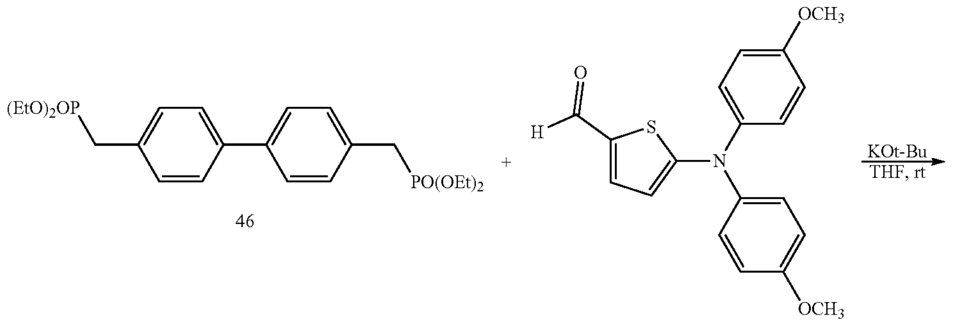

46

55

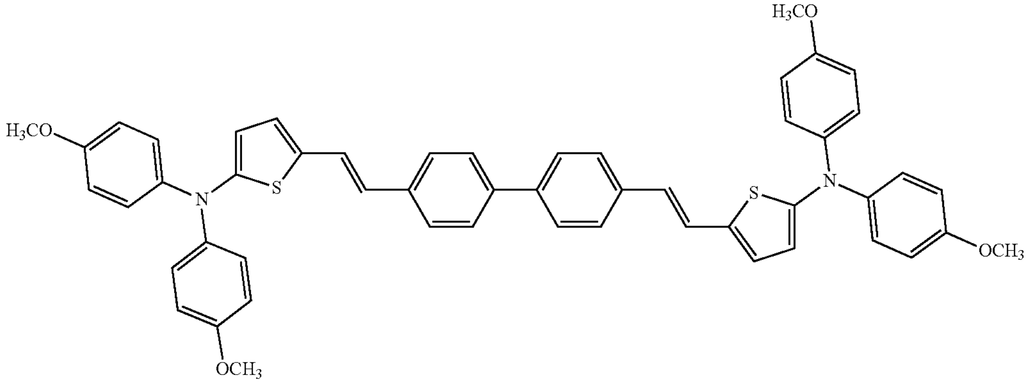

21

Synthesis Example 32

Synthesis of 5,5'-[(E, E)[1,1'-Biphenyl]-4,4'-diyl-bis (ethen-2,1-diyl)]-bis[N, N-bis(4-tolyl) thiophene-2-Amine] (Compound 22)

4,4'-bis (diethylphosphonomethyl) biphenyl (Compound 46; 907 mg, 2.00 mmol) and 5-[bis (4-tolyl) amino]-2-thiophenecarboxyaldehyde (Compound 58; 1.43 g, 4.61 mmol)) Was dissolved in THF (60 mL) and cooled with ice water. Tarshary butoxypotassium (907 mg, 8.08 mmol) was added to the solution, and the mixture was stirred at room temperature for 2 hours. After the reaction, water (120 mL) was quenched to precipitate an orange solid. The precipitated solid was collected by filtration and washed with water (150 mL) and methanol (150 mL). Thermal recrystallization of the obtained crude product with toluene gave 1.27 g (1.66 mmol) of compound 22 as an orange solid in a yield of 83%.

$^1$H NMR (400 MHz, $CDCl_3$): δ 7.55 (d, $^3$J(H,H)=8.4 Hz, 4H), 7.44 (d, $^3$J(H,H)=8.4 Hz, 4H), 7.14 (d, $^3$J(H,H)=16.0 Hz, 2H), 7.09 (s, 16H), 6.79 (d, $^3$J(H,H)=4.4 Hz, 2H), 6.66 (d, $^3$J(H,H)=16.4 Hz, 2H), 6.44 (d, $^3$J(H,H)=4.0 Hz, 2H), 2.32 (s, 12H).

General Formula [93]

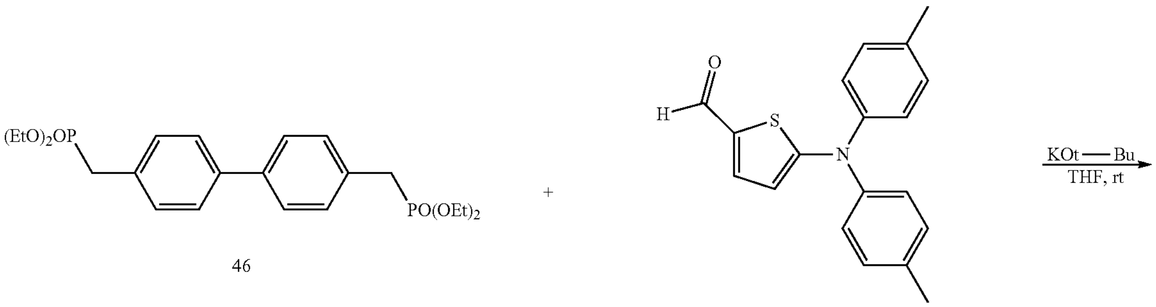

46

58

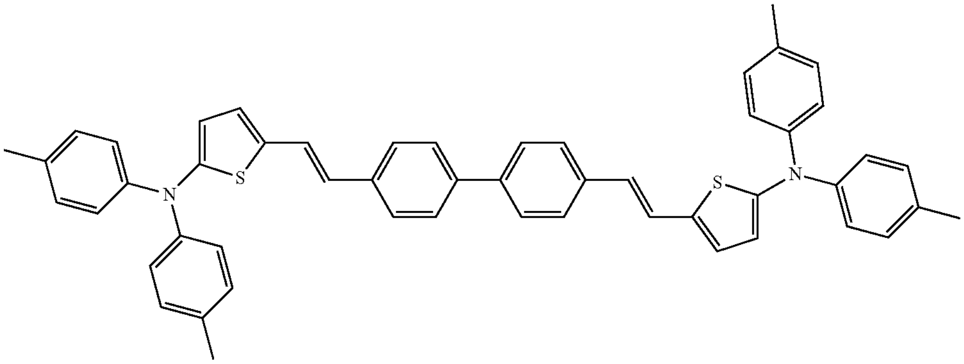

22

Synthesis Example 33

Synthesis of trans-1,2-Di(5-bromothiophen-2-yl) Ethene (Compound 60)

Trans-1,2-di (2-thienyl) ethylene (Compound 59; 1.92 g, 10.0 mmol) is dissolved in DMF (100 mL), N-bromosuccinimide (3.56 g, 20.0 mmol) is added, and 2 at room temperature. Stirred for hours. After quenching with saturated aqueous sodium hydrogen carbonate (120 mL), the mixture was extracted twice with dichloromethane (50 mL), and the organic layer was washed twice with water (50 mL) and once with saturated brine (50 mL). The organic layer was dried over magnesium sulfate, filtered off, and the filtrate was concentrated under reduced pressure to give 3.41 g (9.73 mmol) of compound 60 as a yellow solid in a yield of 97%.

$^1$H NMR (400 MHz, $CDCl_3$): δ 6.94 (d, $^3$J(H,H)=3.6 Hz, 2H), 6.80 (s, 2H), 6.77 (d, $^3$J(H,H)=3.6 Hz, 2H).

General Formula [94]

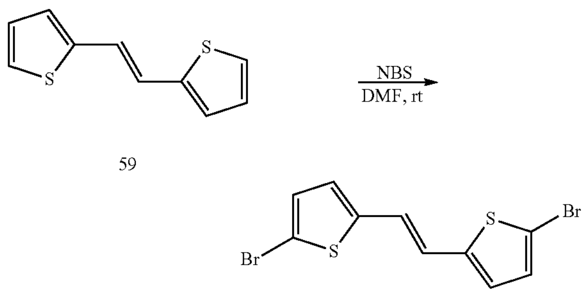

59

60

Synthesis Example 34

Synthesis of (E)-5,5-(Ethen-1,2-diyl)-bis(N, N-bis (4-methoxyphenyl)-thiophen-2-amine) (Compound 23)

trans-1,2-Di(5-bromothiophen-2-yl) Ethene (Compound 60; 876 mg, 2.50 mmol), 4,4'-dimethoxydiphenylamine (Compound 49; 1.27 g, 5.55 mmol), bis (di) Bendylideneacetone) palladium (45 mg, 0.078 mmol) and tertiary butoxysodium (752 mg, 7.83 mmol) were charged into a two-necked flask. Next, triterchary butylphosphine (61 mg, 0.30 mmol) and toluene (15 mL) were added, and the mixture was stirred at 100° C. for 5 hours. After the reaction, quench with water (20 mL) and separate. Extracted three times with toluene (15 mL) and dried over magnesium sulfate. After the magnesium sulfate was filtered off, the filtrate was concentrated under reduced pressure. The obtained crude product was subjected to silica gel column chromatography using dichloromethane:hexane=2:1 as a developing solvent, and 864 mg (1.34 mmol) of Compound 23 was obtained as an orange solid in a yield of 53%.

$^1$H NMR (400 MHz, DMSO-d6): δ 7.54 (d, $^3$J(H,H)=8.4 Hz, 8H), 7.35 (d, $^3$J(H,H)=8.4 Hz, 8H), 7.18 (d, $^3$J(H,H)=3.6 Hz, 2H), 7.10 (s, 2H), 6.67 (d, $^3$J(H,H)=4.0 Hz, 2H), 4.23 (s, 12H).

General Formula [95]

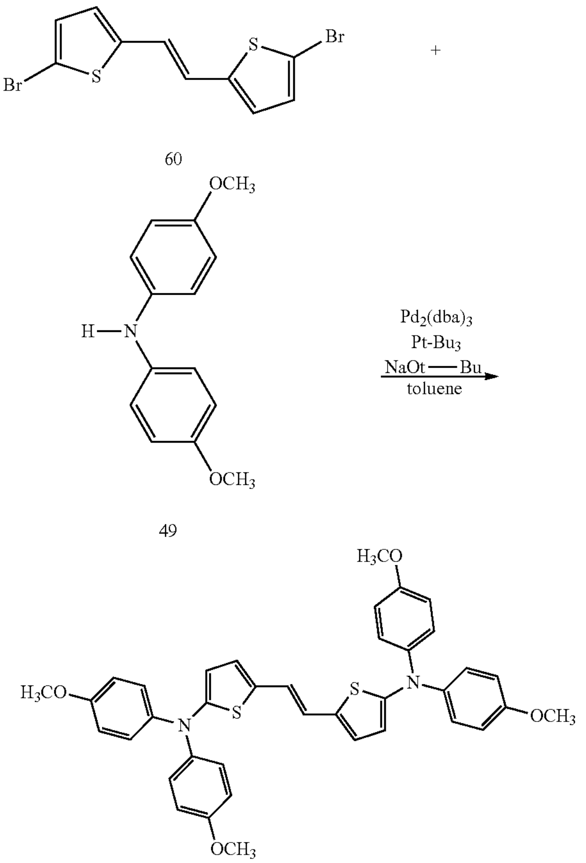

60

49

23

Synthesis Example 35

Synthesis of (E)-5,5'-(Ethen-1,2-diyl) bis (N, N-bis (4-tolyl) thiophen-2-amine) (Compound 24)

trans-1,2-Di(5-bromothiophen-2-yl) ethene (Compound 60; 351 mg, 1.00 mmol), 4,4'-ditrilamine (Compound 56; 432 mg, 2.19 mmol), bis (dibenzylidene) Alpine) palladium (17 mg, 0.030 mmol) and tertiary butoxysodium (284 mg, 2.96 mmol) were charged into a two-necked flask. Next, triterchary butylphosphine (27 mg, 0.13 mmol) and toluene (5 mL) were added, and the mixture was stirred at 100° C. for 3 hours. After the reaction, quench with water (10 mL) and separate. Extraction was performed three times with toluene (5 mL) and the organic layer was washed with water (10 mL) and saturated brine (10 mL). The organic layer was dried over magnesium sulfate, filtered off, and the filtrate was concentrated under reduced pressure. The obtained crude product was filtered using a silica pad at dichloromethane:hexane=1:1 and then subjected to silica gel column chromatography using dichloromethane:hexane=1:4 as a developing solvent to obtain 272 mg (0.47 mmol).) Compound 24 was obtained as an orange solid in a yield of 47%.

$^1$H NMR (400 MHz, DMSO-$d_6$): δ 7.58 (d, $^3$J(H,H)=8.4 Hz, 8H), 7.47 (d, $^3$J(H,H)=8.4 Hz, 8H), 7.26 (d, $^3$J(H,H)=4.0 Hz, 2H), 7.19 (s, 2H), 6.85 (d, $^3$J(H,H)=3.6 Hz, 2H), 2.74 (s, 12H).

General Formula [96]

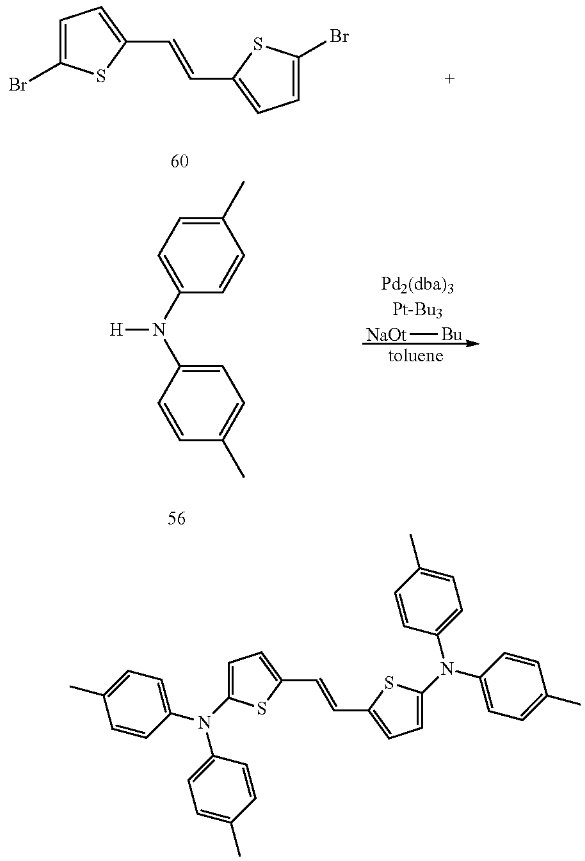

60

56

24

Synthesis Example 36

Synthesis of 5-(4-(Bis(4-methoxyphenyl)amino) phenyl) Thiophene-2-carbaldehyde (Compound 72)

4-Bromo-4', 4"-dimethoxytriphenylamine (Compound 70; 5.00 g, 13.0 mmol)), palladium acetate (60 mg, 0.27 mmol), tricyclohexylphosphonium tetrafluoroborate (183 mg, 0.50 mmol)), Pivalic acid (401 mg, 3.9 mmol), and potassium carbonate (3.60 g, 26.0 mmol) were placed in a two-necked flask. Next, 2-thiophenecarboxyaldehyde (Compound 71; 3.6 mL, 40 mmol) and toluene (50 mL) were added, and the mixture was stirred at 130° C. for 6 hours. After air cooling, it was quenched with water (50 mL) and separated. The organic layer was extracted three times with toluene (20 mL), washed once with saturated brine (50 mL), and dried over magnesium sulfate. After the magnesium sulfate was filtered off, the filtrate was concentrated under reduced pressure. The obtained crude product was purified by silica gel column chromatography using a mixed solvent of dichloromethane:hexane=2:1 to obtain 3.90 g (9.39 mmol) of compound 72 as an orange solid in a yield of 72%.

$^1$H NMR (400 MHz, $CDCl_3$): δ 9.83 (s, 1H), 7.69 (d, $^3$J(H,H)=4.0 Hz, 1H), 7.46 (d, $^3$J(H,H)=8.8 Hz, 2H), 7.25 (d, $^3$J(H,H)=4.0 Hz, 1H), 7.09 (d, $^3$J(H,H)=9.2 Hz, 4H), 6.90 (d, $^3$J(H,H)=8.8 Hz, 2H), 6.86 (d, $^3$J(H,H)=9.2 Hz, 4H), 3.81 (s, 6H).

General Formula [97]

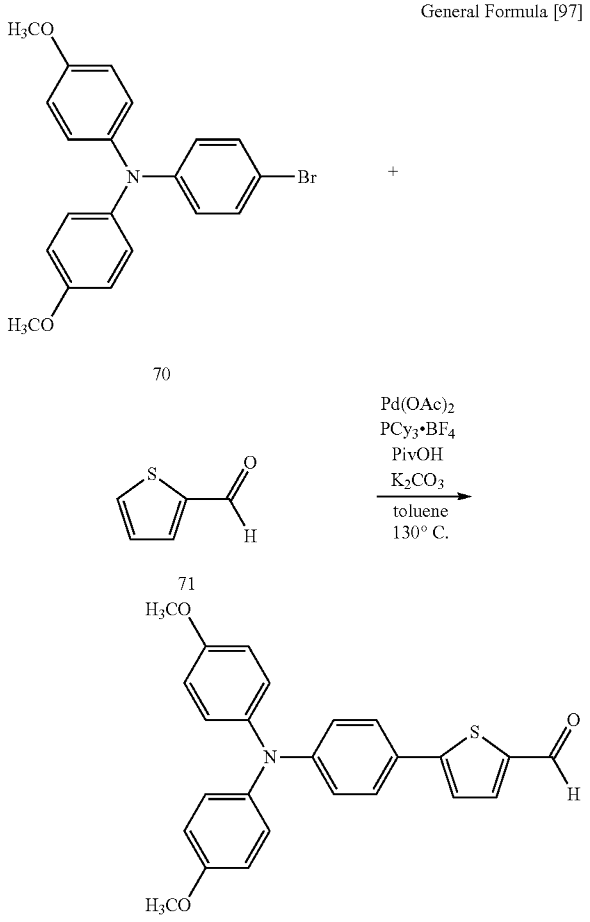

70

71

72

Synthesis Example 37

Synthesis of 7-(4-(Bis(4-methoxyphenyflamino) phenyl)-2,3-dihydrothieno[3,4-b] [1,4]dioxine-5-carbaldehyde (Compound 74)

4-Bromo-4', 4"-dimethoxytriphenylamine (Compound 70; 2.33 g, 6.06 mmol)), palladium acetate (20 mg, 0.089 mmol), tricyclohexylphosphonium tetrafluoroborate (69 mg, 0.19 mmol)), Pivalic acid (56 mg, 0.55 mmol), and potassium carbonate (1.27 g, 9.19 mmol) were placed in a two-necked flask. Next, 3,4-ethylenedioxythiophene-2-carboxyaldehyde (Compound 73; 824 mg, 4.84 mmol) and toluene (6 mL) were added, and the mixture was stirred at 130° C. for 18 hours. After air cooling, the mixture was quenched with water (6 mL) and separated. The organic layer was extracted three times with toluene (8 mL), washed once with saturated brine (6 mL), and dried over magnesium sulfate. After the magnesium sulfate was filtered off, the filtrate was concentrated under reduced pressure. The obtained crude product was purified by silica gel column chromatography using a mixed solvent of ethyl acetate: hexane=1:2 to obtain 1.40 g (2.96 mmol) of Compound 1 as an orange solid in a yield of 61%.

$^1$H NMR (400 MHz, $CDCl_3$): δ 9.88 (s, 1H), 7.58 (d, $^3$J(H,H)=8.4 Hz, 2H), 7.08 (d, $^3$J(H,H)=9.2 Hz, 4H), 6.89 (d, $^3J$(H,H)=9.2 Hz, 2H), 6.85 (d, $^3J$(H,H)=8.8 Hz, 4H), 4.37 (d, $^3J$(H,H)=14.0 Hz, 4H), 3.80 (s, 6H).

General Formula [98]

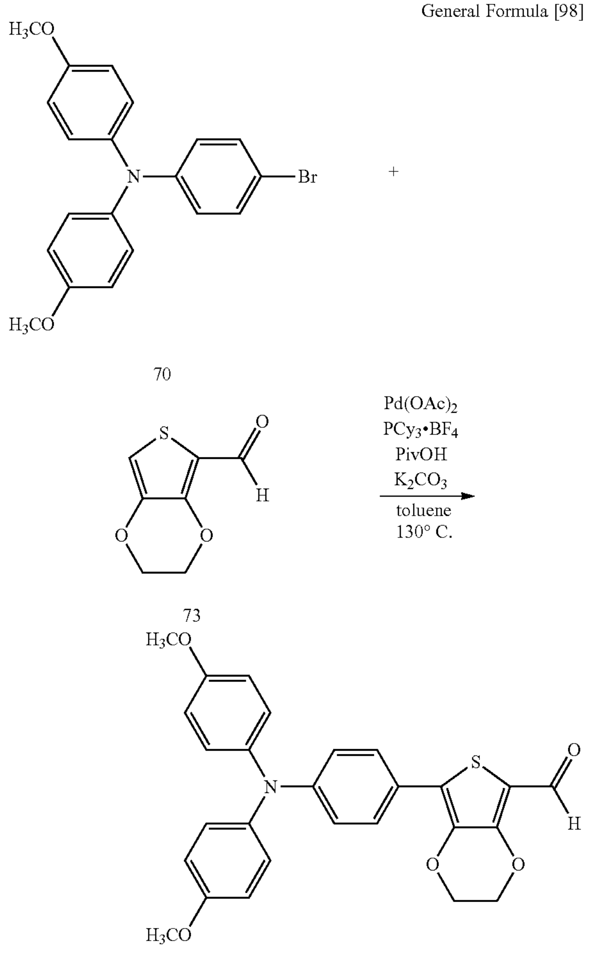

70

73

74

Synthesis Example 38

Synthesis of 3,5-Bis(4-(bis(4-methoxyphenyflamino)phenyl) Thiophene-2-carbaldehyde (Compound 75)

4-Bromo-4', 4"-dimethoxytriphenylamine (Compound 70; 760 mg, 1.98 mmol)), palladium acetate (20 mg, 0.089 mmol), tricyclohexylphosphonium tetrafluoroborate (60 mg, 0.16 mmol)), Pivalic acid (128 mg, 1.25 mmol), and potassium carbonate (554 mg, 4.01 mmol) were placed in a two-necked flask. Next, 5-(4-(bis (4-methoxyphenyl) amino) phenyl) thiophene-2-carbaldehyde (Compound 72; 783 mg, 1.88 mmol) and toluene (20 mL) were added and at 130° C. for 45 hours. Stirred. Then, palladium acetate (20 mg, 0.089 mmol), tricyclohexylphosphonium tetrafluoroborate (60 mg, 0.16 mmol) and pivalic acid (117 mg, 1.15 mmol) were added, and the mixture was further stirred for 24 hours. After air cooling, it was quenched with water (20 mL) and separated. The organic layer was extracted three times with toluene (10 mL), washed once with saturated brine (10 mL), and dried over magnesium sulfate. After the magnesium sulfate was filtered off, the filtrate was concentrated under reduced pressure. The obtained crude product was purified by silica gel column chromatography using a mixed solvent of toluene→toluene:ethyl acetate=50:1, to obtain 445 mg (0.62 mmol) of Compound 1 as an orange solid in a yield of 33%.

$^1$H NMR (400 MHz, $CDCl_3$): δ 9.84 (s, 1H), 7.47 (d, $^3J$(H,H)=8.8 Hz, 2H), 7.24 (s, 1H), 7.30 (d, $^3J$(H,H)=8.8 Hz, 2H), 7.12 (d, $^3J$(H,H)=9.2 Hz, 4H), 7.10 (d, $^3J$(H,H)=9.2 Hz, 4H), 6.96 (d, $^3J$(H,H)=8.4 Hz, 2H), 6.90 (d, $^3J$(H,H)=8.4 Hz, 2H), 6.87 (d, $^3J$(H,H)=8.8 Hz, 4H), 6.86 (d, $^3J$(H,H)=9.2 Hz, 4H), 3.81 (s, 12H).

General Formula [99]

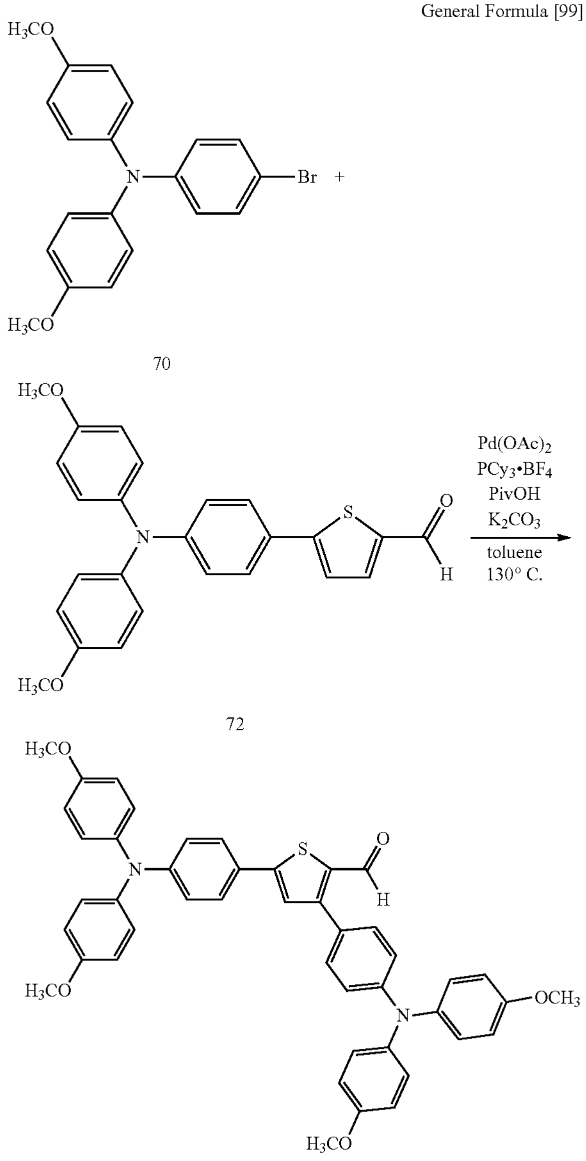

70

72

75

Synthesis Example 39

4,4'-(((1E, 1'E)-1,4-Phenylene-bis(ethen-2,1-diyl))-bis (thiophene-5,2-diyl))-bis(N, N-bis(Synthesis of 4-methoxyphenyl) aniline) (Compound 76) p-bis (diethylphosphono)

xylene (Compound 39; 757 mg, 2.00 mmol) and 5-(4-(bis (4-methoxyphenyl) amino) phenyl) thiophene-2-carbaldehyde (Compound 72; 1.69 g, 4.07 mmol) was dissolved in THF (60 mL) and cooled with ice water. Tarshary butoxy-potassium (900 mg, 8.02 mmol) was added to the solution, and the mixture was stirred at room temperature for 3 hours. After the reaction, water (180 mL) was quenched and the mixture was stirred while cooling with ice to precipitate an orange solid. The precipitated solid was collected by filtration and washed with water (60 mL) and methanol (60 mL). The obtained crude product was purified by silica gel column chromatography using a mixed solvent of dichloromethane:hexane=1:1>2:1 to obtain 1.42 g (1.58 mmol) of compound 76 as an orange solid in a yield of 79%.

$^1H$ NMR (400 MHz, $CDCl_3$): δ 7.43 (s, 4H), 7.41 (d, $^3J(H,H)$=8.8 Hz, 4H), 7.20 (d, $^3J(H,H)$=16.0 Hz, 2H), 7.10-7.04 (m, 10H), 6.99 (d, $^3J(H,H)$=3.6 Hz, 2H), 6.92 (d, $^3J(H,H)$=8.8 Hz, 4H), 6.86 (d, $^3J(H,H)$=16.0 Hz, 2H), 6.84 (d, $^3J(H,H)$=9.2 Hz, 8H), 3.81 (s, 12H).

General Formula [100]

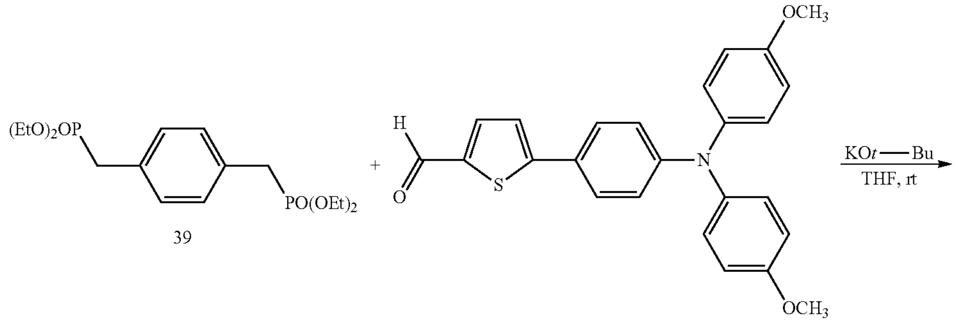

39

72

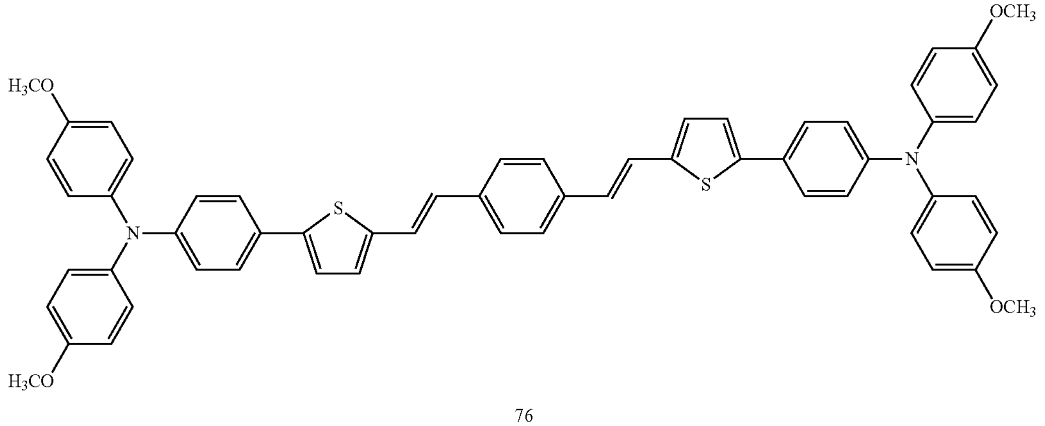

76

Synthesis Example 40

Synthesis of 4,4'-(((1E, 1'E)-1,4-phenylene-bis(ethen-2,1-diyl)))-bis(2,3-dihydrothieno[3,4-b]-[1,4] Dioxin-7,5-diyl))-bis(N, N-bis ((4-methoxyphenyl) aniline) (Compound 77) p-bis (diethylphosphono) xylene (Compound 39; 730 mg, 1.93 mmol) and 7-(4-(bis (4 -methoxy phenyl) amino) phenyl)-2,3-dihydrothieno[3,4-b] [1,4] Dioxine-5-carbaldehyde (Compound 74; 1.92 g, 4.05 mmol) was dissolved in THF (20 mL). To this solution was added 1 M tertiary butoxypotassium/THF solution (7.7 mL, 7.7 mmol), and the mixture was stirred at room temperature for 0.7 hours. After the reaction, the mixture was quenched with water (50 mL), extracted three times with dichloromethane (40 mL), and the organic layer was washed with saturated brine. The organic layer was dried over magnesium sulfate, filtered off, and the filtrate was concentrated under reduced pressure. The obtained crude product was purified by silica gel column chromatography using a mixed solvent of dichloromethane: hexane=1:1 to obtain 1.31 g (1.29 mmol) of Compound 77 as an orange solid in a yield of 67%.

$^1H$ NMR (400 MHz, $CDCl_3$): δ 7.53 (d, $^3J(H,H)$=8.4 Hz, 4H), 7.40 (s, 4H), 7.18 (d, $^3J(H,H)$=16.0 Hz, 2H), 7.06 (d, $^3J(H,H)$=8.4 Hz, 8H), 6.92 (d, $^3J(H,H)$=8.8 Hz, 4H, 6.83 (d, $^3J(H,H)$=8.8 Hz, 8H)), 6.79 (d, $^3J(H,H)$=16.0 Hz, 2H), 4.31 (s, 8H), 3.80 (s, 12H).

General Formula [101]

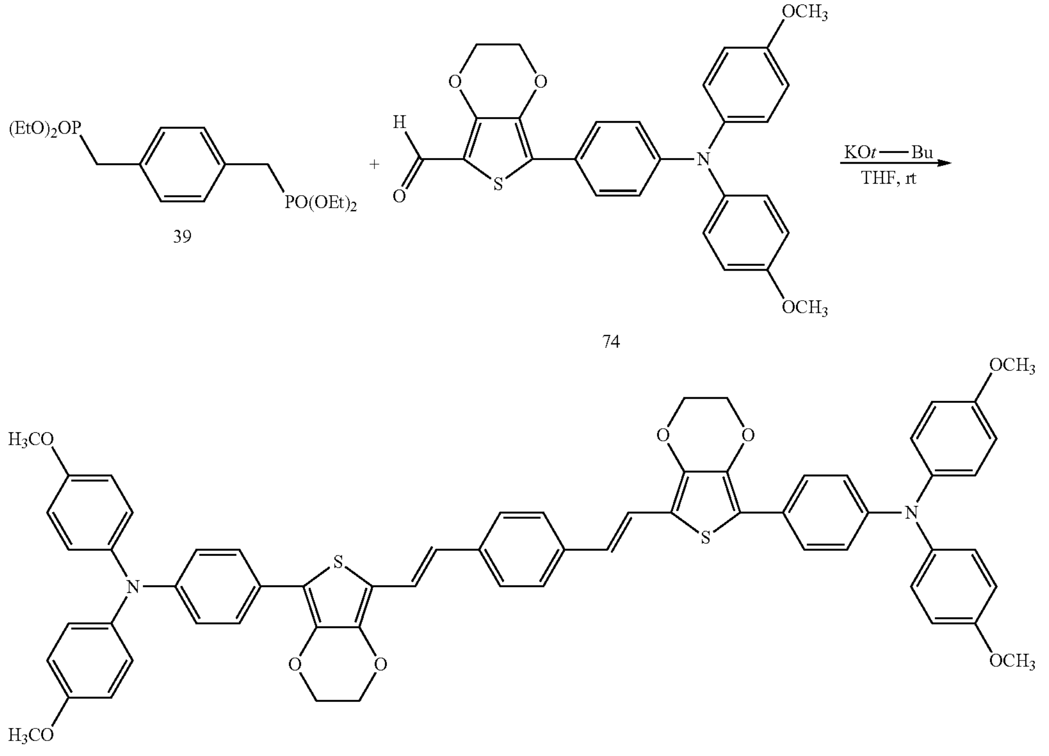

39

74

77

Synthesis Example 41

Synthesis of 4,4', 4", 4'''-(((1E, 1'E, 1"E, 1'''E)-Benzene-1,2,4,5-tetrayltetrakis (ethene)-2,1-diyl)) Tetrakis (thiophene-5,2-diyl)) Tetrakis(N, N-bis(4-methoxyphenyl)aniline) (Compound 78)

1,2,4,5-Tetrakis(diethylphosphonomethyl) Benzene (Compound 44; 273 mg, 0.40 mmol) and 5-(4-(bis(4-methoxyphenyl)amino)phenyl) thiophene-2-carbaldehyde (Compound 72; 930 mg, 1.96 mmol) was dissolved in THF (30 mL) and cooled with ice water. Tarshary butoxypotassium (898 mg, 8.00 mmol) was added to the solution, and the mixture was stirred at room temperature for 7 hours. After the reaction, water (180 mL) was quenched, dichloromethane (50 mL) was added, and the liquid was separated. The organic layer was extracted three times with dichloromethane (25 mL) and then washed with saturated brine (50 mL). The organic layer was dried over magnesium sulfate, filtered off, and the filtrate was concentrated under reduced pressure. The obtained crude product was subjected to silica gel column chromatography using a mixed solvent of toluene: ethyl acetate=49:1 as a developing solvent to obtain 724 mg (0.42 mmol) of compound 78 as a red solid in a yield of 42%.

$^1$H NMR (400 MHz, $CDCl_3$): δ 7.68 (s, 2H), 7.42 (d, $^3$J(H,H)=8.8 Hz, 8H), 7.19 (d, $^3$J(H,H)=5.6 Hz, 8H), 7.12-7.04 (m, 24H), 6.92 (d, $^3$J(H,H)=8.8 Hz, 8H), 6.84 (d, $^3$J(H,H)=9.2 Hz, 16H), 3.80 (s, 24H).

General Formula [102]

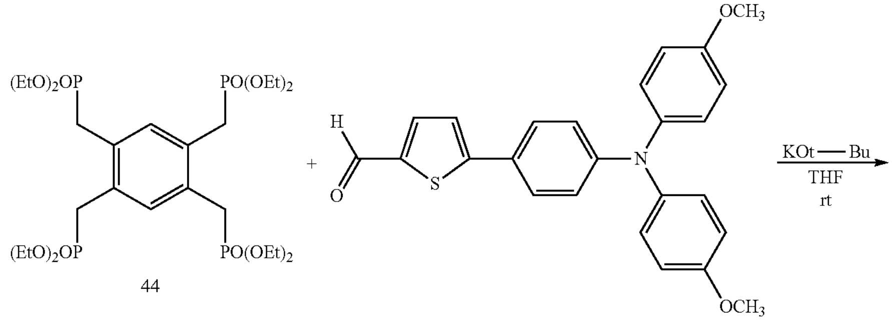

44

72

-continued

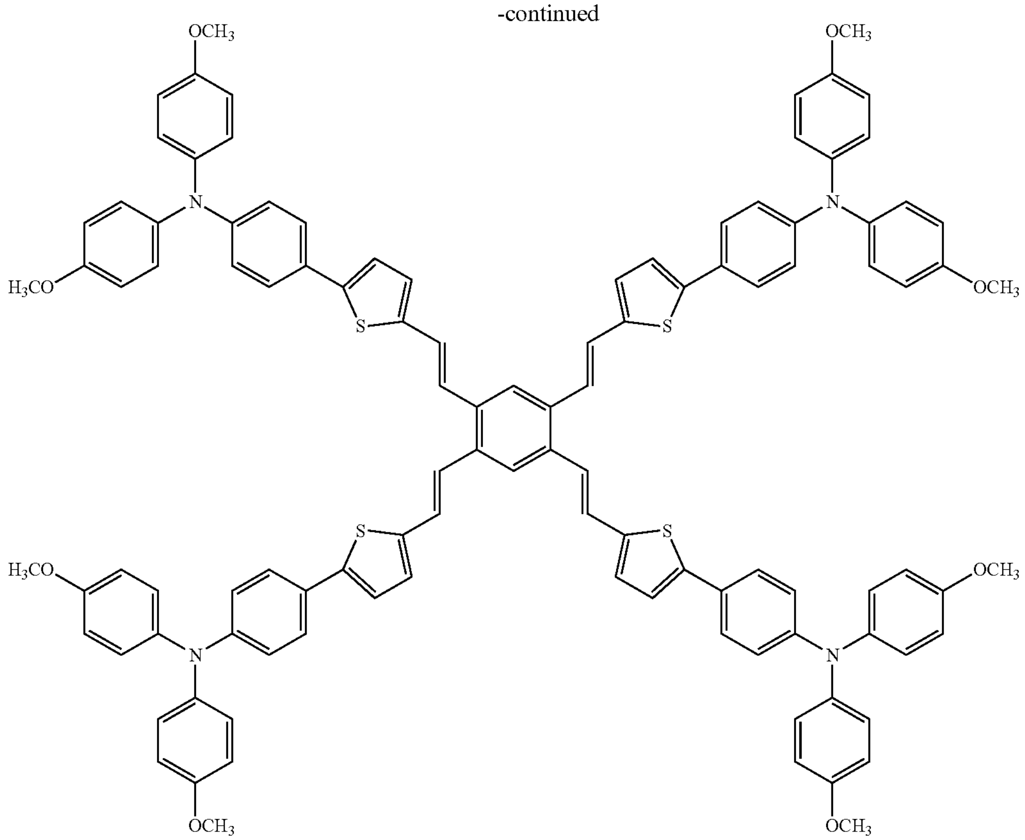

78

Synthesis Example 42

Synthesis of 4,4',4'',4'''-(((1E, 1'E, 1''E, 1'''E)-Benzene-1,2,4,5-Tetrayltetrakis (Eten)-2,1-diyl)) Tetrakis (2,3-dihydrothieno[3,4-b] [1,4] dioxine-7,5-diyl)) Tetrakis (N, N-bis((4-methoxyphenyl)) aniline) (Compound 79)

1,2,4,5-Tetrakis(diethylphosphonomethyl) Benzene (Compound 44; 678 mg, 1.00 mmol) and 7-(4-(bis (4-methoxyphenyl) amino) phenyl)-2,3-dihydrothieno [3,4-b] [1,4] Dioxin-5-carbaldehyde (Compound 74; 1.68 g, 4.04 mmol) was dissolved in THF (75 mL) and cooled with ice water. To this solution was added 1 M tertiary butoxypotassium/THF solution (2.0 mL, 2.0 mmol) and stirred at room temperature for 2 hours. 1 M tertiary butoxypotassium/THF solution (300 μL, 0.3 mmol) was added and stirred for an additional 14 hours. After the reaction, the mixture was quenched with water (30 mL) and concentrated hydrochloric acid was added to adjust the pH to 2. The organic layer was extracted twice with dichloromethane (25 mL) and then washed with saturated brine (20 mL). The organic layer was dried over magnesium sulfate, filtered off, and the filtrate was concentrated under reduced pressure. The obtained crude product was subjected to silica gel column chromatography using a mixed solvent of toluene:ethyl acetate=50:1→40:1 as a developing solvent to obtain 455 mg (0.23 mmol) of compound 79 as a red solid in a yield of 58%.

$^1$H NMR (400 MHz, $CDCl_3$): δ 7.67 (s, 2H), 7.54 (d, $^3$J(H,H)=8.8 Hz, 8H), 7.20 (d, $^3$J(H,H)=16.0 Hz, 4H), 7.11 (d, $^3$J(H,H)=16.0 Hz, 4H), 7.06 (d, $^3$J(H,H)=9.2 Hz, 16H), 6.92 (d, $^3$J(H,H)=8.8 Hz, 8H), 6.82 (d, $^3$J(H,H)=9.2 Hz, 16H), 4.33 (d, $^3$J(H,H)=4.0 Hz, 16H), 3.80 (s, 24H).

General Formula [103]

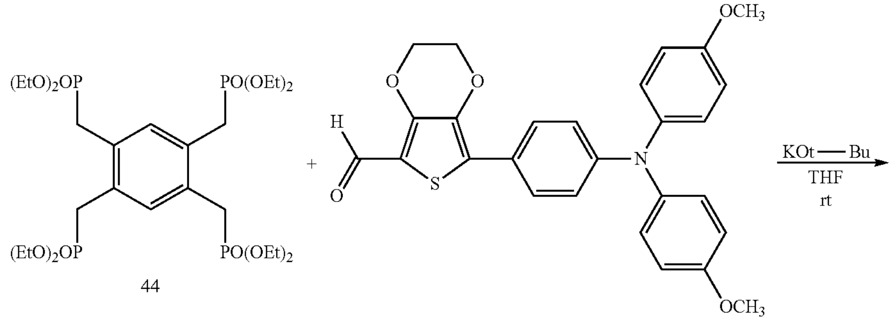

44

74

-continued

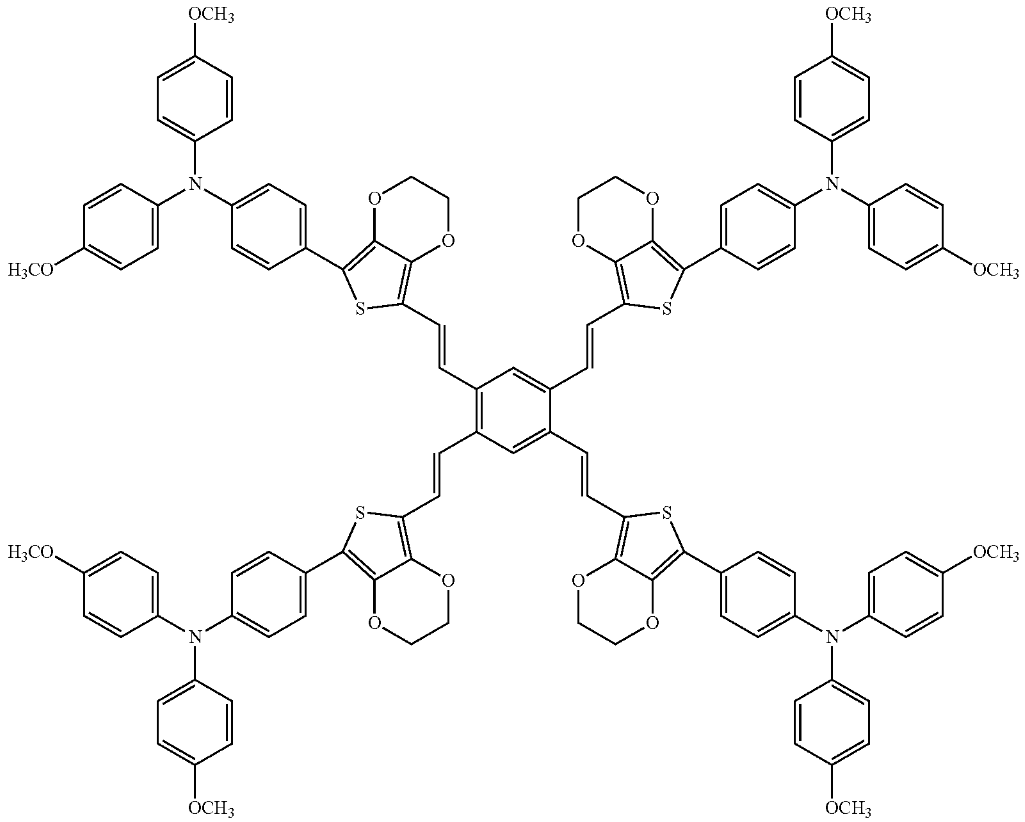

79

Synthesis Example 43

Synthesis of 4, 4', 4'', 4'''-(((1E,1'E)-1,4-Phenylene Bis(ethen-2,1-diyl)) Bis(thiophene-5,2-triyl)) Tetrakis(N, N-bis(4-methoxyphenyl) aniline) (Compound 80)

p-Bis(diethylphosphono) xylene (Compound 39; 101 mg, 0.27 mmol) and 3,5-Bis(4-(bis(4-methoxyphenyl)amino) phenyl) thiophen-2-carbaldehyde (Compound 75; 445 mg, 0.62 mmol) was dissolved in THF (10 mL) and cooled with ice water. To this solution was added 1 M tertiary butoxypotassium/THF solution (0.60 mL, 0.60 mmol) and stirred at room temperature for 2 hours. 1 M tertiary butoxypotassium/THF solution (150 μL, 0.15 mmol) was added and stirred for 2 hours, then another 150 μL (0.15 mmol) was added and stirred for 3 hours. After the reaction, the mixture was quenched with water (10 mL) and concentrated hydrochloric acid was added to adjust the pH to 2. The organic layer was extracted twice with dichloromethane (10 mL), dried over magnesium sulfate, filtered, and the filtrate was concentrated under reduced pressure. The obtained crude product was subjected to silica gel column chromatography using a mixed solvent of toluene:ethyl acetate=100:1 as a developing solvent to obtain 284 mg (0.19 mmol) of compound 80 as a red solid in a yield of 71%.

$^1$H NMR (400 MHz, $CD_2Cl_2$): δ 7.44 (d, $^3J(H,H)$=8.8 Hz, 8H), 7.37 (s, 4H), 7.33 (d, $^3J(H,H)$=16.0 Hz, 2H), 7.28 (d, $^3J(H,H)$=8.4 Hz, 8H), 7.17 (s, 2H), 7.12 (d, $^3J(H,H)$=8.8 Hz, 16H), 7.08 (d, $^3J(H,H)$=9.2 Hz, 16H), 6.96 (d, $^3J(H,H)$=8.8 Hz, 8H), 6.91 (d, $^3J(H,H)$=16.0 Hz, 2H), 6.89 (d, $^3J(H,H)$=8.8 Hz, 8H), 6.87 (d, $^3J(H,H)$=8.4 Hz, 16H), 6.86 (d, $^3J(H,H)$=9.2 Hz, 16H), 3.79 (s, 24H), 3.78 (s, 24H).

General Formula [104]

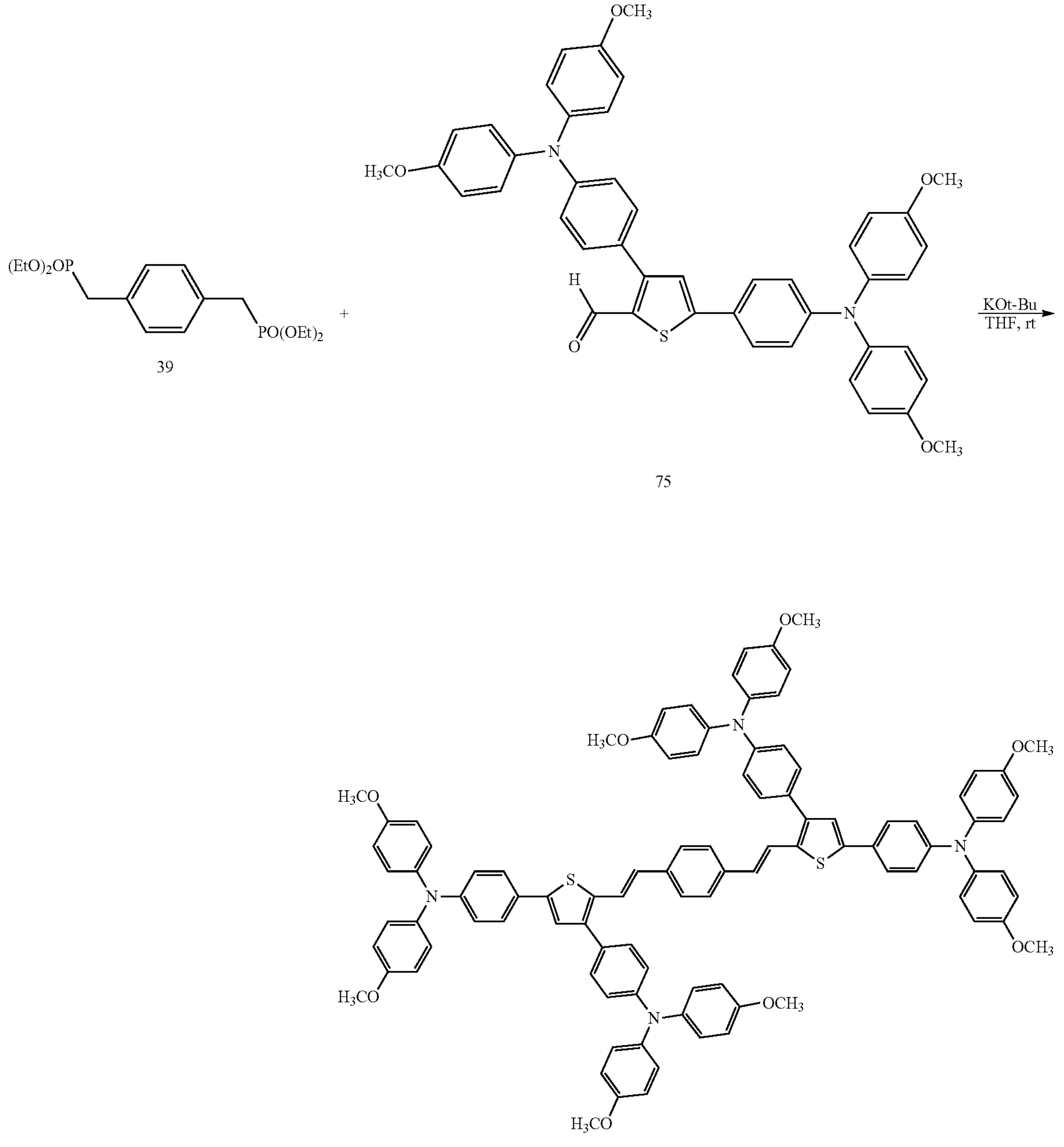

39 + 75 → 80

Synthesis Example 44

Synthesis of 4-(Bis(4-(hexyloxy)phenyl)amino) Benzaldehyde (Compound 82)

4-Bromo-4', 4"-hexyloxytriphenylamine (Compound 81; 20.0 g, 38.1 mmol) was placed in a four-necked flask. It was dissolved in THF (200 mL) and cooled to −67° C. with dry ice+acetone. A hexane solution of n-butyllithium (1.6 M, 27 mL) was added dropwise, and the mixture was stirred for 1 hour. DMF (5.9 mL, 76 mmol) was added and the temperature was raised to room temperature with stirring. Quenching with water (125 mL), ethyl acetate (40 mL) was added and the solution was separated. The organic layer was washed with saturated brine (75 mL) and dried over magnesium sulfate. After the magnesium sulfate was filtered off, the filtrate was concentrated under reduced pressure. The obtained crude product was purified by silica gel column chromatography using dichloromethane as a developing solvent to obtain 14.3 g (30.2 mmol) of Compound 82 as an orange oil in a yield of 79%.

$^1$H NMR (400 MHz, $CDCl_3$): δ 9.75 (s, 1H), 7.62 (d, $^3$J(H,H)=8.7 Hz, 2H), 7.11 (d, $^3$J(H,H)=8.7 Hz, 4H), 6.88 (d, $^3$J(H,H)=8.7 Hz, 4H), 6.84 (d, $^3$J(H,H)=8.7 Hz, 2H), 3.94 (t, $^3$J(H,H)=6.6 Hz, 4H), 1.82-1.73 (m, 4H), 1.50-1.40 (m, 4H), 1.37-1.30 (m, 8H), 0.91 (t, $^3$J(H,H)=6.9 Hz, 6H).

General Formula [105]

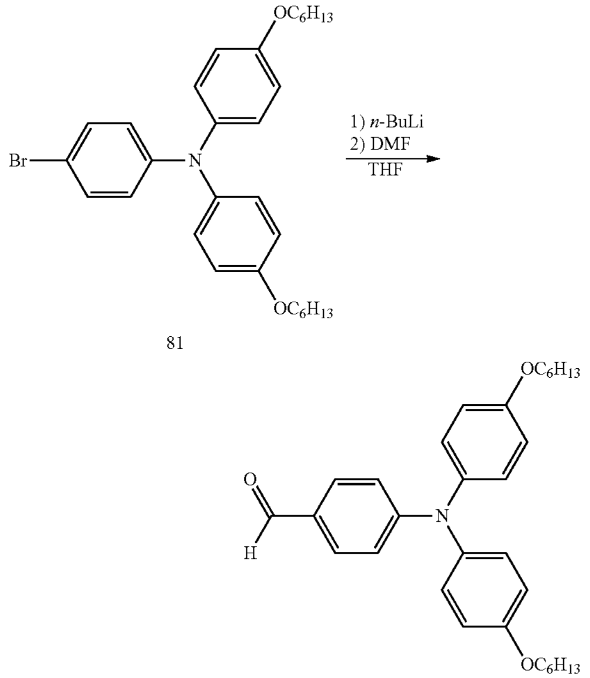

81

82

Synthesis Example 45

Synthesis of (E, E)-1,4-Bis[4-[bis(4-(hexyloxy)phenyl)amino]styryl] Benzene (Compound 83)

THF (3.4) of p-bis (diethylphosphono) xylene (Compound 39; 804 mg, 2.13 mmol) and 4-(bis (4-(hexyloxy) phenyl) amino) benzaldehyde (Compound 82; 2.09 g, 4.41 mmol) It was dissolved in mL) and cooled with ice water. A THF solution of tertiary butoxypotassium (1 M, 6.0 mmol) was added to the solution, and the mixture was stirred for 4 hours. 4-(Bis (4-(hexyloxy) phenyl) amino) benzaldehyde (Compound 82; 130 mg, 0.274 mmol) was added, and the mixture was further stirred for 2 hours. After the reaction, water (10 mL) was quenched. The mixture was extracted three times with dichloromethane (10 mL), the organic layer was washed with saturated brine (30 mL), and dried over magnesium sulfate. After the magnesium sulfate was filtered off, the filtrate was concentrated under reduced pressure. The obtained crude product was purified by silica gel column chromatography using dichloromethane:hexane=1:2 as a developing solvent, and 700 mg (0.69 mmol) of compound 83 was obtained as a yellow solid in a yield of 32%.

$^1H$ NMR (400 MHz, $CDCl_3$): δ 7.44 (s, 4H), 7.31 (d, $^3J$(H,H)=8.7 Hz, 4H), 7.07-7.00 (m, 10H), 6.96-6.88 (m, 6H), 6.82 (d, $^3J$(H,H)=8.8 Hz, 8H), 3.93 (t, $^3J$(H,H)=6.4 Hz, 8H), 1.81-1.73 (m, 8H), 1.50-1.40 (m, 8H), 1.40-1.30 (m, 16H), 0.91 (t, $^3J$(H,H)=6.9 Hz, 12H).

General Formula [106]

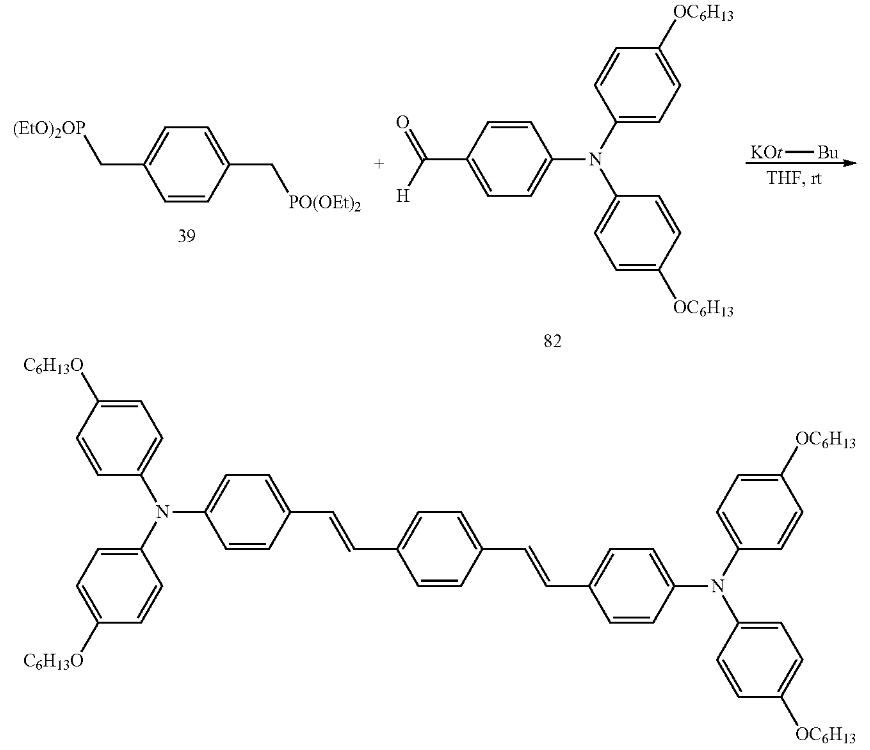

39

82

83

Synthesis Example 46

Synthesis of (E, E, E, E)-1,2,4,5-Tetrakis [4-[bis (4-(hexyloxy) phenyl) amino] styryl] Benzene (Compound 84)

1,2,4,5-Tetrakis (diethylphosphonomethyl) Benzene (Compound 44; 994 mg, 1.46 mmol) and 4-(Bis (4-(hexyloxy) phenyl) amino) Benzaldehyde (Compound 82; 2.91 g, 6.14 mmol) was dissolved in THF (13 mL) and cooled with ice water. A THF solution of tertiary butoxypotassium (1 M, 8.0 mmol) was added to the solution, and the mixture was stirred for 1 hour. After the reaction, a viscous solid was precipitated by adding to water (20 mL) quench and methanol (50 mL). This was stirred overnight to become a solid. The precipitated solid was collected by filtration and purified by NH silica gel column chromatography using dichloromethane: hexane=1:3 as the developing solvent, and then again by silica gel column chromatography using dichloromethane: hexane=4:5 as the developing solvent. Purification gave 675 mg (0.69 mmol) of Compound 84 as a yellow solid in a yield of 24%.

$^1$H NMR (400 MHz, $CDCl_3$): δ 7.72 (s, 2H), 7.35 (d, $3^J$(H,H)=8.2 Hz, 8H), 7.30 (d, $3^J$(H,H)=16.0 Hz, 4H), 7.05 (d, $3^J$(H,H)=8.8 Hz, 16H), 6.99 (d, $3^J$(H,H)=16.0 Hz, 4H), 6.91 (d, $3^J$(H,H)=8.2 Hz, 8H), 6.82 (d, $3^J$(H,H)=8.8 Hz, 16H), 3.93 (t, $3^J$(H,H)=6.4 Hz, 16H), 1.82-1.73 (m, 16H), 1.50-1.40 (m, 16H), 1.40-1.30 (m, 32H), 0.91 (t, $3^J$(H,H)=6.0 Hz, 24H).

General Formula [107]

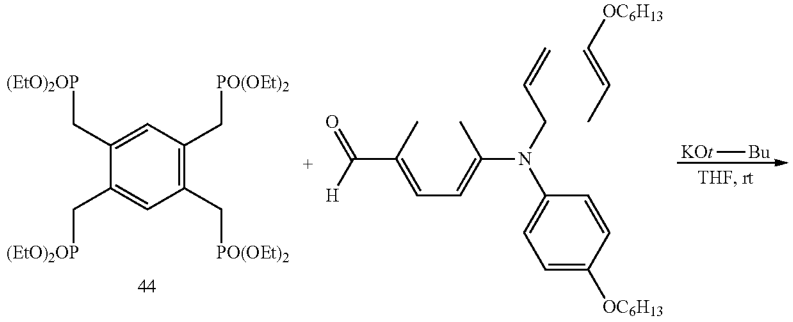

44

82

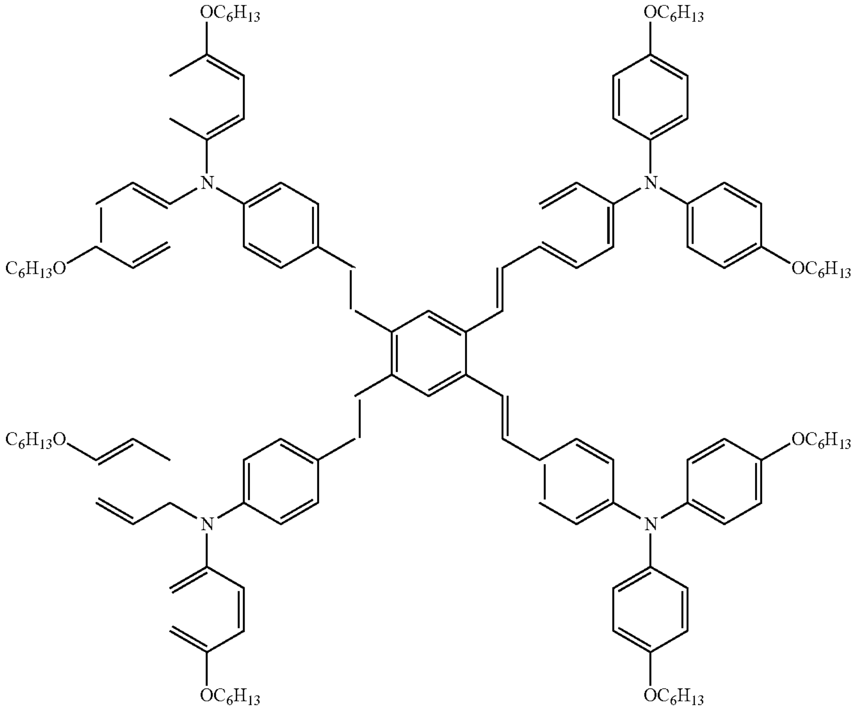

84

Synthesis Example 47

Synthesis of 4-Methoxy-N-(4-methoxyphenyl)-N-(4-vinylphenyl) aniline (Compound 85)

4-(Bis(4-methoxyphenyl)amino) Benzaldehyde (Compound 28; 3.11 g, 9.34 mmol)), methyltriphenylphosphine iodide (4.31 g, 10.7 mmol) and THF (67 mL) are placed in a two-necked flask. Cooled with ice water. A THF solution of tertiary butoxypotassium (1 M, 13.5 mL, 13.5 mmol) was added dropwise and stirred for 2.5 hours. After completion of the reaction, the insoluble material was filtered, washed with dichloromethane, and the filtrate was concentrated under reduced pressure. The crude product obtained was purified by silica gel column chromatography using a mixed solvent of dichloromethane:hexane=1:1 to obtain 2.91 g (8.78 mmol) of Compound 85 as a pale yellow oil in a yield of 94%.

$^1$H NMR (400 MHz, $CDCl_3$): δ 7.22 (d, $^3$J(H,H)=8.0 Hz, 2H), 7.04 (d, $^3$J(H,H)=9.2 Hz, 4H), 6.88 (d, $^3$J(H,H)=8.0 Hz, 2H), 6.82 (d, $^3$J(H,H)=8.8 Hz, 4H), 6.63 (dd, $^3$J(H,H)=17.6 Hz, $^3$J(H,H)=10.8 Hz, 1H), 6.58 (d, $^3$J(H,H)=17.2 Hz, 1H), 5.09 (d, $^3$J(H,H)=10.8 Hz, 1H), 3.80 (s, 6H).

General Formula [108]

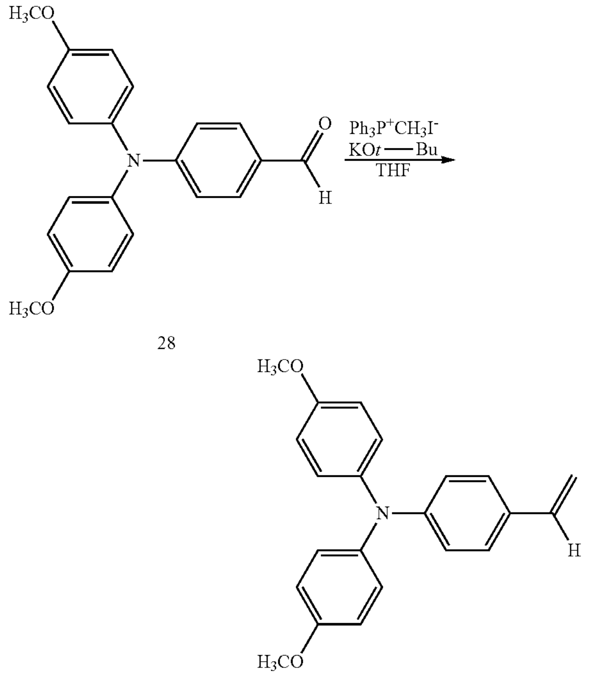

28

85

Synthesis Example 48

Synthesis of (E)-4-(4-(Bis(4-methoxyphenyl)amino) styryl) Benzaldehyde (Compound 87)

4-Methoxy-N-(4-methoxyphenyl)-N-(4-vinylphenyl) Aniline (Compound 85; 2.91 g, 8.79 mmol), 4-Bromobenzaldehyde (Compound 86; 1.61 g, 8.68 mmol), Tetrakis Triphenylphosphine palladium (270 mg, 0.234 mmol), sodium carbonate (1.80 g, 17.0 mmol), and DMF (30 mL) were placed in a two-necked flask and stirred at 130° C. for 18 hours. After air cooling, it was quenched with water (30 mL) and separated. The organic layer was extracted twice with dichloromethane (20 mL), washed once with saturated brine (30 mL), and dried over magnesium sulfate. After the magnesium sulfate was filtered off, the filtrate was concentrated under reduced pressure. The obtained crude product was purified by silica gel column chromatography using a mixed solvent of dichloromethane:hexane=2:1→4:1 to obtain 1.85 g (4.26 mmol) of compound 87 as an orange solid in a yield of 49%.

$^1$H NMR (400 MHz, $CDCl_3$): δ 9.97 (s, 1H), 7.84 (d, $^3$J(H,H)=8.0 Hz, 2H), 7.60 (d, $^3$J(H,H)=8.4 Hz, 2H), 7.34 (d, $^3$J(H,H)=8.8 Hz, 2H), 7.19 (d, $^3$J(H,H)=16.4 Hz, 1H), 7.08 (d, $^3$J(H,H)=9.2 Hz, 4H), 6.96 (d, $^3$J(H,H)=16.8 Hz, 1H), 6.90 (d, $^3$J(H,H)=8.4 Hz, 2H), 6.85 (d, $^3$J(H,H)=8.8 Hz, 4H), 3.81 (s, 6H).

General Formula [109]

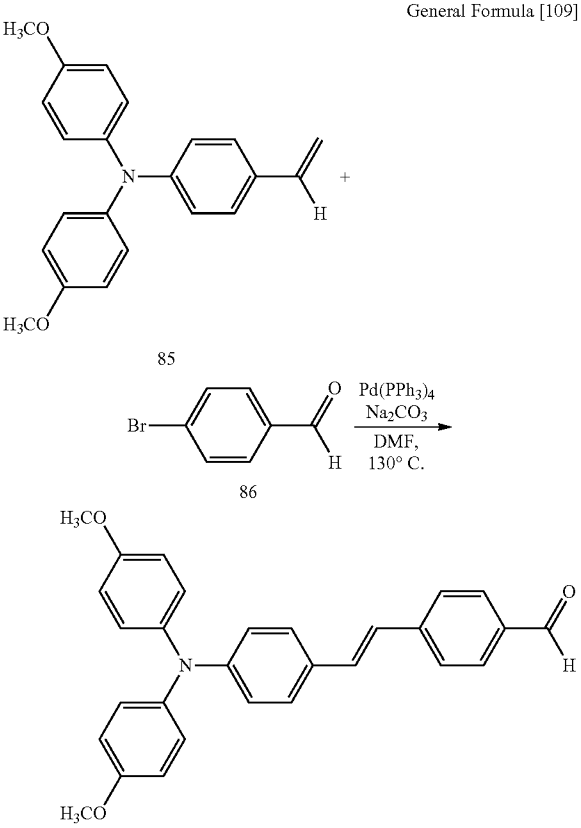

85

86

87

Synthesis Example 49

Synthesis of 4,4'-(((1E, 1'E)-(((1E, 1'E)-1,4-Phenylene Bis(ethen-2,1-diyl)) Bis(4,1-phenylene)) Bis (Eten-2,1-diyl)) Bis(N, N-bis(4-methoxyphenyl) aniline) (Compound 88)

p-Bis(diethylphosphono)xylene (Compound 39; 416 mg, 1.16 mmol) and (E)-4-(4-(bis (4-methoxyphenyl) amino) styryl) benzaldehyde (Compound 87; 1.00 g, 2.30) mmol) was dissolved in THF (15 mL) and cooled with ice water. A THF solution of tertiary butoxypotassium (1 M, 2.8 mL, 2.5 mmol) was added dropwise to the solution, and the mixture was stirred at room temperature for 1 hour. A THF solution of tertiary butoxypotassium (1 M, 0.3 mL, 0.3 mmol) was added, and the mixture was further stirred at room temperature for 30 minutes. After the reaction, water (10 mL) was quenched and methanol (10 mL) was added. The precipitated solid was collected by filtration and washed with methanol (40 mL). The crude product obtained was dissolved in dichloromethane (65 mL) and reprecipitated with diethyl ether (90 mL) to give 854 mg (0.91 mmol) of compound 88 as a yellow solid in a yield of 83%.

$^1H$ NMR (400 MHz, $CDCl_3$): δ 7.52-7.46 (m, 12H), 7.33 (d, $^3J(H,H)$=8.4 Hz, 4H), 7.12 (s, 4H), 7.09-7.04 (m, 10H), 6.94 (d, $^3J(H,H)$=17.2 Hz, 2H), 6.91 (d, $^3J(H,H)$=8.8 Hz, 4H), 6.84 (d, $^3J(H,H)$=9.2 Hz, 8H), 3.81 (s, 12H).

General Formula [110]

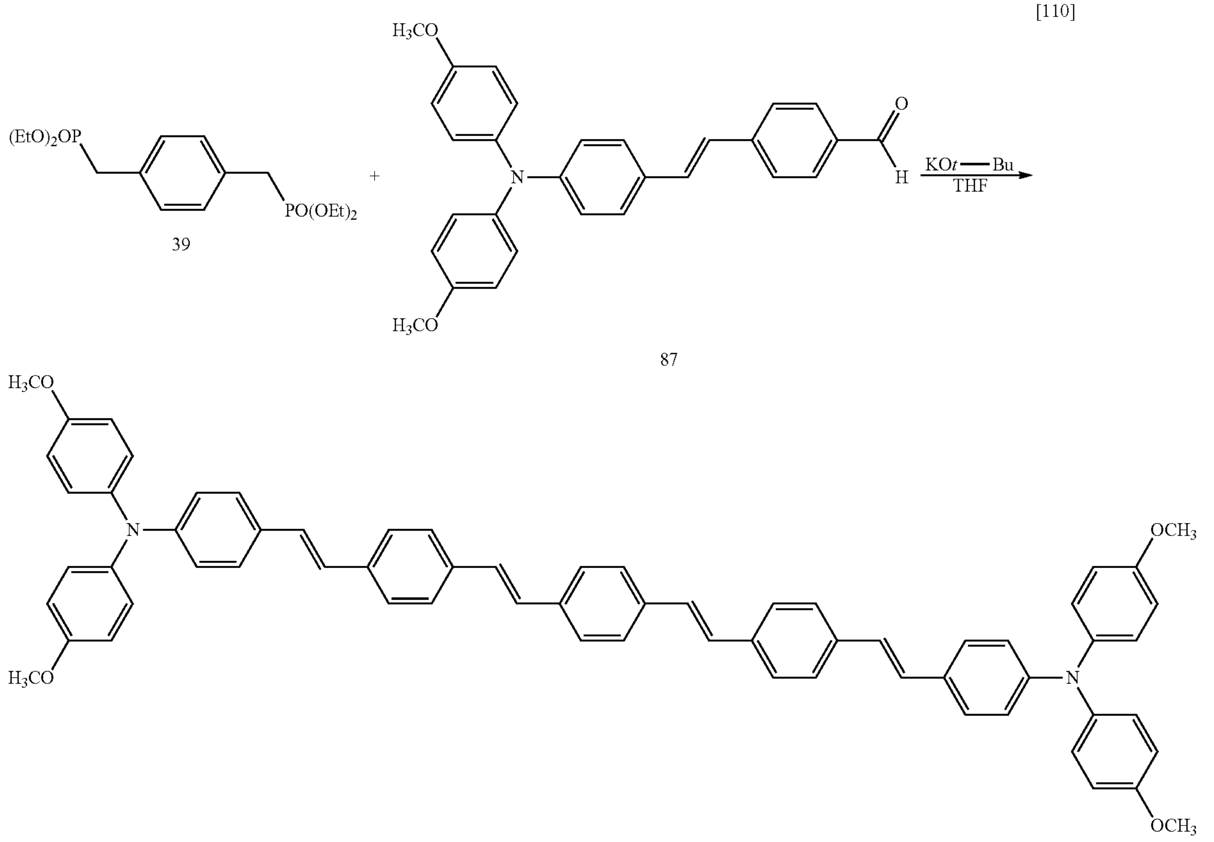

39

87

88

Synthesis Example 50

Synthesis of 2',4,4",5'-Tetramethyl-1,1':4',1"-Terphenyl (Compound 91)

1,4-Dibromo-2,5-dimethylbenzene (Compound 89; 3.93 g, 14.9 mmol), p-tolylboronic acid (Compound 90; 4.18 g, 30.7 mmol), palladium acetate (34 mg, 0.15 mmol), potassium carbonate (8.57 g, 62.0 mmol) and tetrabutylammonium bromide (9.78 g, 30.3 mmol) were placed in a flask, suspended in water (34 mL) and stirred at 70° C. for 2.5 hours. After the reaction, the insoluble material was collected by filtration and washed with water (50 mL). When the filter was dissolved in toluene (70 mL) and magnesium sulfate (4.0 g) was added, the black component was adsorbed in addition to the water contained. Magnesium sulfate was filtered and the filtrate was concentrated under reduced pressure to give 4.26 g (14.9 mmol) of compound 91 as a white solid in 100% yield.

$^1H$ NMR (400 MHz, $CDCl_3$): δ 7.28 (d, $^3J(H,H)$=8.0 Hz, 4H), 7.24 (d, $^3J(H,H)$=8.0 Hz, 4H), 7.14 (s, 2H), 2.41 (s, 6H), 2.28 (s, 6H).

General Formula [111]

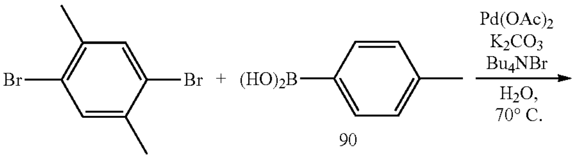

89

90

-continued

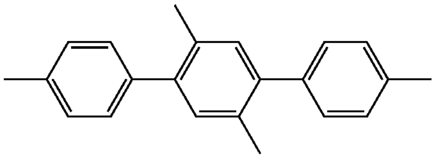

91

Synthesis Example 51

Synthesis of 2',4,4",5'-Tetrakis(bromomethyl)-1,1': 4',1"-Terphenyl (Compound 92)

2', 4,4", 5'-tetramethyl-1,1': 4', 1"-terphenyl (Compound 91; 3.60 g, 12.6 mmol) was dissolved in ethyl acetate (90 mL). The mixture was stirred at 75° C. NBS (9.47 g, 53.2 mmol) and AIBN (209 mg, 1.28 mmol) were added to the reaction mixture in 4 portions, and the mixture was stirred for 2.5 hours. After air cooling, the precipitated solid was collected by filtration and washed with ethyl acetate (30 mL) and methanol (40 mL). The filter is a mixture of the target product and a by-product with a different number of Br groups.

After concentrating the filtrate, methanol (60 mL) was added, and the insoluble material was collected by filtration and combined with the previous filtrate (3.74 g). It was used in the next step without further purification.

General Formula [112]

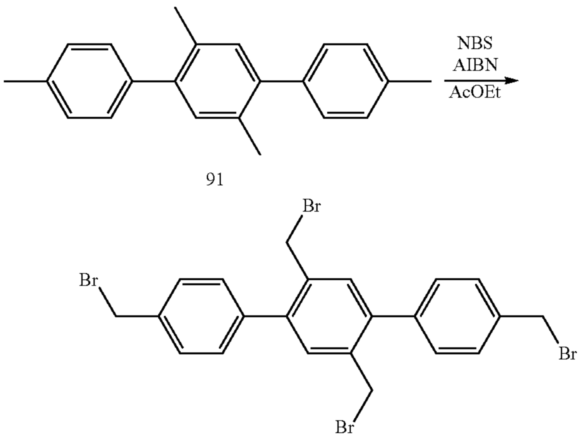

91

92

Synthesis Example 52

Synthesis of Octaethyl ([1,1': 4', 1"-terphenyl]-2', 4,4", 5'-tetrayltetrakis (methylene)) tetrakis (phosphonate) (Compound 93)

2', 4,4", 5'-tetrakis (bromomethyl)-1,1': 4', 1"-mixture of terphenyl (Compound 92; 1.00 g, 1.66 mmol) and triethyl phosphate (2.50) mL, 15.0 mmol) was mixed, toluene (10 mL) was added, and the mixture was stirred at 125° C. for 8 hours. After the reaction, water (10 mL) was added and the solution was separated. Extraction was performed twice with toluene (7 mL) and the organic layer was washed with water (10 mL) and saturated brine (10 mL). After drying over magnesium sulfate (0.3 g), the mixture was filtered and the filtrate was concentrated under reduced pressure. The obtained crude product was purified by silica gel column chromatography using a mixed solvent of dichloromethane: methanol=13:1, and the yield of 596 mg (0.717 mmol) of Compound 93 was 21% as a white solid (two steps).).

$^1$H NMR (400 MHz, $CDCl_3$) δ 7.44-7.34 (m, 10H), 4.06 (m, 8H), 3.95 (m, 8H), 3.21 (d, $^3$J(H,P)=16.8 Hz, 4H), 3.16 (d, $^3$J(H,P)=16.8 Hz, 4H), 1.28 (t, $^3$J(H,H)=7.2 Hz, 12H), 1.92 (t, $^3$J(H,H)=7.2 Hz, 12H).

General Formula [113]

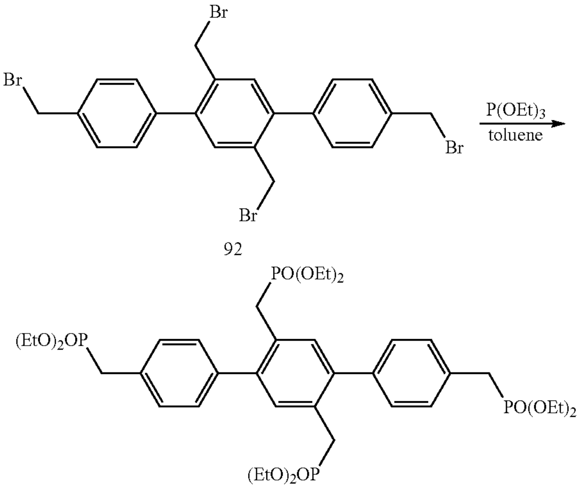

92

93

Synthesis Example 53

Synthesis of 4,4',4", 4'"-((1E, 1'E, 1"E, 1'"E)-[1,1': 4', 1"-Terphenyl]-2',4,4",5'-Tetrakis(Eten-2,1-Diyl)) Tetrakis (N, N-bis (4-methoxyphenyl) aniline) (Compound 94)

Octaethyl ([1,1': 4', 1"-terphenyl]-2', 4,4", 5'-tetrayltetrakis (methylene)) tetrakis (phosphonate) (Compound 93; 830 mg, 1.00 mmol) and 4-(bis (4-methoxyphenyl) amino) benzaldehyde (Compound 28; 1.40 g, 4.19 mmol) were dissolved in THF (10 mL) and cooled in ice water. A THF solution of tertiary butoxypotassium (1 M, 5.5 mL, 5.5 mmol) was added dropwise to this solution, and the mixture was stirred at room temperature for 3 hours. After the reaction, water (15 mL) was quenched and methanol (30 mL) was added. The precipitated solid was collected by filtration and washed with methanol (30 mL). The origin of the obtained crude product was removed with silica gel using dichloromethane as a developing solvent. Dissolved in dichloromethane (85 mL), reprecipitated with diethyl ether (85 mL), and reprecipitated again in the same manner, 1.18 g (0.76 mmol) of compound 94 was obtained as a yellow solid in a yield of 76%.

$^1$H NMR (400 MHz, $CDCl_3$): δ 7.70 (s, 2H), 7.57 (d, $^3$J(H,H)=8.0 Hz, 4H), 7.46 (d, $^3$J(H,H)=8.0 Hz, 4H), 7.36 (d, $^3$J(H,H)=8.8 Hz, 4H), 7.19 (d, $^3$J(H,H)=8.0 Hz, 4H), 7.14-6.98 (m, 24H), 6.92 (d, $^3$J(H,H)=8.0 Hz, 4H), 6.88-6.77 (m, 20H), 3.81 (s, 12H), 3.78 (s, 12H).

General Formula [114]

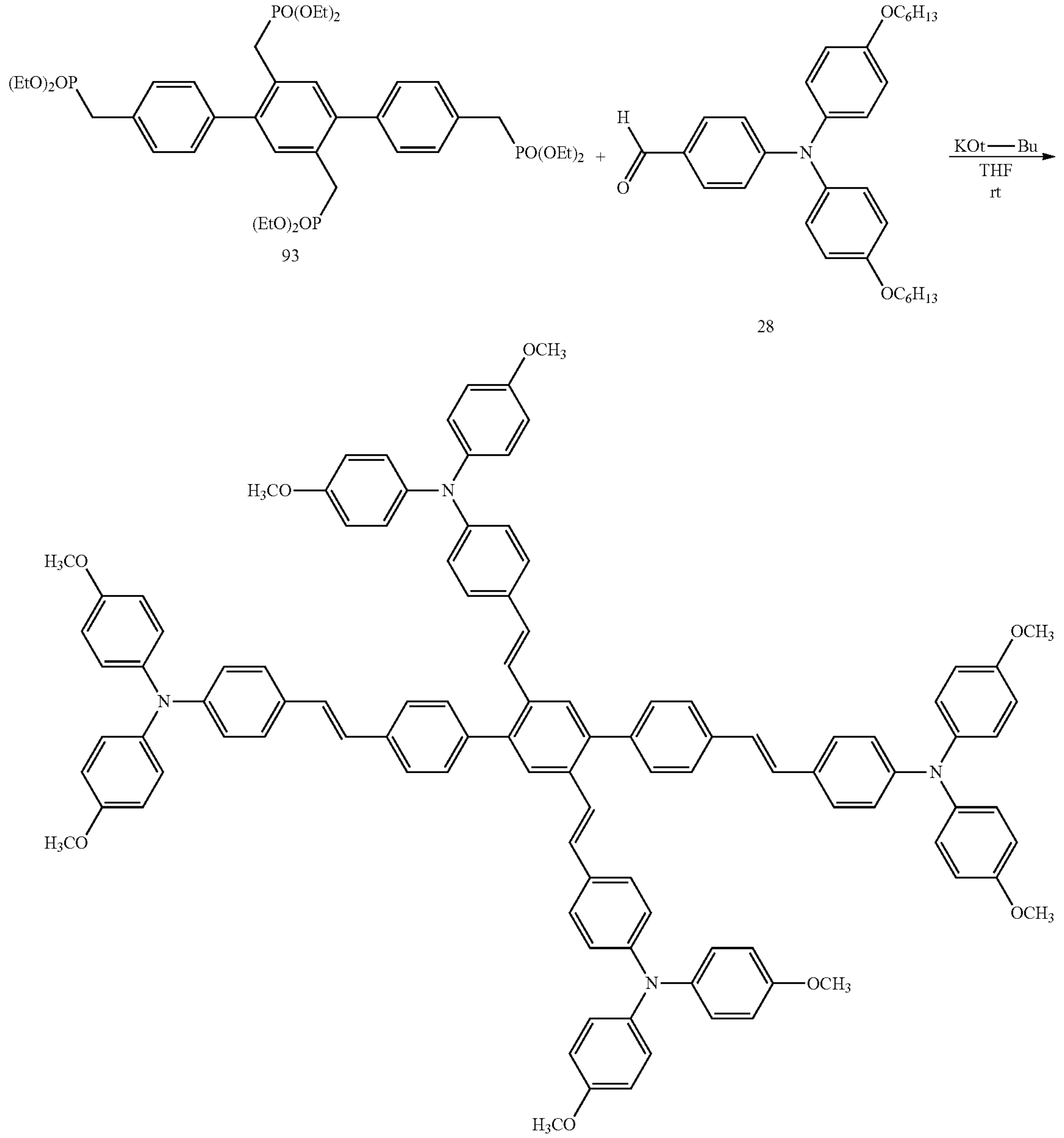

93

28

94

Synthesis Example 54

Synthesis of 4,4',4",4"-((1E, 1'E, 1"E, 1'''E)-(((1E, 1'E, 1"E, 1'''E)-[1,1':4',1"-Terphenyl]-2',4,4", 5'-Tetrakis (Eten-2,1-Diyl)) Tetrakis (Benzene)-4,1-diyl)) Tetrakis (Eten-2,1-Diyl)) Tetrakis (N, N-bis(4-methoxyphenyl) aniline) (Compound 95)

Octaethyl ([1,1': 4', 1"-terphenyl]-2', 4,4", 5'-tetrayltetrakis (methylene)) tetrakis (phosphonate) (Compound 93; 609 mg, 0.73 mmol) and (E)-4-(4-(bis (4-methoxyphenyl) amino) styryl) benzaldehyde (Compound 87; 1.31 g, 3.01 mmol) were dissolved in THF (15 mL) and cooled in ice water. A THF solution of tertiary butoxypotassium (1 M, 4.6 mL, 4.6 mmol) was added dropwise to this solution, and the mixture was stirred at room temperature for 2 hours. After the reaction, water (10 mL) was quenched and methanol (20 mL) was added. The precipitated solid was collected by filtration and washed with methanol (50 mL). The origin of the obtained crude product was removed with silica gel using dichloromethane as a developing solvent. 1.22 g (0.62 mmol) of compound by dissolving in dichloromethane (50 mL), reprecipitating with diethyl ether (75 mL Compound 95), and then reprecipitating with dichloromethane (50 mL)/diethyl ether (50 mL). was obtained as a yellow solid in a yield of 85%.

$^1$H NMR (400 MHz, $CDCl_3$): δ 7.77 (s, 2H), 7.65 (d, 3 $^J$(H,H)=8.4 Hz, 4H), 7.56-7.47 (m, 12H), 7.42 (d, 3 $^J$(H,H)=8.0 Hz, 4H), 7.38-7.29 (m, 12H), 7.22-7.17 (m, 6H), 7.13-7.03 (m, 20H), 7.02 (d, 3 $^J$(H,H)=16.4 Hz, 2H), 6.96 (d, 3 $^J$(H,H)=16.4 Hz, 2H), 6.93-6.87 (m, 10H), 6.84 (d, 3 $^J$(H, H)=8.4 Hz, 8H), 6.83 (d, 3$^J$(H,H)=8.4 Hz, 8H), 3.81 (s, 12H), 3.80 (s, 12H).

General Formula [115]

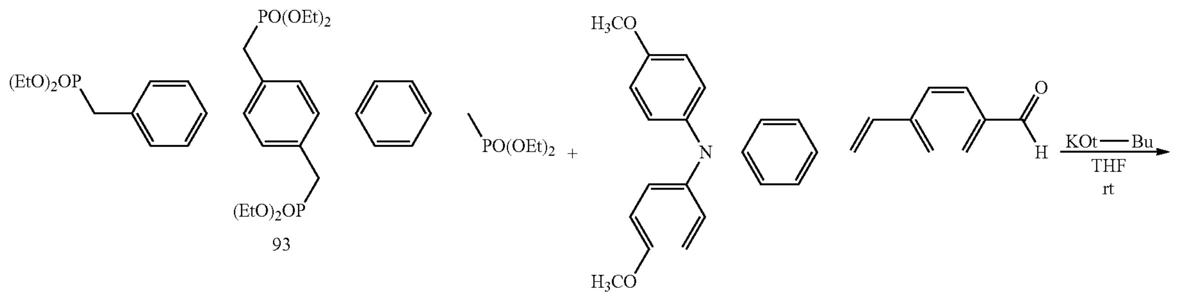

93

87

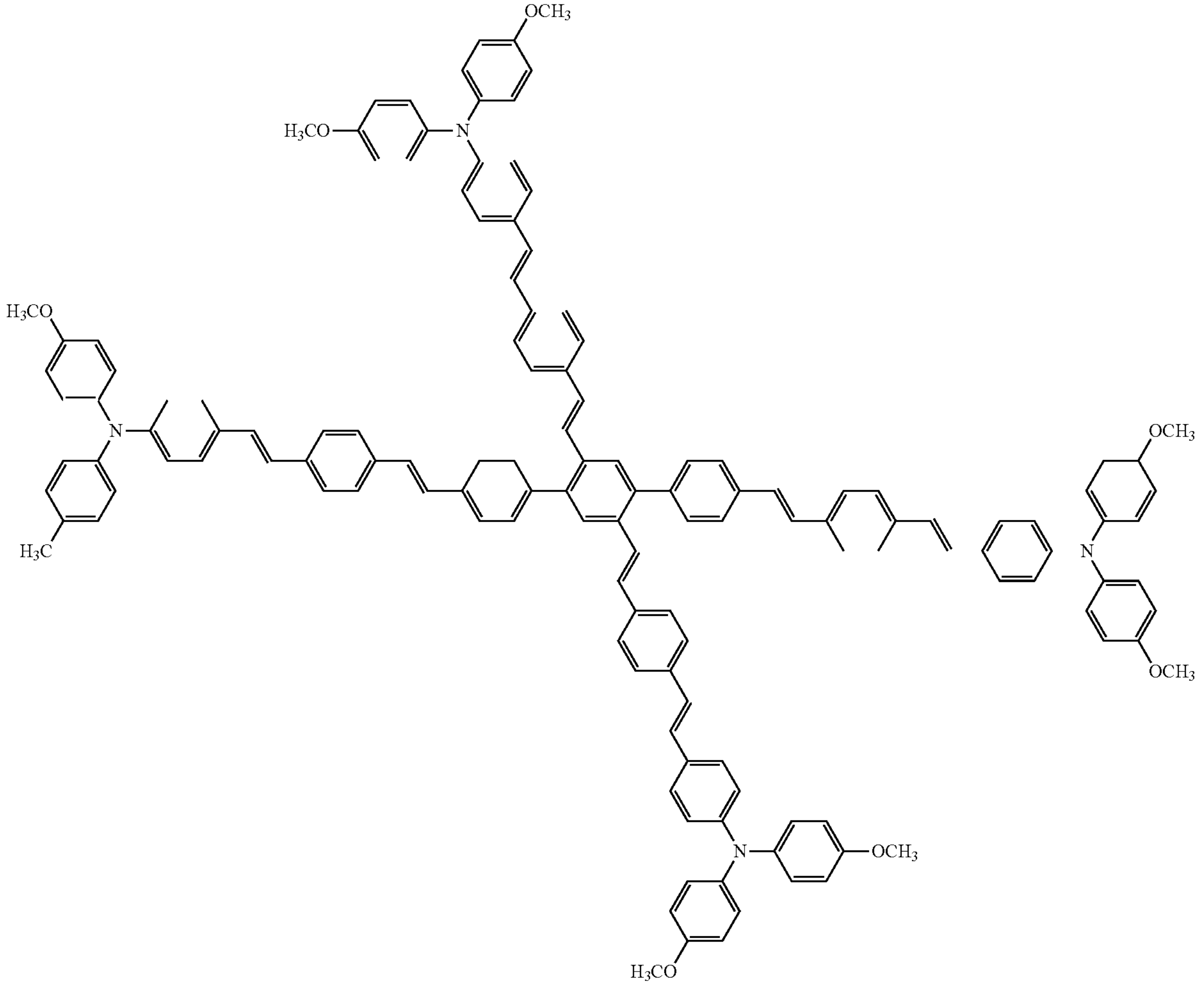

95

Measurement of Hole Mobilities]

As a pretreatment of the indium tin oxide (ITO) substrate (Glass with ITO film (sputtered product) $5\Omega/\square$ manufactured by Geomatec), ultrasonic cleaning was performed with acetone and ethanol. Next, PEDOT/PSS was spin-coated as a hole injection layer and dried at 200° C. to prepare a thin film having a diameter of 45 nm. Compound 1 was spin-coated on this and dried at 70° C. Finally, a gold electrode was vapor-deposited at 80 nm by a vacuum vapor deposition method to produce an element for SCLC measurement. Compounds 2, 7, 8, 76-80, 88, 94, 95 and Spiro-OMeTAD were used instead of Compound 1 to similarly prepare an element for SCLC measurement.

Using the prepared SCLC measuring element, the hole mobility of Compounds 1, 2, 7, 8, 76-80, 88, 94, 95 and Spiro-OMeTAD in a thin film of 150 to 240 nm was measured as a space charge limiting current (space charge limiting current). It was measured by the SCLC) method. The respective hole mobilities are shown below.

TABLE 1

| Compound | Hole Mobility ($cm^2/Vs$) |
| --- | --- |
| 1 | $1.6 \times 10^{-4}$ |
| 2 | $2.7 \times 10^{-4}$ |
| 7 | $1.3 \times 10^{-4}$ |
| 8 | $3.1 \times 10^{-4}$ |
| 76 | $2.2 \times 10^{-4}$ |
| 77 | $2.4 \times 10^{-4}$ |
| 78 | $7.6 \times 10^{-5}$ |
| 79 | $1.8 \times 10^{-4}$ |
| 80 | $1.7 \times 10^{-4}$ |
| 88 | $1.2 \times 10^{-4}$ |
| 94 | $2.1 \times 10^{-4}$ |
| 95 | $3.2 \times 10^{-5}$ |
| Spiro-OMeTAD | $2.8 \times 10^{-4}$ |

All of the measured compound groups showed the same hole mobility as Spiro-OMeTAD. In particular, compound 8 showed the highest hole mobility.

Spiro-OMeTAD is the following compound, and (product name: SHT-263, manufactured by Merck) was used.

General Formula [116]

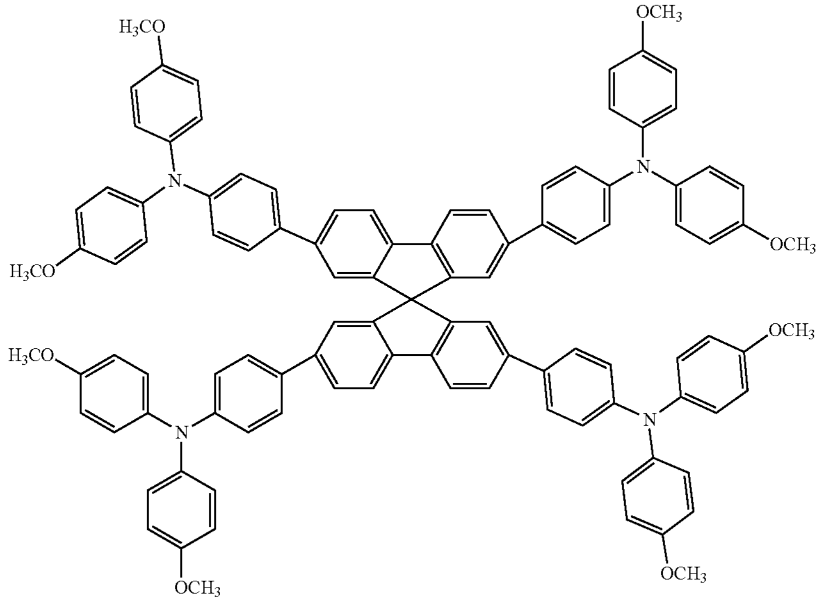

It should be noted that the above synthesis example does not require the use of expensive raw materials, and the synthesis of compounds 1, 2 and 8 does not require the use of column chromatography, which is expensive and difficult to scale up. The manufacturing cost could be suppressed. Specifically, the cost related to the production could be suppressed to about 1/10 to 1/5 of the cost related to the production of Spiro-OMeTAD.

Example 1 of the Second Aspect of the Present Invention

A perovskite solar cell element was prepared as follows by using Compound 1 in the hole transport layer forming composition.

As the substrate and the first electrode, a 1.8 mm thick conductive glass substrate (manufactured by Asahi Glass, product name FTN1.8) on which a fluorine-doped tin oxide (FTO) layer was formed was used.

As a pretreatment for the fluorine-doped tin oxide substrate, ultrasonic cleaning was performed in the order of 1% neutral detergent aqueous solution, acetone, isopropanol, and distilled water. After cleaning, the surface of the substrate was treated with ozone.

A compact titania layer was formed on the fluorine-doped tin oxide (FTO) layer. Bis (2,4-pentanedionato) Bis (2-propanol) Titanium (IV) (75% isopropyl alcohol solution) (manufactured by Tokyo Chemical Industry Co., Ltd., product name B3395) adjusted to 1/40 concentration with dehydrated ethanol did. Using this solution, a compact titania layer of 30 nm was formed on a substrate heated to 450° C. on a hot plate by a spray pyrolysis method. This substrate was air-cooled, immersed in 100 mL of distilled water containing 440 μL of titanium tetrachloride for 30 minutes, and then sintered at 500° C. to prepare a compact titania layer of 200 nm.

Subsequently, a porous titania layer was formed on the compact titania layer. The suspension is prepared by adding 8 times the amount of ethanol to the titania paste (manufactured by JGC Catalysts and Chemicals Co., Ltd., product name PST-18NR), spin-coated on the substrate, and then sintered at 500° C. As a result, a 150 nm porous titania layer was prepared.

The compact titania layer and the porous titania layer are electron transport layers.

Next, a perovskite layer was formed. PbI2/MAI (1:1)-DMF complex (manufactured by Tokyo Chemical Industry Co., Ltd., product name P2415) was adjusted by adding DMSO (dimethyl sulfoxide) to a concentration of 1.4 mol/L, and the substrate was prepared. After spin coating, the perovskite layer having a diameter of 300 nm was prepared by sequentially drying at 45° C., 55° C., 75° C., and 100° C.

Next, a hole transport layer was formed on the perovskite layer. 40 mg of Compound 1 was dissolved in 1 mL of 1,1,2,2-tetrachloroethane to prepare a hole transport layer forming composition. A hole transport layer having a diameter of 80 nm was prepared by forming a film on a substrate by spin coating using the prepared solution of the hole transport layer forming composition and then drying at 70° C.

The second electrode was formed by vapor deposition of 80 nm on the hole transport layer by a vacuum vapor deposition method.

Finally, a perovskite solar cell element was manufactured by sealing the element by pasting a glass substrate.

Examples 2 to 26 of the Second Aspect of the Present Invention, Comparative Examples 1 to 3

As shown in Table 2, instead of Compound 1, Compound 2, 3, 5, 7-9, 10, 12-14, 16-19, 21-24, 76-80, 83, 84, 88, 94 or A perovskite solar cell element was produced in the same manner as in Example 1 except that the hole transport layer forming composition was prepared using each of 95.

Comparative Example 4

A perovskite solar cell element was produced in the same manner as in Example 1 except that the following composition was used as the hole transport layer forming composition for forming the hole transport layer.

72 mg of Spiro-OMeTAD was dissolved in 1 mL of chlorobenzene, and as an additive (lactone), tris [4-tert-butyl-2-(1H-pyrazole-1-yl) pyridine] cobalt (III) tris (trifluo). Hole transport by adding lomethanesulfonyl) imide (13.5 mg), bis (trifluoromethanesulfonyl) imidelithium (9.1 mg), and 4-tert-butylpyridine (27.2 μL) and heating at 70° C. The layering composition was prepared.

Examples, Reference Examples, Comparative Examples of the First Aspect of the Present Invention As shown in Table 2, it corresponds to the examples and comparative examples of the second aspect of the present invention.

As the compound 18, the following commercially available products were used.

Compound 18: Product name B4792, manufactured by Tokyo Chemical Industry Co., Ltd.

The structure of compound 18 is as follows.

General Formula [117]

Compound 18

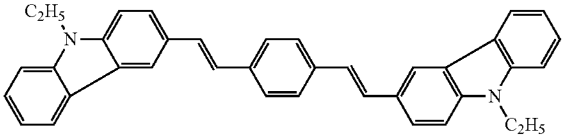

(Evaluation of Perovskite Solar Cell Devices)

The photoelectric conversion characteristics of the perovskite solar cells of the examples were measured by a method based on the method for measuring the output of crystalline solar cells of JIS C 8913. A solar simulator (OTENTO-SUNIII, spectroscope) was combined with an AM1.5G air mass filter, and the amount of light from the measurement light source was adjusted to 100 mW/cm2 using a reference solar cell. In the actual measurement, the JV curve characteristics were measured using a source meter (2400 type, Caseray Instruments) while irradiating the solar cell element masked so that the measurement area was 0.1 cm2, and the result was obtained. The short-circuit current (Jsc), open-circuit voltage (Voc), curve factor (FF), series resistance (Rs), and parallel resistance (Rsh) were derived from. Further, the photoelectric conversion efficiency (PCE) was calculated by the following formula.

$$PCE\ (\%)=(Jsc(\text{mA/cm2})\times Voc(V)\times FF/100(\text{mW/cm2}))\times 100$$

The measurement results are shown in Table 2.

The results of the elements with the maximum conversion efficiency are shown for each.

TABLE 2

| First aspect | Second aspect | Compound | Jsc (mA/cm$^2$) | Voc (V) | FF | PCE (%) | Rs (Ω cm$^2$) | Rsh (Ω cm$^2$) |
|---|---|---|---|---|---|---|---|---|
| Reference 1 | Execution 1 | 1 | 21.7 | 1.01 | 0.64 | 14.0 | 12 | 2181 |
| Execution 2 | Execution 2 | 2 | 20.7 | 1.01 | 0.71 | 14.8 | 7 | 1605 |
| Execution 3 | Execution 3 | 3 | 21.5 | 0.90 | 0.37 | 7.2 | 15 | 105 |
| Execution 4 | Execution 4 | 7 | 19.6 | 0.83 | 0.38 | 6.2 | 27 | 107 |
| Reference 5 | Execution 5 | 8 | 22.2 | 1.03 | 0.70 | 16.0 | 8 | 2393 |
| Execution 6 | Execution 6 | 9 | 20.4 | 1.01 | 0.64 | 13.1 | 10 | 906 |
| Reference 7 | Execution 7 | 13 | 21.2 | 0.90 | 0.50 | 9.5 | 25 | 537 |
| Execution 8 | Execution 8 | 14 | 21.3 | 0.98 | 0.46 | 9.7 | 14 | 239 |
| Execution 9 | Execution 9 | 16 | 19.9 | 0.97 | 0.44 | 8.5 | 34 | 232 |
| Execution 10 | Execution 10 | 17 | 19.8 | 0.97 | 0.43 | 8.3 | 18 | 211 |
| Reference 11 | Execution 11 | 18 | 10.2 | 0.90 | 0.43 | 4.0 | 13 | 137 |
| Execution 12 | Execution 12 | 19 | 11.5 | 0.85 | 0.24 | 2.3 | 95 | 61 |
| Execution 13 | Execution 13 | 21 | 16.9 | 0.80 | 0.36 | 4.9 | 21 | 59 |

TABLE 2-continued

| First aspect | Second aspect | Compound | Jsc ($mA/cm^2$) | Voc (V) | FF | PCE (%) | Rs ($\Omega$ $cm^2$) | Rsh ($\Omega$ $cm^2$) |
|---|---|---|---|---|---|---|---|---|
| Execution 14 | Execution 14 | 23 | 9.0 | 0.78 | 0.44 | 3.1 | 27 | 190 |
| Execution 15 | Execution 15 | 76 | 22.1 | 1.00 | 0.59 | 13.1 | 11 | 947 |
| Execution 16 | Execution 16 | 77 | 22.4 | 0.99 | 0.60 | 13.3 | 7 | 808 |
| Execution 17 | Execution 17 | 78 | 21.1 | 0.94 | 0.42 | 8.4 | 15 | 212 |
| Execution 18 | Execution 18 | 79 | 19.3 | 0.93 | 0.40 | 7.2 | 9 | 107 |
| Execution 19 | Execution 19 | 80 | 22.0 | 1.01 | 0.58 | 12.9 | 12 | 919 |
| Execution 20 | Execution 20 | 83 | 15.6 | 0.93 | 0.21 | 3.0 | 136 | 52 |
| Execution 21 | Execution 21 | 84 | 15.3 | 1.01 | 0.27 | 4.1 | 64 | 83 |
| Execution 22 | Execution 22 | 88 | 22.0 | 1.04 | 0.64 | 14.7 | 11 | 2073 |
| Execution 23 | Execution 23 | 94 | 22.0 | 1.03 | 0.59 | 13.4 | 11 | 764 |
| Execution 24 | Execution 24 | 95 | 20.3 | 1.10 | 0.37 | 8.3 | 30 | 106 |
| Comparative 1 | Comparative 1 | 5 | | | | <1.0 | | |
| Comparative 2 | Comparative 2 | 10 | | | | <1.0 | | |
| Comparative 3 | Comparative 3 | 12 | | | | <1.0 | | |
| Comparative 4 | Comparative 4 | Spiro-OMeTAD | 22.3 | 1.10 | 0.72 | 17.5 | 7 | 950 |

From Table 2, it can be seen that the photoelectric exchange element using the compounds 5, 10, 11 and 12 in the hole transport layer forming composition has a photoelectric conversion efficiency of less than 1.0% and does not function as a solar cell. A photoelectric conversion element using compounds 1, 2, 8, 9, 13, 14, 16, 17, 76, 77, 78, 80, 88, 94 and 95 in the hole transport layer forming composition has a photoelectric conversion efficiency. It shows a high photoelectric conversion efficiency of 8% or more. Among them, the photoelectric exchange element in which compounds 1, 2, 8 and 88 are used in the hole transport layer forming composition shows a high conversion efficiency when the photoelectric conversion efficiency is 14% or more, and in particular, compound 8 is used to form the hole transport layer. Although the photoelectric exchange element used in the composition does not contain a dopant in the hole transport layer, Spiro-OMeTAD is used in the hole transport layer forming composition, and the photoelectric exchange has a hole transport layer to which a dopant is added. It showed high photoelectric conversion efficiency comparable to that of the device.

[Evaluation of Durability]

A perovskite solar cell element using Spiro-OMeTAD containing compounds 1 and 8 and a dopant added in the same manner as in Examples under the conditions of a temperature of 20° C. and a humidity of 5% RH was stored in a light-shielded state, and immediately after the start of storage, The durability of the perovskite solar cell element was confirmed by measuring the photoelectric conversion efficiency after 4 days, 12 days, and 2 months. The results are shown in Table 3.

TABLE 3

| Compound | Storage Time (day) | Jsc ($mA/cm^2$) | Voc (V) | FF | PCE (%) | Rs ($\Omega$ $cm^2$) | Rsh ($\Omega$) |
|---|---|---|---|---|---|---|---|
| 1 | 0 | 21.7 | 0.80 | 0.40 | 7.0 | 56 | 170 |
| | 4 | 22.1 | 0.97 | 0.52 | 11.1 | 22 | 744 |
| | 12 | 21.8 | 1.04 | 0.60 | 13.6 | 12 | 699 |
| 8 | 0 | 21.7 | 0.92 | 0.48 | 9.6 | 37 | 433 |
| | 4 | 22.2 | 1.00 | 0.58 | 12.8 | 11 | 761 |
| | 12 | 22.2 | 1.03 | 0.60 | 13.7 | 12 | 759 |
| Spiro OMeTAD | 0 | 21.9 | 1.08 | 0.69 | 16.3 | 7 | 998 |
| | 4 | 22.4 | 1.06 | 0.66 | 15.7 | 7 | 750 |
| | 12 | 22.1 | 1.05 | 0.62 | 14.2 | 9 | 532 |

The photoelectric conversion efficiency of the photoelectric conversion element using Spiro-OMeTAD in the hole transport layer forming composition and having the hole transport layer to which a dopant is added decreases with the passage of time, whereas the compounds 1 and 8 The perovskite solar cell element in which the hole transport layer forming composition was used gradually improved the photoelectric conversion efficiency with the passage of time. This result is considered to be that the perovskite solar cell element in which the compounds 1 and 8 were used in the hole transport layer forming composition was improved without lowering the photoelectric conversion efficiency because the hole transport layer did not contain a dopant.

[Evaluation of Long-Term Durability]

Three perovskite solar cell elements using the compound 8 produced in the same manner as in the examples for the hole transport layer forming composition were prepared, and the perovskite solar cell elements were shielded from light under the conditions of a temperature of 20° C. and a humidity of 5% RH. The durability of the perovskite solar cell element was confirmed by measuring the photoelectric conversion efficiency immediately after the start of storage, 3 days, 2 months, and 4 months after the start of storage. The results are shown in Table 4.

TABLE 4

| Compound | Storage Time | Jsc ($mA/cm^2$) | Voc (V) | FF | PCE (%) | Rs ($\Omega$ $cm^2$) | Rsh ($\Omega$) |
|---|---|---|---|---|---|---|---|
| 8 | 3 day | 21.7 | 0.90 | 0.52 | 10.2 | 21 | 339 |
| | | 21.8 | 1.00 | 0.54 | 11.7 | 14 | 721 |
| | | 21.5 | 0.96 | 0.62 | 12.7 | 9 | 745 |
| | 2 month | 22.0 | 0.96 | 0.57 | 12.0 | 17 | 870 |
| | | 21.7 | 1.02 | 0.62 | 13.7 | 10 | 994 |
| | | 21.8 | 1.01 | 0.63 | 13.9 | 9 | 834 |
| | 4 month | 22.5 | 0.99 | 0.63 | 14.0 | 10 | 1273 |
| | | 22.3 | 0.99 | 0.63 | 13.9 | 9 | 830 |
| | | 22.1 | 1.00 | 0.64 | 14.3 | 8 | 1724 |

The photoelectric conversion efficiencies of all three photoelectric exchange elements were improved after 2 months as compared with after 3 days. Furthermore, it showed higher conversion efficiency even after 4 months. Therefore, it shows long-term durability.

[Evaluation of Durability Under Light Irradiation]

A perovskite solar cell element using Spiro-OMeTAD in which compounds 1 and 8 produced in the same manner as in the examples and a dopant were added to the hole transporting composition was produced, and the conditions were a temperature of 25° C. and a humidity of 30% RH. The durability of the perovskite solar cell element under light irradiation was confirmed by irradiating with light of 100 mW/cm2 and measuring the photoelectric conversion efficiency from immediately after production to 11 days later. The results are shown in the table below.

TABLE 5

| Compound | Time | Jsc (mA/cm$^2$) | Voc (V) | FF | PCE (%) | Rs (Ω · cm$^2$) | Rsh (Ω · cm$^2$) |
|---|---|---|---|---|---|---|---|
| 1 | 0 min | 14.3 | 0.56 | 0.19 | 1.5 | 113 | 31 |
| | 1 hour | 20.9 | 0.79 | 0.37 | 6.1 | 41 | 102 |
| | 1 day | 20.7 | 0.95 | 0.52 | 10.3 | 9 | 251 |
| | 2 day | 17.7 | 0.89 | 0.54 | 8.5 | 10 | 169 |
| | 3 day | 15.8 | 0.86 | 0.52 | 7.0 | 11 | 162 |
| | 4 day | 14.4 | 0.85 | 0.52 | 6.3 | 14 | 181 |
| | 7 day | 9.6 | 0.82 | 0.49 | 3.9 | 20 | 221 |
| | 9 day | 7.7 | 0.80 | 0.50 | 3.1 | 20 | 318 |
| | 11 day | 6.0 | 0.80 | 0.46 | 2.2 | 35 | 325 |
| 8 | 0 min | 15.6 | 0.58 | 0.21 | 1.9 | 89 | 32 |
| | 1 hour | 22.0 | 0.86 | 0.45 | 8.5 | 24 | 222 |
| | 1 day | 20.6 | 0.92 | 0.54 | 10.3 | 8 | 270 |
| | 2 day | 18.2 | 0.85 | 0.52 | 8.1 | 8 | 111 |
| | 3 day | 17.9 | 0.83 | 0.50 | 7.3 | 9 | 91 |
| | 4 day | 17.5 | 0.81 | 0.52 | 7.3 | 8 | 113 |
| | 7 day | 15.7 | 0.78 | 0.53 | 6.5 | 9 | 149 |
| | 9 day | 14.4 | 0.76 | 0.52 | 5.7 | 9 | 148 |
| | 11 day | 13.4 | 0.74 | 0.52 | 5.2 | 11 | 137 |
| Spiro-OMeTAD | 0 min | 22.2 | 1.06 | 0.67 | 15.8 | 8 | 2028 |
| | 1 hour | 20.4 | 0.96 | 0.34 | 6.7 | 12 | 80 |
| | 1 day | 6.1 | 0.87 | 0.36 | 1.9 | 22 | 94 |
| | 2 day | 3.2 | 0.85 | 0.44 | 1.2 | 42 | 494 |
| | 3 day | 3.1 | 0.81 | 0.45 | 1.1 | 39 | 564 |
| | 4 day | 3.5 | 0.76 | 0.44 | 1.2 | 41 | 434 |
| | 7 day | 3.0 | 0.72 | 0.42 | 0.9 | 49 | 445 |
| | 9 day | 2.2 | 0.73 | 0.41 | 0.6 | 63 | 566 |
| | 11 day | 0.9 | 0.74 | 0.35 | 0.2 | 169 | 1049 |

A photoelectric conversion element having a hole transport layer in which Spiro-OMeTAD is used in the hole transport layer forming composition and a dopant is added has a photoelectric conversion efficiency rapidly decreasing immediately after the start of light irradiation, whereas a compound is used. The photoelectric conversion element in which 1 and 8 were used in the hole transport layer forming composition gradually improved the photoelectric conversion efficiency from the start of light irradiation to 1 day later. Eleven days after the start of light irradiation, the photoelectric conversion efficiency of the device using Spiro-OMeTAD was reduced to 0.2%, whereas the perovskite solar cell used in the hole transport layer forming composition using compounds 1 and 8 was used. Although the battery element gradually decreased after 1 day, the photoelectric conversion efficiencies were 2.2% and 5.2%, respectively. This result shows that the perovskite solar cell device using the compounds 1 and 8 in the hole transport layer forming composition has better durability than the device using Spiro-OMeTAD even under light irradiation.

[Evaluation of Durability at Maximum Output Under Light Irradiation]

A perovskite solar cell element using the compound 8 produced in the same manner as in the examples and a perovskite solar cell element using Spiro-OMeTAD to which a dopant was added to the hole transporting composition were produced, and the temperature was 25° C. and the humidity was 30. Under the condition of % RH or less, the durability of the perovskite solar cell element under light irradiation is improved by irradiating light of 100 mW/cm2 with a voltage applied so as to maximize the output and measuring the photoelectric conversion efficiency. confirmed. The results are shown in the table below.

TABLE 6

| Compound | Time | $J_{SC}$ (mA/cm$^2$) | $V_{OC}$ (V) | FF | PCE (%) | $R_s$ (Ω · cm$^2$) | $R_{sh}$ (Ω · cm$^2$) |
|---|---|---|---|---|---|---|---|
| 8 | 0 min | 6.8 | 0.52 | 0.16 | 0.6 | 202 | 45 |
| | 15 min | 17.4 | 0.61 | 0.19 | 2.0 | 145 | 27 |
| | 30 min | 19.9 | 0.65 | 0.21 | 2.7 | 134 | 35 |
| | 1 hour | 21.3 | 0.71 | 0.24 | 3.6 | 123 | 60 |
| | 1.5 hour | 21.8 | 0.75 | 0.25 | 4.1 | 121 | 83 |
| | 5 hour | 22.5 | 0.89 | 0.31 | 6.3 | 115 | 265 |
| | 10 hour | 22.8 | 1.01 | 0.36 | 8.2 | 48 | 372 |
| | 16 hour | 22.9 | 1.03 | 0.40 | 9.4 | 28 | 517 |
| | 20 hour | 22.9 | 1.03 | 0.39 | 9.3 | 28 | 463 |
| | 25 hour | 22.8 | 1.02 | 0.38 | 8.9 | 28 | 364 |
| | 35 hour | 22.5 | 1.01 | 0.37 | 8.5 | 26 | 290 |
| | 55 hour | 22.3 | 0.97 | 0.41 | 8.8 | 17 | 273 |
| | 75 hour | 21.7 | 0.94 | 0.40 | 8.2 | 12 | 236 |
| | 100 hour | 21.3 | 0.93 | 0.40 | 7.9 | 11 | 202 |
| | 125 hour | 21.0 | 0.90 | 0.40 | 7.6 | 12 | 180 |
| | 150 hour | 20.7 | 0.87 | 0.40 | 7.2 | 13 | 161 |
| Spiro-OMeTAD | 0 min | 21.4 | 1.08 | 0.69 | 15.9 | 5 | 1476 |
| | 15 min | 21.0 | 1.03 | 0.54 | 11.8 | 4 | 253 |
| | 30 min | 20.8 | 1.02 | 0.53 | 11.2 | 4 | 203 |
| | 1 hour | 20.6 | 1.01 | 0.51 | 10.6 | 4 | 175 |
| | 1.5 hour | 20.5 | 1.01 | 0.50 | 10.3 | 4 | 164 |
| | 5 hour | 20.1 | 1.00 | 0.46 | 9.2 | 4 | 129 |

TABLE 6-continued

| Compound | Time | $J_{SC}$ (mA/cm$^2$) | $V_{OC}$ (V) | FF | PCE (%) | $R_s$ (Ω · cm$^2$) | $R_{sh}$ (Ω · cm$^2$) |
|---|---|---|---|---|---|---|---|
| | 10 hour | 18.9 | 0.99 | 0.43 | 8.0 | 3 | 84 |
| | 15 hour | 17.2 | 0.99 | 0.39 | 6.7 | 3 | 57 |
| | 20 hour | 15.1 | 0.97 | 0.33 | 4.9 | 3 | 39 |
| | 25 hour | 12.8 | 0.97 | 0.32 | 4.0 | 3 | 32 |
| | 35 hour | 8.7 | 0.91 | 0.33 | 2.6 | 3 | 29 |
| | 45 hour | 6.1 | 0.87 | 0.36 | 2.0 | 4 | 52 |
| | 55 hour | 4.8 | 0.87 | 0.39 | 1.6 | 4 | 87 |
| | 65 hour | 3.9 | 0.83 | 0.40 | 1.3 | 4 | 124 |
| | 80 hour | 3.5 | 0.85 | 0.44 | 1.3 | 4 | 209 |
| | 100 hour | 3.8 | 0.85 | 0.45 | 1.5 | 4 | 218 |

A photoelectric conversion element having a hole transport layer in which Spiro-OMeTAD is used in the hole transport layer forming composition and a dopant is added has a photoelectric conversion efficiency rapidly decreasing immediately after the start of light irradiation, whereas a compound is used. In the photoelectric exchange element using No. 8 in the hole transport layer forming composition, the photoelectric conversion efficiency gradually improved until 16 hours after the start of light irradiation, and then the photoelectric conversion efficiency began to decrease. 100 hours after the start of light irradiation, the photoelectric conversion efficiency of the device using Spiro-OMeTAD was reduced to 1.5%, whereas the perovskite solar cell using compound 8 in the hole transport layer forming composition was used. Although the element gradually decreased, the photoelectric conversion efficiency was 7.2% even 150 hours after the start of light irradiation. As a result, the perovskite solar cell device using the compound 8 in the hole transport layer forming composition has better durability than the device using the Spiro-OMeTAD even under light irradiation to which the maximum output voltage is applied. It shows that.

[Evaluation of Durability Against Heating]

A perovskite solar cell element using the compound 8 produced in the same manner as in the examples and a perovskite solar cell element using Spiro-OMeTAD to which a dopant was added to the hole transporting composition were prepared, and a perovskite solar cell element was prepared at 150° C. under a nitrogen atmosphere. The durability of the perovskite solar cell element against heating was confirmed by heating with. The results are shown below.

TABLE 7

| Compound | Entry | Time | $J_{SC}$ (mA/cm$^2$) | $V_{OC}$ (V) | FF | PCE (%) | Rs (Ω · cm$^2$) | Rsh (Ω · cm$^2$) |
|---|---|---|---|---|---|---|---|---|
| 8 | 1 | 0 min | 22.8 | 1.01 | 0.65 | 14.9 | 6 | 604 |
| | | 30 min | 22.6 | 0.98 | 0.64 | 14.2 | 4 | 2331 |
| | 2 | 0 min | 22.0 | 1.02 | 0.70 | 15.7 | 6 | 1771 |
| | | 30 min | 21.6 | 0.92 | 0.52 | 10.2 | 6 | 284 |
| | 3 | 0 min | 22.1 | 1.02 | 0.58 | 13.0 | 14 | 1053 |
| | | 30 min | 21.7 | 0.96 | 0.56 | 11.7 | 6 | 427 |
| | | 1 h | 21.8 | 0.95 | 0.40 | 8.3 | 7 | 94 |
| | 4 | 0 min | 21.8 | 0.96 | 0.61 | 12.8 | 9 | 391 |
| | | 30 min | 21.5 | 0.95 | 0.59 | 12.2 | 5 | 665 |
| | | 1 h | 21.3 | 0.96 | 0.47 | 9.7 | 5 | 96 |
| | 5 | 0 min | 21.9 | 1.02 | 0.68 | 15.2 | 7 | 564 |
| | | 30 min | 21.7 | 0.96 | 0.59 | 12.2 | 5 | 534 |
| | | 1 h | 21.8 | 0.96 | 0.53 | 11.1 | 5 | 143 |
| | 6 | 0 min | 22.1 | 1.03 | 0.64 | 14.5 | 10 | 1588 |
| | | 30 min | 21.5 | 1.00 | 0.60 | 12.9 | 8 | 931 |
| | | 1 h | 21.5 | 0.99 | 0.41 | 8.7 | 7 | 72 |
| | 7 | 0 min | 22.1 | 0.99 | 0.60 | 13.1 | 10 | 1551 |
| | | 30 min | 21.4 | 0.99 | 0.59 | 12.6 | 7 | 848 |
| | | 1 h | 21.7 | 0.98 | 0.46 | 9.8 | 6 | 112 |
| | 8 | 0 min | 21.6 | 0.98 | 0.61 | 12.9 | 11 | 1209 |
| | | 30 min | 21.5 | 0.99 | 0.55 | 11.6 | 9 | 556 |
| | | 1 h | 21.7 | 0.98 | 0.53 | 11.3 | 6 | 336 |
| | 9 | 0 min | 21.7 | 0.96 | 0.56 | 11.7 | 21 | 1142 |
| | | 30 min | 21.3 | 0.98 | 0.59 | 12.5 | 6 | 749 |
| | | 1 h | 21.2 | 0.96 | 0.42 | 8.6 | 6 | 96 |
| | 10 | 0 min | 21.3 | 0.98 | 0.61 | 12.7 | 11 | 696 |
| | | 30 min | 20.9 | 0.97 | 0.58 | 11.8 | 6 | 556 |
| | | 1 h | 21.0 | 0.95 | 0.49 | 9.8 | 5 | 146 |
| Spiro-OMeTAD | 1 | 0 min | 21.9 | 1.07 | 0.70 | 16.4 | 7 | 2419 |
| | | 30 min | 10.6 | 0.86 | 0.26 | 2.4 | 32 | 84 |
| | 2 | 0 min | 22.0 | 1.06 | 0.64 | 15.0 | 7 | 471 |
| | | 30 min | 18.9 | 0.54 | 0.22 | 2.3 | 12 | 28 |
| | 3 | 0 min | 21.6 | 1.06 | 0.68 | 15.5 | 6 | 887 |
| | | 30 min | 18.8 | 0.57 | 0.26 | 2.8 | 9 | 33 |

A photoelectric exchange element having a hole transport layer in which Spiro-OMeTAD is used in the hole transport layer forming composition and a dopant is added has a significantly reduced photoelectric conversion efficiency of 2 to 3% after heating for 30 minutes. It was. On the other hand, in the photoelectric exchange element using the compound 8 in the hole transport layer forming composition, although the conversion efficiency is lowered in most of the elements, the change is small, and even after heating for 1 hour. All elements maintained a conversion efficiency of 8% or more. This result shows that the perovskite solar cell device using the compound 8 in the hole transport layer forming composition has superior durability to heating as compared with the device using the Spiro-OMeTAD.

[Mixed Perovskite Solar Cells]

As the composition of the perovskite layer, a mixed perovskite solar cell element in which three types of cations of MA, FA and Cs and two types of anions of I and Br were combined in the same manner was produced and its characteristics were evaluated.

Manufacturing of Mixed Perovskite Solar Cell Element (Mixed Solar Cell Element 1) 1]

Using compound 8 in the hole transport layer forming composition, a mixed perovskite solar cell element was prepared as follows.

As the substrate and the first electrode, a 1.8 mm thick conductive glass substrate (manufactured by Asahi Glass, product name FTN1.8) on which a fluorine-doped tin oxide (FTO) layer was formed was used.

As a pretreatment for the fluorine-doped tin oxide substrate, ultrasonic cleaning was performed in the order of 1% neutral detergent aqueous solution, acetone, isopropanol, and distilled water. After cleaning, the surface of the substrate was treated with ozone.

A compact titania layer was formed on the fluorine-doped tin oxide (FTO) layer. Bis (2,4-pentanedionato) Bis (2-propanol) Titanium (IV) (75% isopropyl alcohol solution) (manufactured by Tokyo Chemical Industry Co., Ltd., product name B3395) adjusted to 1/40 concentration with dehydrated ethanol did. Using this solution, a compact titania layer of 30 nm was formed on a substrate heated to 450° C. on a hot plate by a spray pyrolysis method. This substrate was air-cooled, immersed in 100 mL of distilled water containing 440 μL of titanium tetrachloride for 30 minutes, and then sintered at 500° C. to prepare a compact titania layer of 200 nm.

Subsequently, a porous titania layer was formed on the compact titania layer. The suspension is prepared by adding 8 times the amount of ethanol to the titania paste (manufactured by JGC Catalysts and Chemicals Co., Ltd., product name PST-18NR), spin-coated on the substrate, and then sintered at 500° C. As a result, a 150 nm porous titania layer was prepared.

The compact titania layer and the porous titania layer are electron transport layers.

Next, a perovskite layer was formed. PbBr2, MABr, CsI, and FAPbI3 were added in a ratio of 8:1 so that the composition was Cs0.045MA0.15FA0.825Pb12.55Br0.45 and the concentration of Pb was 1.65 mol/L. A 300 nm perovskite layer was prepared by adjusting, spin-coating the substrate, and then drying at 100° C.

Next, a hole transport layer was formed on the perovskite layer. 40 mg of Compound 8 was dissolved in 1 mL of 1,1,2,2-tetrachloroethane to prepare a hole transport layer forming composition. A hole transport layer having a diameter of 80 nm was prepared by forming a film on a substrate by spin coating using the prepared solution of the hole transport layer forming composition and then drying at 70° C.

The second electrode was formed by vapor deposition of 80 nm on the hole transport layer by a vacuum vapor deposition method.

Finally, a perovskite solar cell element (mixed solar cell element 1) was manufactured by sealing the element by pasting a glass substrate.

Manufacturing of Mixed Perovskite Solar Cell Element (Mixed Solar Cell Element 2) 2]

Using compound 8 in the hole transport layer forming composition, a mixed perovskite solar cell element having a different element structure of the photoelectric conversion element was produced as follows.

As the substrate and the first electrode, a conductive glass substrate with a thickness of 1.1 mm (Glass with ITO film (sputtered product) 10Ω/□) on which an indium tin oxide (ITO) layer was formed was used.

As a pretreatment for the indium tin oxide substrate, ultrasonic cleaning was performed in the order of ethanol, acetone, semicoclean, water and ethanol. After cleaning, the surface of the substrate was treated with ozone.

A tin oxide layer (SnO2) was formed on the ITO layer. A 15% colloidal aqueous dispersion of tin oxide was adjusted to a concentration of ½ with distilled water. This dispersion was spin-coated on the substrate and then dried at 150° C. for 30 minutes to prepare a tin oxide layer having a diameter of 40 nm. This tin oxide layer becomes an electron transport layer.

Next, a perovskite layer was formed. PbI2, PbBr2, MABr, CsI, and FAPbI3 were adjusted by adding DMSO and DMF at a concentration of 1.05 mol/L at a ratio of 1:4, spin-coated on the substrate, and then dried at 100° C. A 250 nm perovskite layer (Cs0.05MA0.15FA0.80Pb12.75Br0.25) was prepared by this.

Next, a hole transport layer was formed on the perovskite layer. 45 mg of Compound 8 was dissolved in 1 mL of 1,1,2,2-tetrachloroethane to prepare a hole transport layer forming composition. A hole transport layer having a diameter of 80 nm was prepared by forming a film on a substrate by spin coating using the prepared solution of the hole transport layer forming composition and then drying at 70° C.

The second electrode was formed by vapor deposition of 80 nm on the hole transport layer by a vacuum vapor deposition method.

Finally, a perovskite solar cell element (mixed solar cell element 2) was manufactured by sealing the element by pasting a glass substrate.

Manufacture of Mixed Perovskite Solar Cell Elements Using Additives in the Hole Transport Layer]

When an additive (dopant) is used for the hole transport layer, 45 mg of compound 8 is dissolved in 1 mL of chlorobenzene, bis (trifluoromethanesulfonyl) imidelithium (4.5 mg), and 4-tert-butylpyridine (4.5 mg). 13.5 μL) was added and heated at 70° C. to prepare a perovskite solar cell element in the same manner as the mixed solar cell elements 1 and 2 except that the hole transport layer forming composition was prepared.

Manufacture of Mixed Perovskite Solar Cell Element Using Spiro-OMeTAD for Hole Transport Layer]

When Spiro-OMeTAD was used as the hole transport layer forming composition for forming the hole transport layer, 72 mg of Spiro-OMeTAD was dissolved in 1 mL of chlorobenzene, and Tris [4-tert-Butyl-2-(1H-pyrazol-1-yl) pyridine] Cobalt (III) Tris (trifluoromethanesulfonyl) imide (13.5 mg), bis (trifluoromethanesulfonyl) imide lithium (9.1 mg), and 4-Perovskite solar cells in the same manner as the mixed solar cell elements 1 and 2, except that the hole transport layer forming composition was prepared by adding tert-butylpyridine (27.2 μL) and heating at 70° C. The element was manufactured.

Table 8 shows the results of the elements with the maximum conversion efficiency among the photoelectric conversion elements of the mixed system.

TABLE 8

| Compound | ETL and substrate | Dopant | $J_{SC}$ (mA/cm$^2$) | $V_{OC}$ (V) | FF | PCE (%) | $R_s$ ($\Omega \cdot cm^2$) | $R_{sh}$ ($\Omega \cdot cm^2$) |
|---|---|---|---|---|---|---|---|---|
| 8 | FTO/$TiO_2$ | without | 21.2 | 1.11 | 0.71 | 16.6 | 9 | 2945 |
| | | with | 21.5 | 1.03 | 0.65 | 14.5 | 10 | 2002 |
| | ITO/$SnO_2$ | without | 21.3 | 1.05 | 0.69 | 15.4 | 8 | 644 |
| | | with | 22.2 | 1.07 | 0.76 | 18.1 | 5 | 10380 |
| Spiro- | FTO/$TiO_2$ | with | 22.3 | 1.11 | 0.72 | 17.8 | 7 | 3532 |
| OMeTAD | ITO/$SnO_2$ | with | 22.9 | 1.11 | 0.72 | 18.3 | 6 | 2536 |

The photoelectric exchange element using Spiro-OMeTAD in the hole transport layer forming composition showed a conversion efficiency of about 18% regardless of whether FTO/TiO2 or ITO/SnO2 was used as a substrate. On the other hand, the photoelectric exchange elements using Compound 8 in the hole transport layer forming composition without additives are as high as 16.6% and 15.4%, respectively, although they are inferior to the devices using Spiro-OMeTAD. The conversion efficiency was shown. Furthermore, in the device using ITO/SnO2 as a base, the photoelectric exchange element used in the hole transport layer forming composition in which the additive is added to compound 8 is 18.1%, which is extremely high photoelectric comparable to Spiro-OMeTAD. The conversion efficiency was shown.

[Evaluation of Durability of Mixed Elements Against Heating]

A mixed perovskite solar cell element using Spiro-OMeTAD, which is obtained by adding compound 8 and a dopant produced in the same manner as the mixed solar cell element to a hole transporting composition, was prepared and heated at 150° C. under a nitrogen atmosphere. By doing so, the durability of the mixed perovskite solar cell element against heating was confirmed. The results are shown below.

TABLE 9

| Compound | Substrate | Entry | 150° C. | $J_{SC}$ (mA/cm$^2$) | $V_{OC}$ (V) | FF | PCE (%) | $R_s$ ($\Omega \cdot cm^2$) | $R_{sh}$ ($\Omega \cdot cm^2$) |
|---|---|---|---|---|---|---|---|---|---|
| 8 | FTO | 1 | 0 min | 18.6 | 1.09 | 0.77 | 15.5 | 8 | 35762 |
| | | | 30 min | 20.0 | 1.04 | 0.46 | 9.6 | 12 | 269 |
| | | | 1 h | 19.1 | 0.95 | 0.55 | 10.0 | 10 | 526 |
| | | 2 | 0 min | 20.2 | 1.08 | 0.73 | 15.9 | 8 | 3587 |
| | | | 30 min | 20.0 | 0.97 | 0.41 | 8.0 | 14 | 170 |
| | | | 1 h | 17.6 | 0.87 | 0.49 | 7.5 | 20 | 474 |
| | | 3 | 0 min | 19.9 | 1.04 | 0.64 | 13.1 | 13 | 2969 |
| | | | 30 min | 20.4 | 1.05 | 0.38 | 8.2 | 13 | 224 |
| | | | 1 h | 18.2 | 0.92 | 0.54 | 9.1 | 14 | 1327 |
| | ITO | 1 | 0 min | 21.0 | 0.97 | 0.68 | 13.8 | 8 | 1413 |
| | | | 30 min | 19.8 | 0.84 | 0.45 | 7.4 | 13 | 107 |
| | | | 1 h | 19.9 | 0.75 | 0.47 | 7.0 | 12 | 90 |
| | | 2 | 0 min | 21.4 | 0.99 | 0.68 | 14.5 | 7 | 1382 |
| | | | 30 min | 19.4 | 0.84 | 0.47 | 7.6 | 15 | 118 |
| | | | 1 h | 19.8 | 0.78 | 0.48 | 7.4 | 14 | 109 |
| | | 3 | 0 min | 21.1 | 0.99 | 0.69 | 14.4 | 8 | 1096 |
| | | | 30 min | 20.4 | 0.84 | 0.50 | 8.6 | 14 | 144 |
| | | | 1 h | 20.6 | 0.80 | 0.52 | 8.5 | 10 | 135 |
| | | 4 | 0 min | 21.0 | 1.05 | 0.68 | 15.0 | 8 | 523 |
| | | | 30 min | 19.2 | 0.96 | 0.55 | 10.3 | 20 | 335 |
| | | | 1 h | 19.5 | 0.96 | 0.52 | 9.7 | 23 | 190 |
| | | 5 | 0 min | 21.3 | 1.05 | 0.69 | 15.4 | 8 | 644 |
| | | | 30 min | 18.9 | 0.97 | 0.61 | 11.2 | 8 | 329 |
| | | | 1 h | 17.7 | 0.96 | 0.50 | 8.5 | 38 | 185 |
| Spiro- | FTO | 1 | 0 min | 22.3 | 1.11 | 0.72 | 17.8 | 7 | 3532 |
| OMeTAD | | | 30 min | 10.9 | 0.97 | 0.27 | 2.9 | 50 | 95 |
| | | 2 | 0 min | 22.0 | 1.09 | 0.72 | 17.2 | 7 | 3029 |
| | | | 30 min | 10.9 | 0.96 | 0.26 | 2.8 | 50 | 90 |
| | | 3 | 0 min | 22.1 | 1.10 | 0.72 | 17.5 | 7 | 5544 |
| | | | 30 min | 14.2 | 1.05 | 0.31 | 4.6 | 37 | 104 |
| | ITO | 1 | 0 min | 22.9 | 1.11 | 0.72 | 18.3 | 6 | 2536 |
| | | | 30 min | 8.8 | 0.71 | 0.28 | 1.7 | 21 | 81 |
| | | 2 | 0 min | 22.8 | 1.09 | 0.71 | 17.6 | 6 | 3570 |
| | | | 30 min | 9.9 | 0.66 | 0.29 | 1.9 | 20 | 71 |

By heating the photoelectric exchange element using Spiro-OMeTAD in the hole transport layer forming composition at 150° C. for 30 minutes, the conversion efficiency is remarkably lowered like the element of MAPbI3, and the conversion efficiency after heating is FTO/. It was 2.8 to 4.6% for TiO2 and 1.7 to 1.9% for ITO/SnO2. On the other hand, the photoelectric exchange element in which the compound 8 was used in the hole transport layer forming composition was lower than that in the case of MAPbI3, but the conversion efficiency after heating for 1 hour was 7 to 10% in each case. there were. The result shows that even in the case of a mixed perovskite solar cell element, by using compound 8 in the hole transport layer forming composition, it has better durability against heating than the element using Spiro-OMeTAD. It shows.

[Evaluation of Photoelectric Conversion Element Using Molybdenum Oxide]

In the perovskite solar cell element using compound 8, an element having a molybdenum oxide layer between the hole transport layer and the second electrode was prepared, and the characteristics were evaluated. The molybdenum oxide layer was formed by depositing 10 nm on the hole transport layer by a vacuum vapor deposition method.

The measurement results are shown in Table 10.

TABLE 10

| Perovskite layer | $J_{SC}$ (mA/cm$^2$) | $V_{OC}$ (V) | FF | PCE (%) | $R_s$ ($\Omega \cdot cm^2$) | $R_{sh}$ ($\Omega \cdot cm^2$) |
|---|---|---|---|---|---|---|
| $MAPbI_3$ | 22.2 | 1.01 | 0.66 | 14.7 | 6 | 1306 |
| Mix (FTO/$TiO_2$) | 22.0 | 0.99 | 0.72 | 15.7 | 6 | 5053 |
| Mix (ITO/$SnO_2$) | 22.4 | 1.03 | 0.68 | 15.6 | 6 | 1368 |

From Table 10, the photoelectric exchange elements used in the compound 8-hole transport layer forming composition and having the molybdenum oxide layer formed on them have a high photoelectric conversion efficiency of 14% or more regardless of the composition of the perovskite layer used.

EXPLANATION OF SYMBOLS

1: Normal structure element
2: Inverted structure element
3: Substrate
4: First electrode
5: Electron transport layer
6: Perovskite layer
7: Hole transport layer
8: Second electrode

The invention claimed is:

1. A hole transport layer forming composition for perovskite solar cells, comprising: a solvent; no dopant; and a compound represented by:

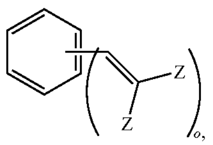

wherein, in the compound, o is an integer from 1 to 6 and wherein Z is independently hydrogen or represented by:

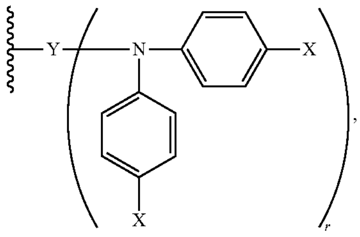

wherein X is an alkoxy group or an alkylthio group, wherein r is 1 or 2, and wherein Y is at least one species selected from the following groups:

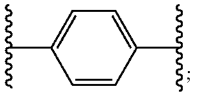

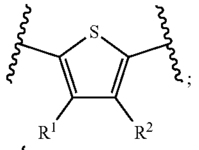

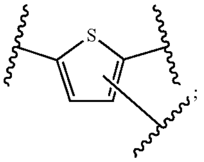

or

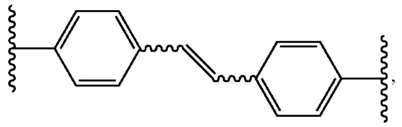

wherein $R^1$ and $R^2$ are independently hydrogen, alkyl groups, or alkoxy groups, or $R^1$ and $R^2$ are combined to form a ring having one or two oxygen atoms, and wherein Z is not all hydrogen.
2. The hole transport layer forming composition for perovskite solar cells according to claim 1, wherein the compound is selected from:
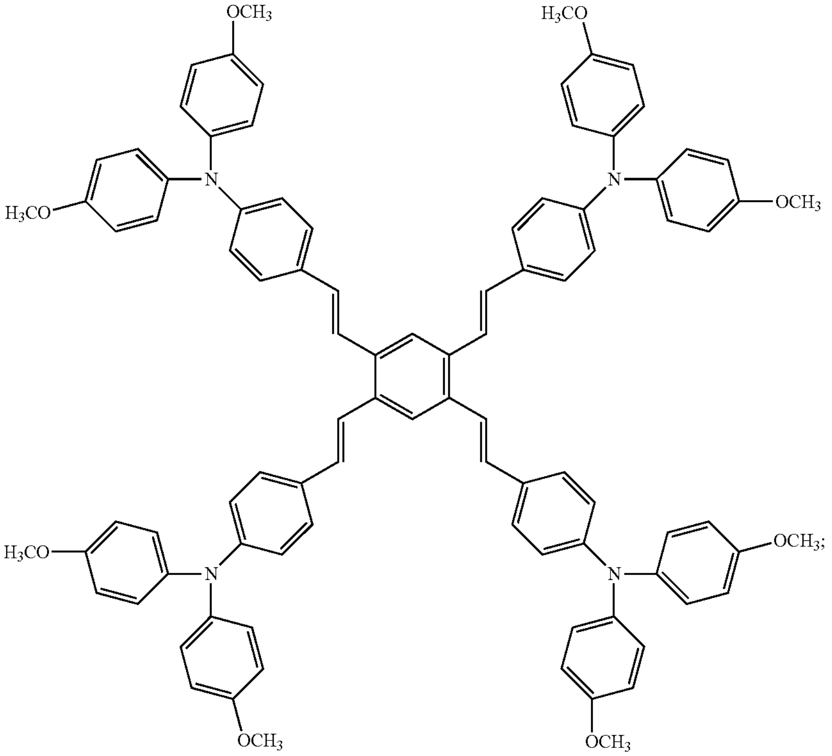
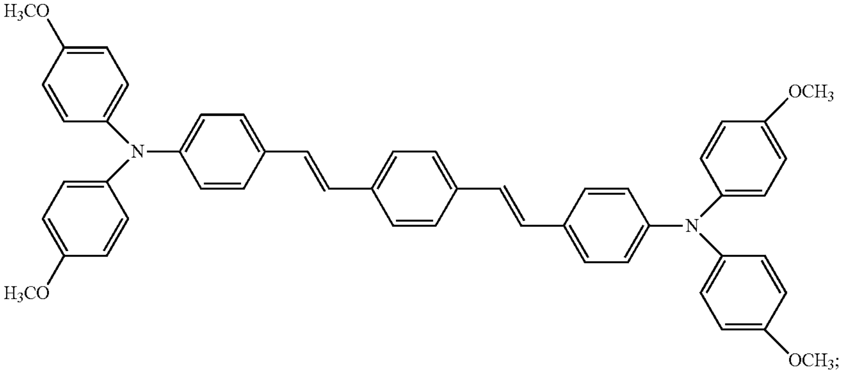
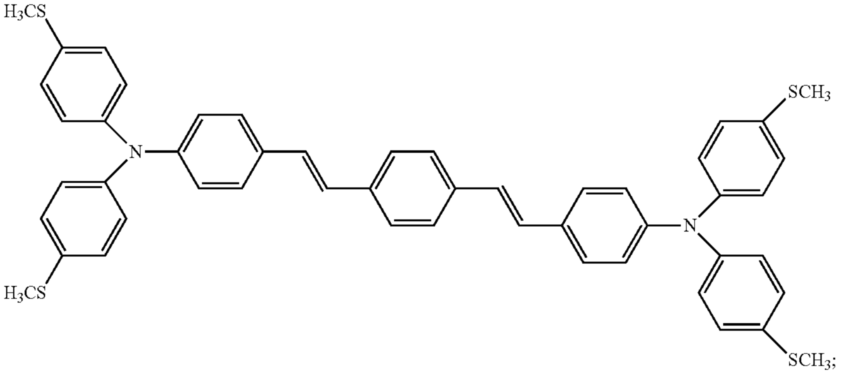

-continued

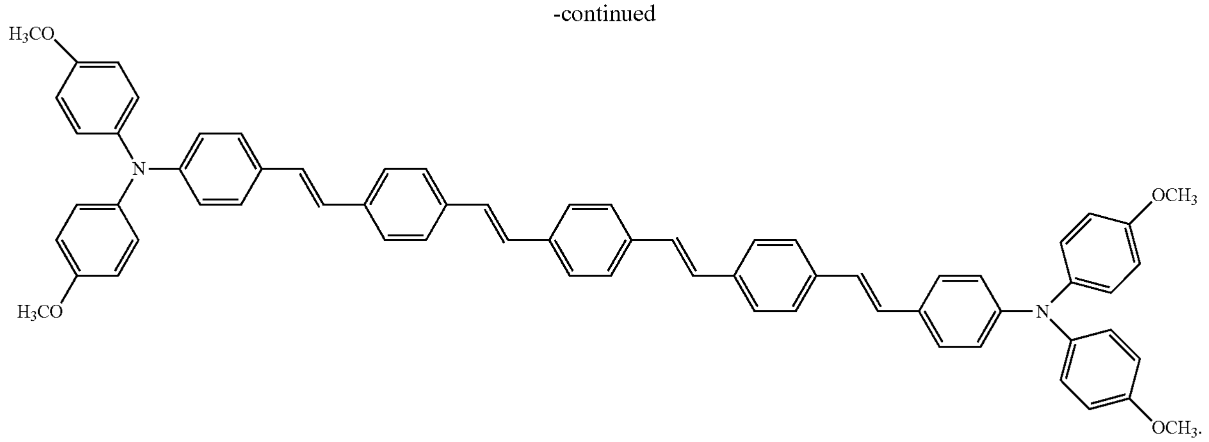

3. The hole transport layer forming composition for perovskite solar cells according to claim 1, wherein the hole transport layer forming composition is in the form of a hole transport layer applied to a perovskite layer.

4. The hole transport layer forming composition for perovskite solar cells according to claim 3, wherein the hole transport layer receives holes generated by the perovskite layer.

5. Perovskite solar cells having a hole transport layer comprising a compound represented by:

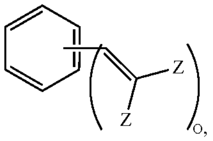

wherein, in the compound, o is an integer from 1 to 6 and wherein Z is independently hydrogen or represented by:

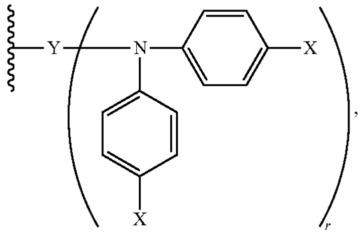

wherein X is an alkoxy group or an alkylthio group, wherein r is 1 or 2, and wherein Y is at least one species selected from the following groups:

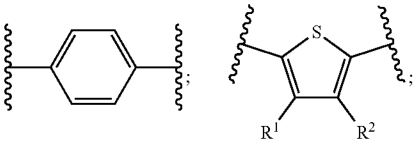

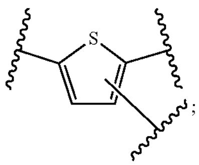

or

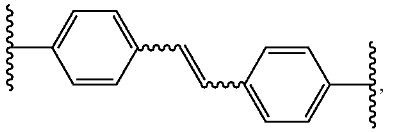

wherein $R^1$ and $R^2$ are independently hydrogen, alkyl groups, or alkoxy groups, or $R^1$ and $R^2$ are combined to form a ring having one or two oxygen atoms, and wherein Z is not all hydrogen.

* * * * *